(12) United States Patent
Cao et al.

(10) Patent No.: US 11,462,694 B2
(45) Date of Patent: Oct. 4, 2022

(54) IMIDAZOLE DERIVATIVE, MATERIAL AND ORGANIC LIGHT-EMITTING DEVICE COMPRISING THE SAME

(71) Applicant: SHIJIAZHUANG CHENGZHI YONGHUA DISPLAY MATERIAL CO., LTD., Hebei (CN)

(72) Inventors: Jianhua Cao, Hebei (CN); Liang Dong, Hebei (CN); Shibo Wang, Hebei (CN); Jianchuan Zhang, Hebei (CN); Yan Sui, Hebei (CN); Ruimao Hua, Hebei (CN)

(73) Assignee: SHIJIAZHUANG CHENGZHI YONGHUA DISPLAY MATERIAL CO., LTD., Hebei (CN)

( * ) Notice: Subject to any disclaimer, the term of this patent is extended or adjusted under 35 U.S.C. 154(b) by 298 days.

(21) Appl. No.: 16/631,006

(22) PCT Filed: Aug. 29, 2018

(86) PCT No.: PCT/CN2018/102898
§ 371 (c)(1),
(2) Date: Jan. 14, 2020

(87) PCT Pub. No.: WO2019/056932
PCT Pub. Date: Mar. 28, 2019

(65) Prior Publication Data
US 2020/0144516 A1 May 7, 2020

(30) Foreign Application Priority Data
Sep. 20, 2017 (CN) .......................... 201710851696.2

(51) Int. Cl.
H01L 51/00 (2006.01)
C07D 471/04 (2006.01)
(Continued)

(52) U.S. Cl.
CPC ........ H01L 51/0072 (2013.01); C07D 471/04 (2013.01); C07D 471/14 (2013.01);
(Continued)

(58) Field of Classification Search
None
See application file for complete search history.

(56) References Cited

U.S. PATENT DOCUMENTS

2017/0125696 A1* 5/2017 Park ..................... C07D 471/14

* cited by examiner

Primary Examiner — Jay Yang
(74) Attorney, Agent, or Firm — Paratus Law Group, PLLC

(57) ABSTRACT

There is provided an imidazole derivative, wherein the structural formula of the imidazole derivative is as represented by formula I:

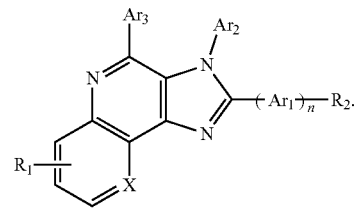

There is further provided a material containing the imidazole derivative and an organic light-emitting device containing the imidazole derivative. The imidazole derivative has an excellent carrier transport capacity, and the organic light-emitting device produced by using the material has obviously reduced starting voltage and improved luminous efficiency and luminance; and due to the features such as relatively good film-forming performance and simple material synthesis and purification methods which are applicable
(Continued)

to mass production, the imidazole derivative is an ideal option for an electron transport material of organic light-emitting devices.

19 Claims, 7 Drawing Sheets

(51) Int. Cl.
    *C07D 471/14*     (2006.01)
    *H01L 27/32*     (2006.01)
    *H01L 51/50*     (2006.01)
    *C09K 11/06*     (2006.01)

(52) U.S. Cl.
    CPC ............ *C09K 11/06* (2013.01); *H01L 51/006* (2013.01); *H01L 51/0061* (2013.01); *C09K 2211/1018* (2013.01); *H01L 51/5072* (2013.01); *H01L 2251/558* (2013.01)

IMIDAZOLE DERIVATIVE, MATERIAL AND ORGANIC LIGHT-EMITTING DEVICE COMPRISING THE SAME

CROSS REFERENCE TO PRIOR APPLICATION

This application is a National Stage Patent Application of PCT International Patent Application No. PCT/CN2018/102898 (filed on Aug. 29, 2018) under 35 U.S.C. § 371, which claims priority to Chinese Patent Application No. 201710851696.2 (filed on Sep. 20, 2017), which are all hereby incorporated by reference in their entirety.

TECHNICAL FIELD

The present invention relates to the technical field of organic light-emitting materials, and in particular to an imidazole derivative, a material and organic light-emitting device comprising the same.

BACKGROUND ART

Related research on organic light-emitting device (OLED for short) has been carried out as early as 1963, when Pope et al. first discovered the electroluminescence of the organic compound of single crystal anthracene. In 1987, the US Kodak Company produced an amorphous film device by means of evaporation of small organic molecules, reducing the driving voltage to below 20V. Due to the features such as ultra-thinness, full curing, self-luminescence, high luminance, a wide visual angle, a fast response speed, a low driving voltage, low power consumption, bright in colour, high contrast, a simple production process, a good temperature property, and flexible display, such the device can be widely used in flat panel displays and area light sources, and thus has been widely researched, developed and used.

After more than 20 years of development, organic EL materials have completely implement red, blue, and green light emission, and the application field has been expanded from the field of small molecules to the field such as macromolecules and metal complexes. In recent years, the organic electroluminescence display technology has been matured, and some products have entered the market. However, in industrialization, there are still many urgent problems to be solved, in particular for various organic materials used to produce the devices, there are still many problems which yet have not been solved, such as the carrier injection and transport properties, the material electroluminescence property, the service life, the color purity, and matching between various materials and between various materials and various electrodes. In particular, the light-emitting devices cannot satisfy the practical requirements in terms of the luminous efficiency and service life, which greatly limits the development of the OLED technology. The metal complex phosphorescent material that implements triplet state light emission has high luminous efficiency, and green and red light-emitting materials thereof can satisfy the requirements for use; however, due to the special electronic structural feature of the metal complex, the blue light-emitting material thereof cannot satisfy the requirements for use.

After more than 20 years of development, organic EL materials have completely implement red, blue, and green light emission, and the application field has been expanded from the field of small molecules to the field such as macromolecules and metal complexes. In recent years, the organic electroluminescence display technology has been matured, and some products have entered the market. However, in industrialization, there are still many urgent problems to be solved, in particular for various organic materials used to produce the devices, there are still many problems which yet have not been solved, such as the carrier injection and transport properties, the material electroluminescence property, the service life, the color purity, and matching between various materials and between various electrodes.

Therefore, there is a need to provide an imidazole derivative that can improve the electron mobility, reduce the driving voltage, and improve the luminance and efficiency of the device, so as to solve at least one of the above problems.

SUMMARY OF THE INVENTION

An objective of the present invention is to provide an imidazole derivative.

Another objective of the present invention is to provide a material containing the imidazole derivative.

A third objective of the present invention is to provide an organic light-emitting device.

In order to achieve the above objectives, the present invention employs the following technical solutions:

An imidazole derivative has a structural formula as represented by formula I:

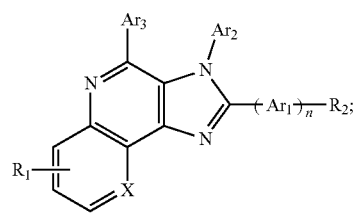

wherein $R_1$ and $R_2$ respectively and independently represent hydrogen, deuterium, a $C_1$-$C_8$ linear or branched alkyl group, a $C_1$-$C_8$ linear or branched alkoxy group, a substituted or unsubstituted $C_6$-$C_{60}$ aryl group, a substituted or unsubstituted $C_6$-$C_{60}$ aryl vinyl group, a substituted or unsubstituted $C_6$-$C_{60}$ fused-ring aryl group, a substituted or unsubstituted $C_6$-$C_{60}$ arylamine group, a substituted or unsubstituted $C_6$-$C_{60}$ nitrogen atom-containing fused-ring aryl group, a substituted or unsubstituted $C_6$-$C_{60}$ sulfur or oxygen atom-containing fused-ring aryl group, a substituted or unsubstituted $C_6$-$C_{60}$ phosphorus, silicon, or boron atom-containing fused-ring aryl group, or a substituted or unsubstituted $C_2$-$C_{60}$ heterocyclic aryl group;

$Ar_1$, $Ar_2$, and $Ar_3$ respectively and independently represent a substituted or unsubstituted phenyl group, a substituted or unsubstituted naphthyl group, a substituted or unsubstituted fluorenyl group, a substituted or unsubstituted spirofluorenyl group, a substituted or unsubstituted anthryl group, a substituted or unsubstituted pyridyl group, a substituted or unsubstituted pyrimidyl group, a substituted or unsubstituted quinolyl group and/or a substituted or unsubstituted carbazolyl group, or a substituted or unsubstituted $C_2$-$C_{60}$ heterocyclic aryl group;

n represents an integer of 1-5; and x represents a carbon atom or a nitrogen atom.

Preferably, the cyclic structure of the substituted or unsubstituted $C_2$-$C_{60}$ heterocyclic aryl group contains at least one of N, O, and S atoms.

Preferably, in the $R_1$, $R_2$, $Ar_1$, $Ar_2$, and $Ar_3$ groups, the $C_2$-$C_{60}$ heterocyclic aryl groups are respectively and independently selected from one or a plurality of the following structures of formulas II-1 to II-15:

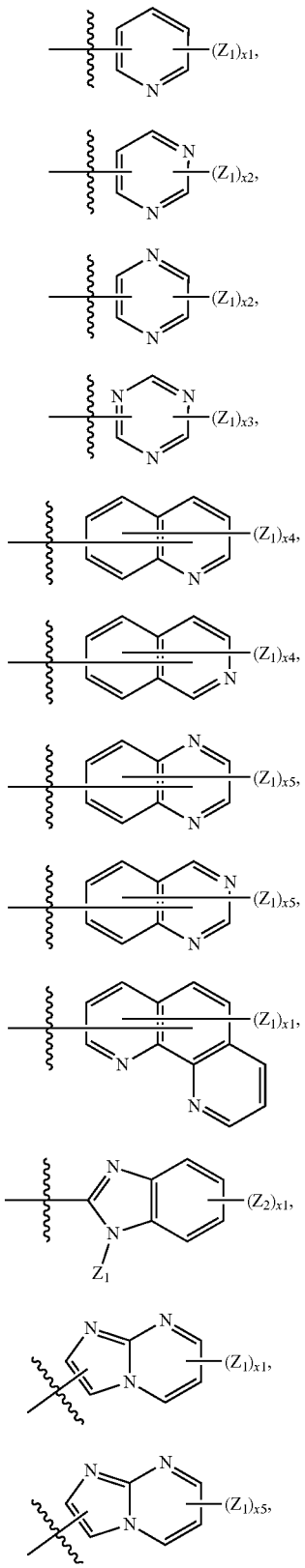

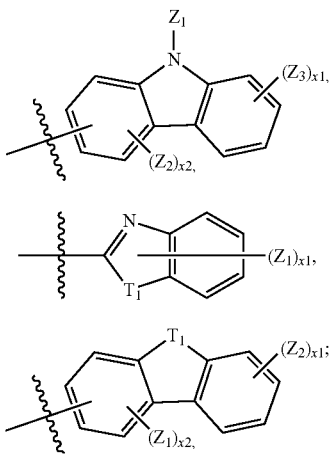

wherein $Z_1$, $Z_2$, and $Z_3$ respectively and independently represent hydrogen, deuterium, a halogen atom, a hydroxyl group, a nitrile group, a nitro group, an amino group, an amidine group, a hydrazine group, a hydrazone group, a carboxyl group or a carboxylate thereof, a sulfonic group or a sulfonate thereof, a phosphate group or a phosphate thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkane group, a $C_3$-$C_{60}$ cycloolefin group, a $C_6$-$C_{60}$ aryl group, a $C_6$-$C_{60}$ aryl group containing at least one of —F, —CN, or a $C_1$-$C_{10}$ alkyl group, a substituted or unsubstituted $C_6$-$C_{60}$ aryloxy group, a substituted or unsubstituted $C_6$-$C_{60}$ aryl thioether group, or a substituted or unsubstituted $C_2$-$C_{60}$ heterocyclic aryl group;

x1 represents an integer of 1-4; x2 represents an integer of 1-3; x3 represents an integer of 1 or 2; x4 represents an integer of 1-6; x5 represents an integer of 1-5;

$T_1$ represents an oxygen atom or a sulfur atom; and

∿∿∿ represents a bond between a substituent and a main structure.

Preferably, $Ar_1$ contains but is not limited to the following structures of III-1 to III-16:

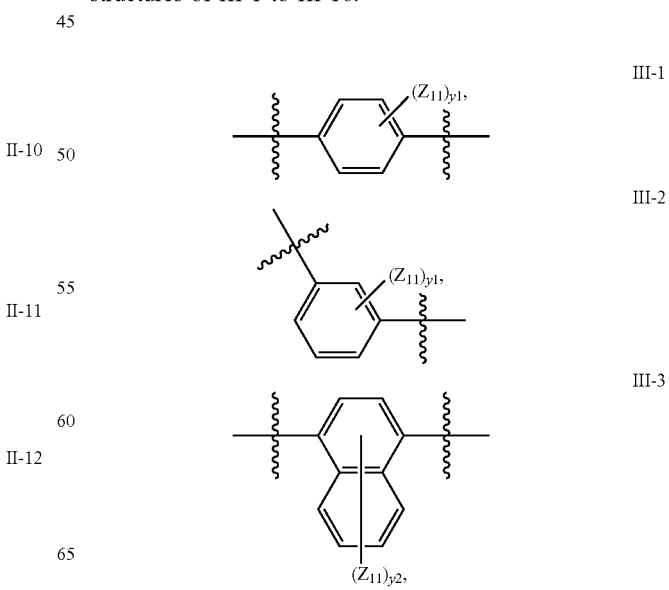

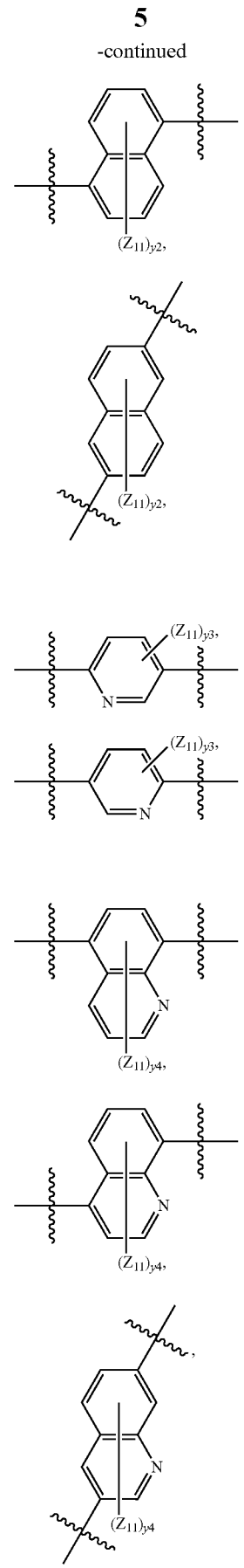
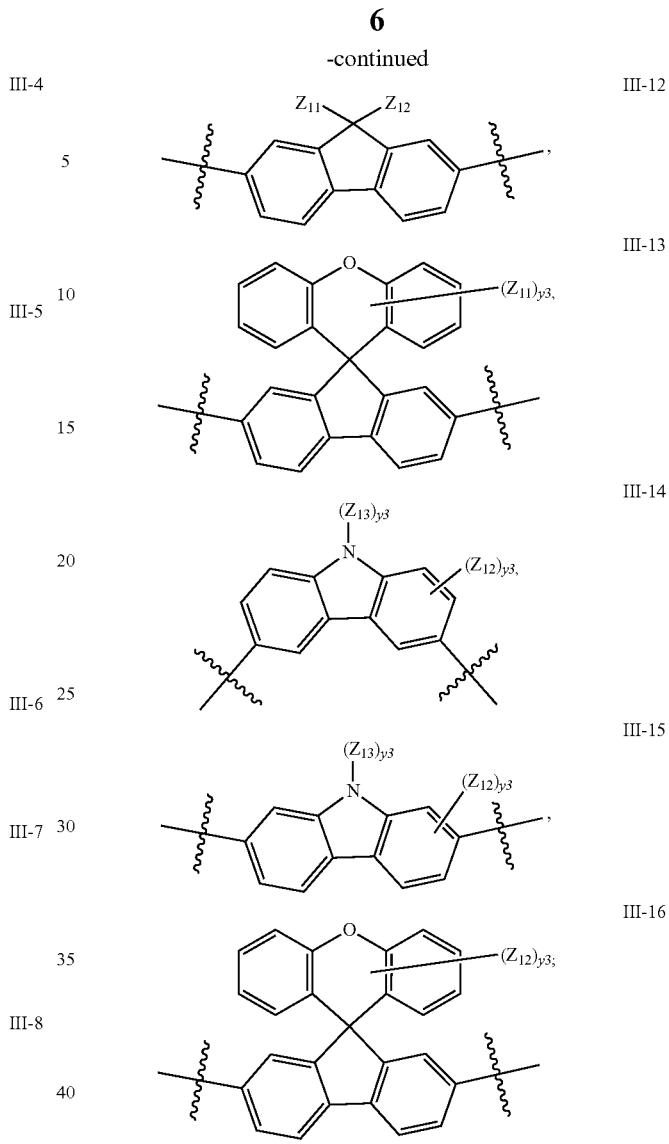

wherein $Z_{11}$ and $Z_{12}$ respectively and independently represent hydrogen, deuterium, a halogen atom, a hydroxyl group, a nitrile group, a nitro group, an amino group, an amidine group, a hydrazine group, a hydrazone group, a carboxyl group or a carboxylate thereof, a sulfonic group or a sulfonate thereof, a phosphate group or a phosphate thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkane group, a $C_3$-$C_{60}$ cycloolefin group, a $C_6$-$C_{60}$ aryl group, a $C_6$-$C_{60}$ aryl group containing at least one of —F, —CN, or a $C_1$-$C_{10}$ alkyl group, a substituted or unsubstituted $C_6$-$C_{60}$ aryloxy group, a substituted or unsubstituted $C_6$-$C_{60}$ aryl thioether group, or a substituted or unsubstituted $C_2$-$C_{60}$ heterocyclic aryl group;

$Z_{13}$ represents a substituted or unsubstituted $C_6$-$C_{60}$ aryl group, a substituted or unsubstituted $C_6$-$C_{60}$ aryloxy group, a substituted or unsubstituted $C_6$-$C_{60}$ aryl thioether group, or a substituted or unsubstituted $C_2$-$C_{60}$ heterocyclic aryl group; and y1 represents an integer of 1-4; y2 represents an integer of 1-6; y3 represents an integer of 1-3; and y4 represents an integer of 1-5.

Preferably, the structural formula of the compound having a structural formula I is specifically represented by any one of but is not limited to the following formulas CJH-P01 to CJH-P100:
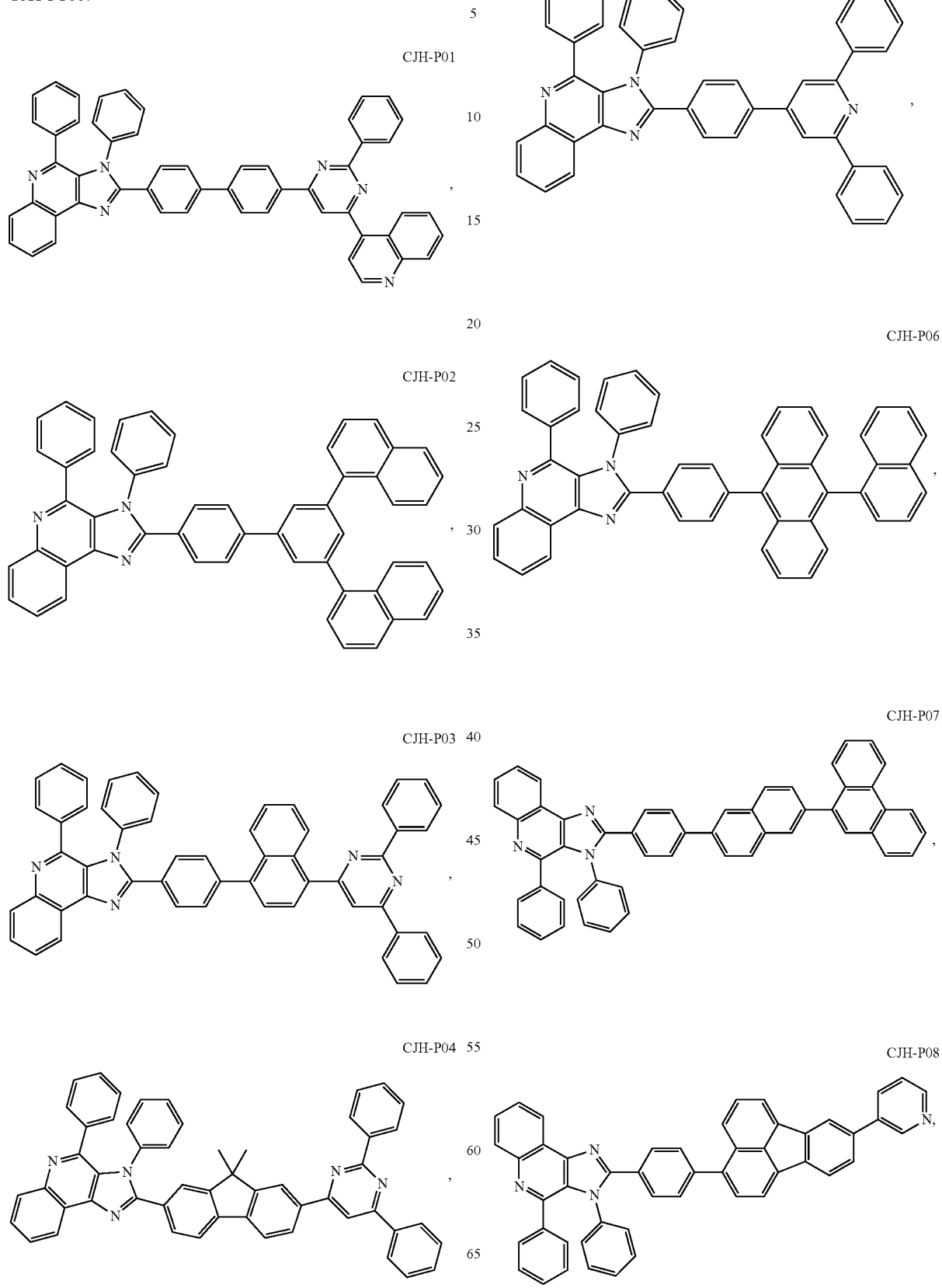

CJH-P09
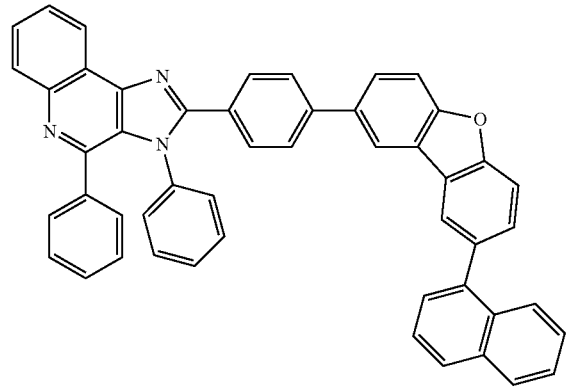
CJH-P13
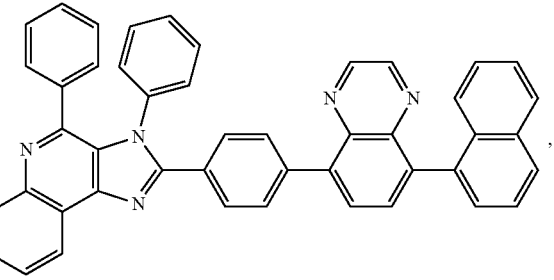
CJH-P10
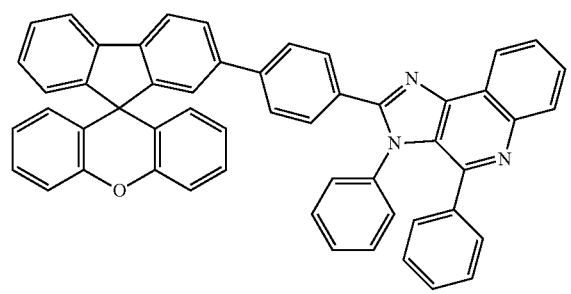
CJH-P14
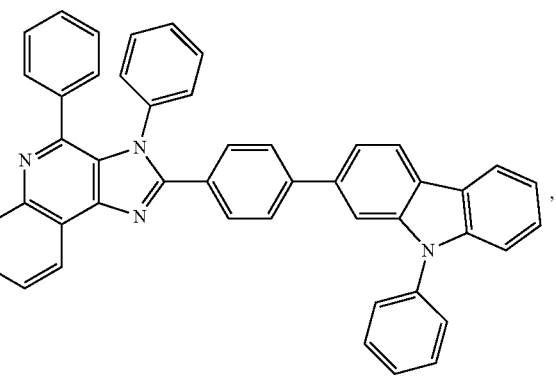
CJH-P11
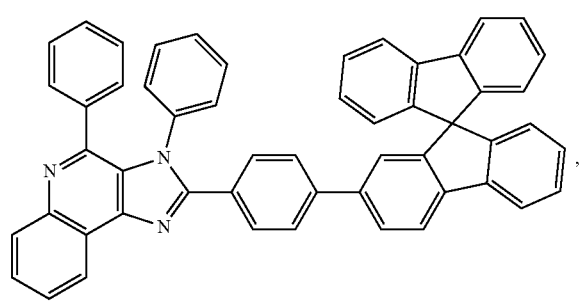
CJH-P15
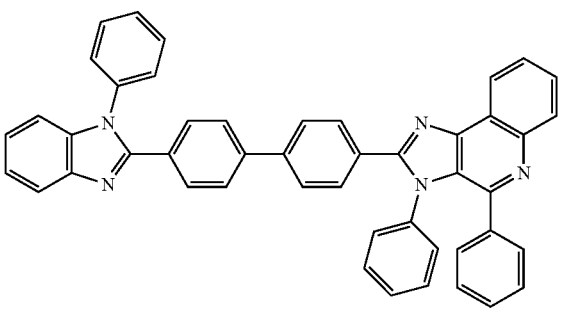
CJH-P12
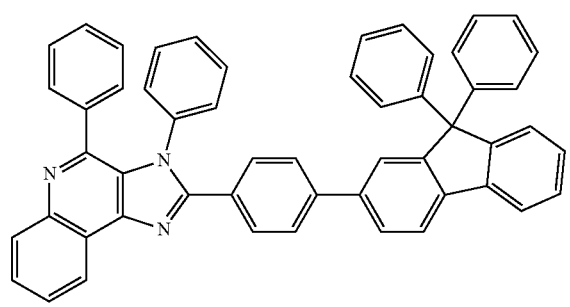
CJH-P16
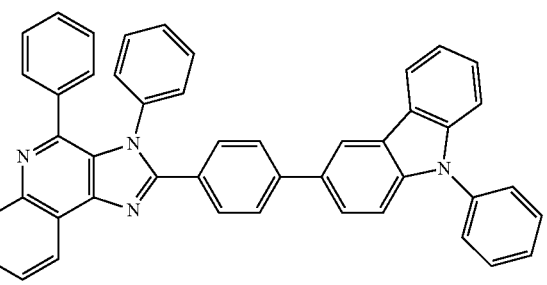

CJH-P17
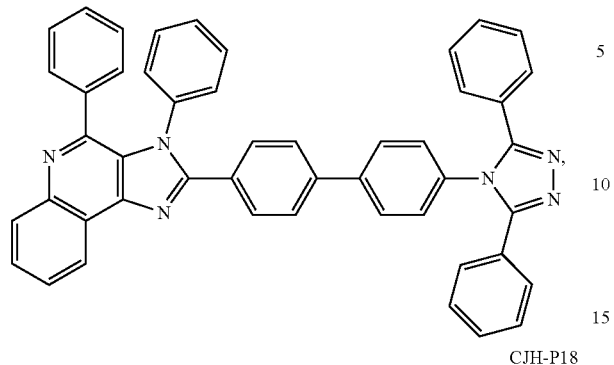
CJH-P22
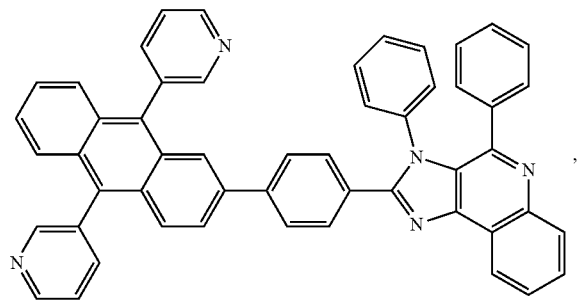
CJH-P18
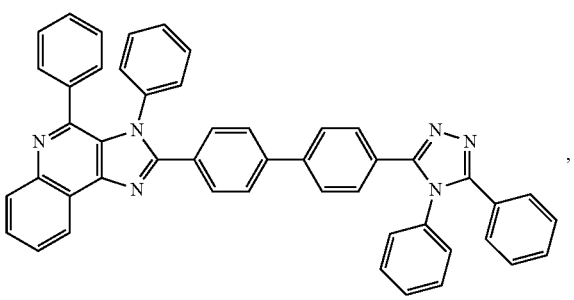
CJH-P23
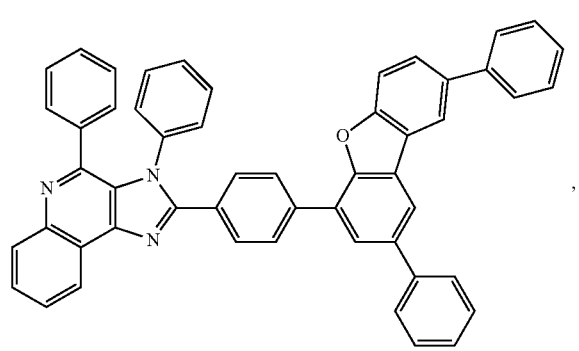
CJH-P19
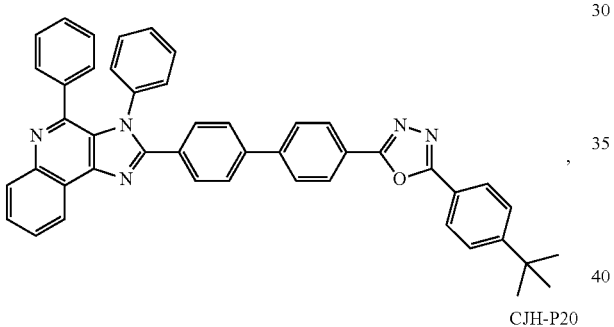
CJH-P20
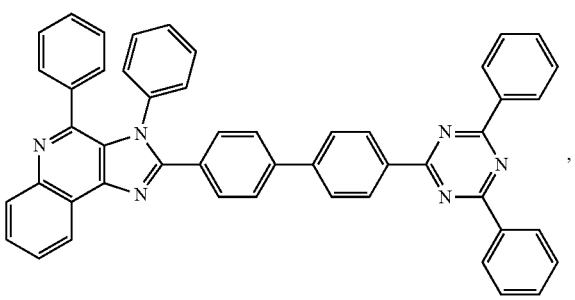
CJH-P24
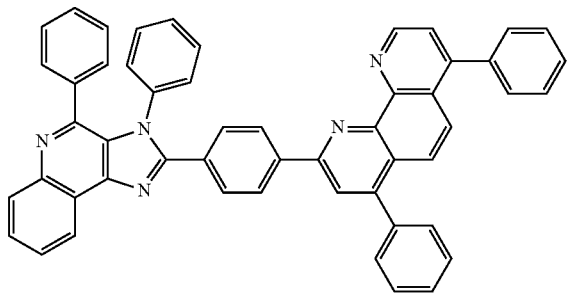
CJH-P21
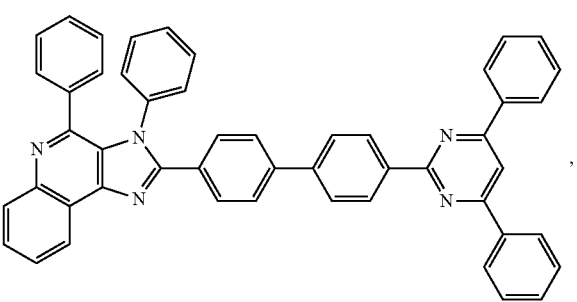
CJH-P25
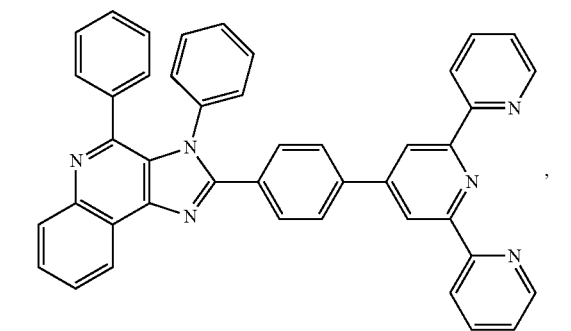

-continued
CJH-P26
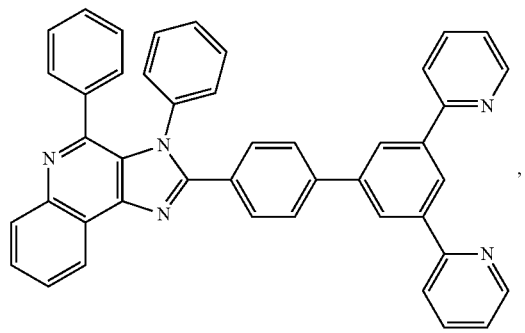
CJH-P27
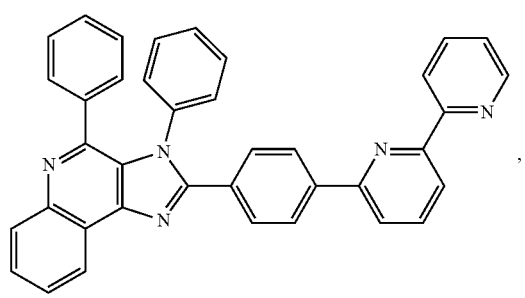
CJH-P28
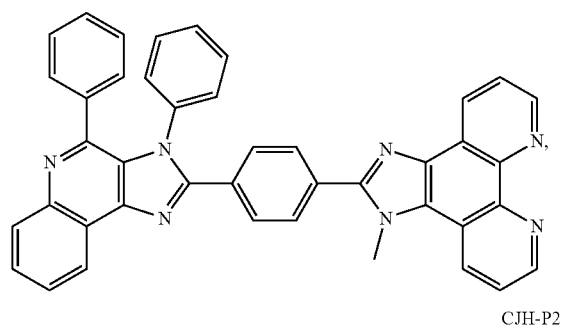
CJH-P29
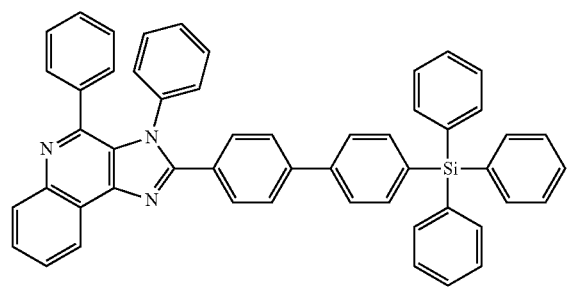
CJH-P30
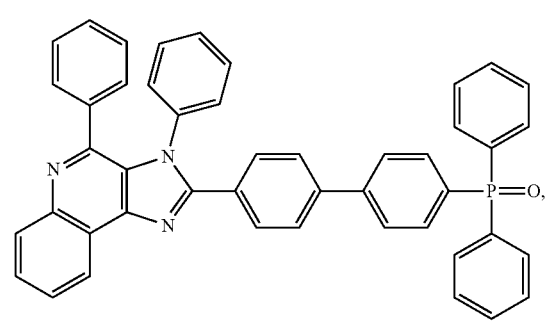
-continued
CJH-P31
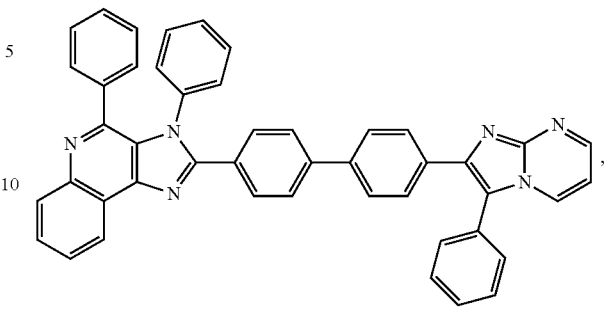
CJH-P32
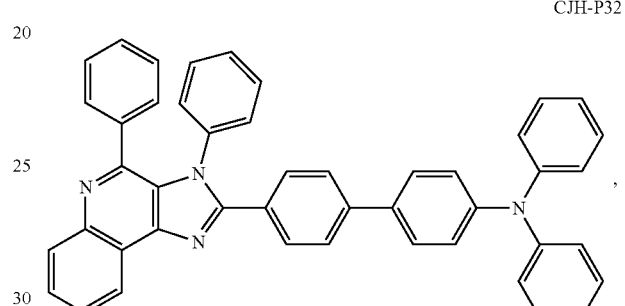
CJH-P33
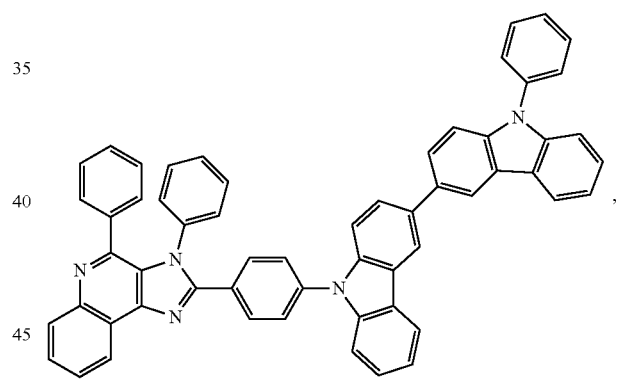
CJH-P34
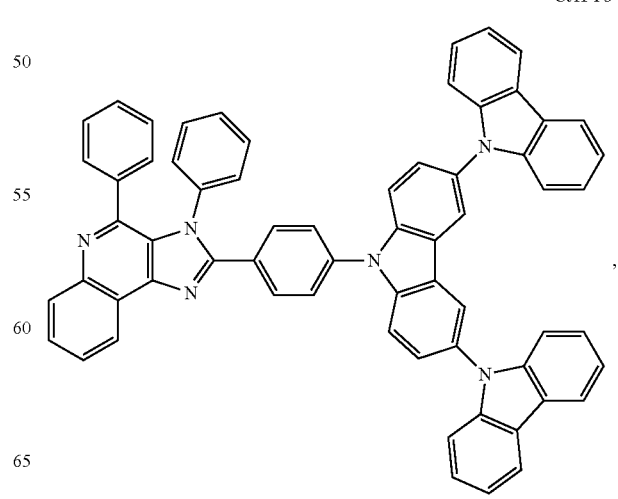

-continued
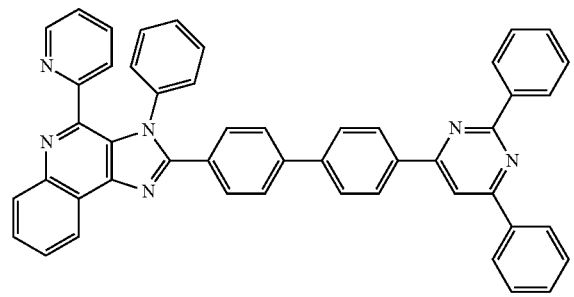
CJH-P35
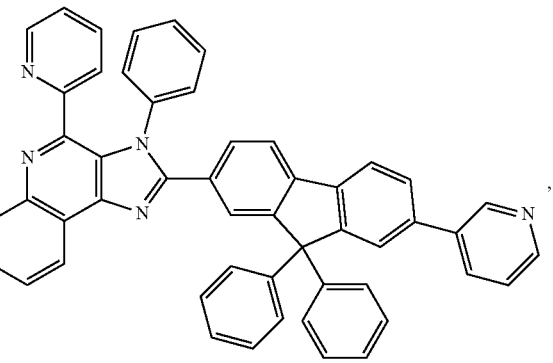
CJH-P39
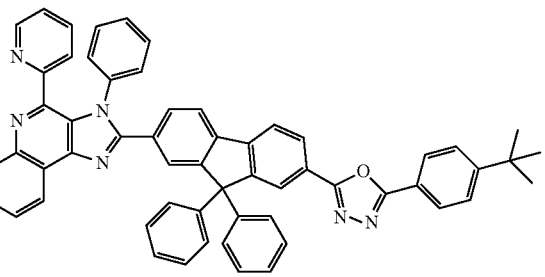
CJH-P40
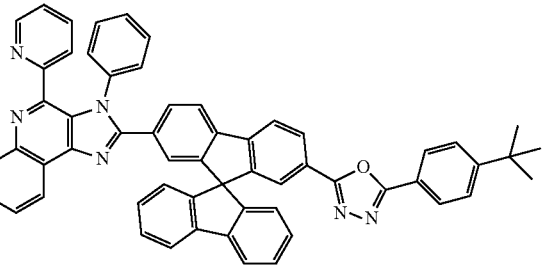
CJH-P41
CJH-P36
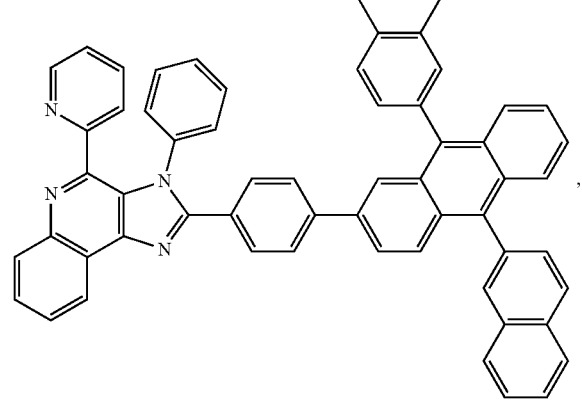
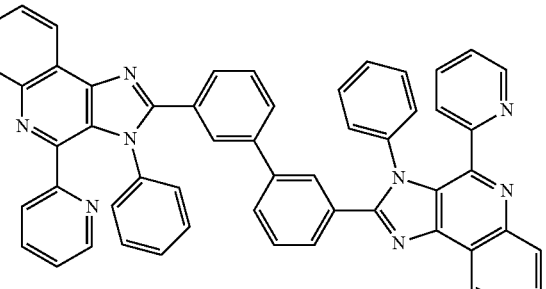
CJH-P42
CJH-P37
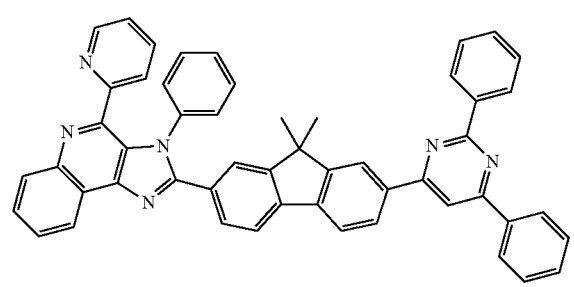
CJH-P38
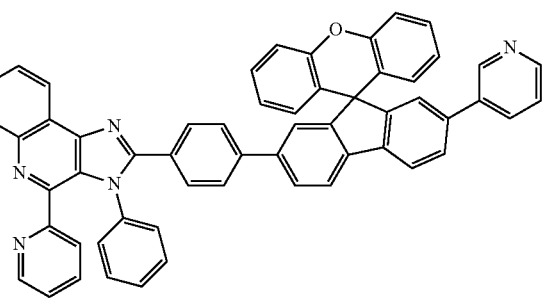
CJH-P43

CJH-P44
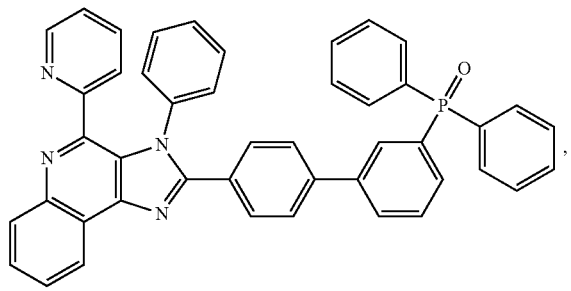
CJH-P45
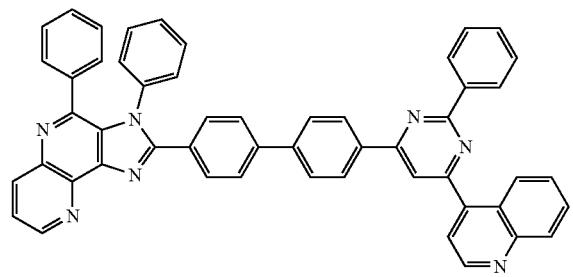
CJH-P46
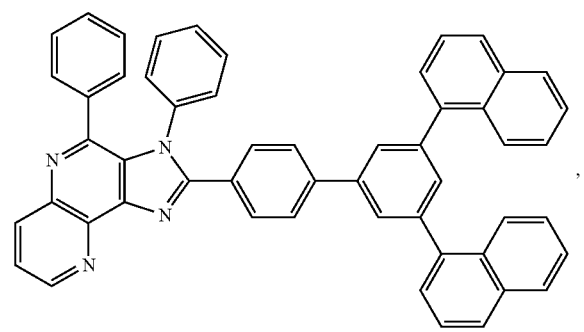
CJH-P47
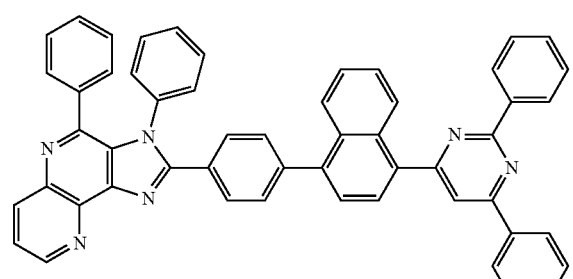
CJH-P48
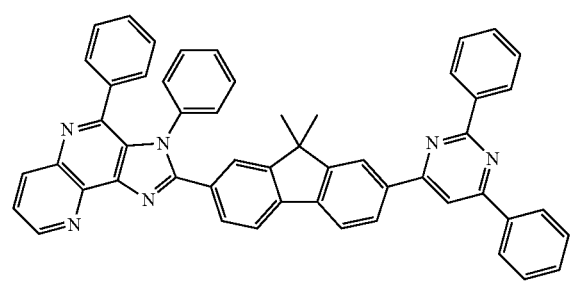
CJH-P49
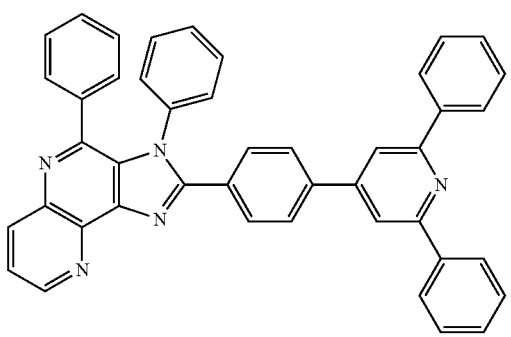
CJH-P50
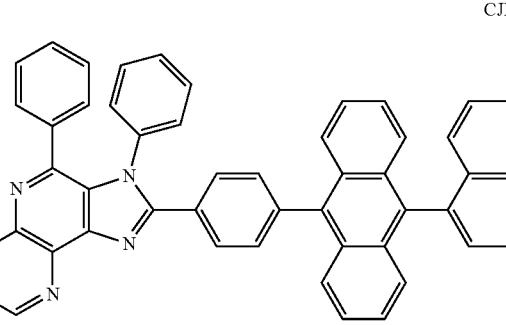
CJH-P51
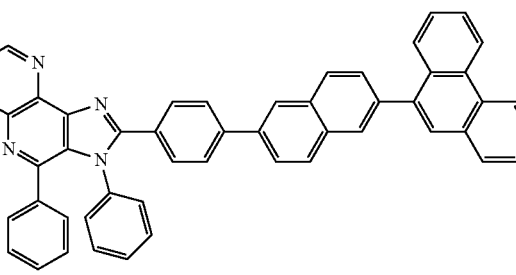
CJH-P52

CJH-P53
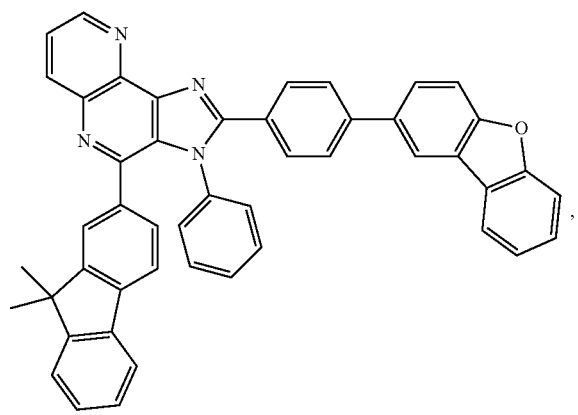
CJH-P54
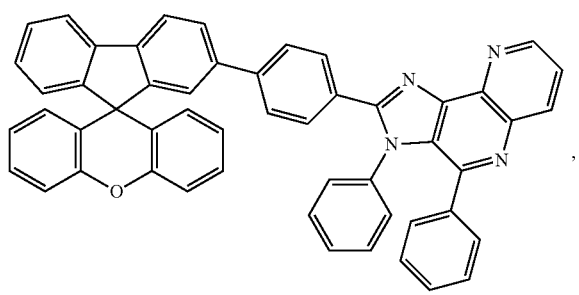
CJH-P55
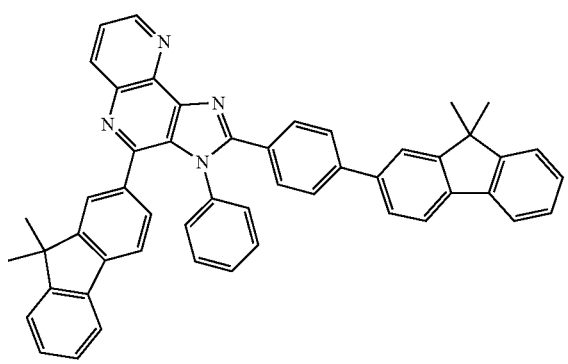
CJH-P56
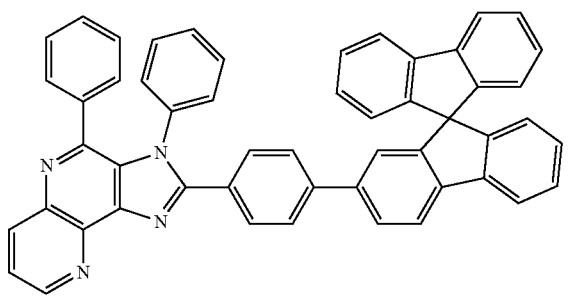
CJH-P57
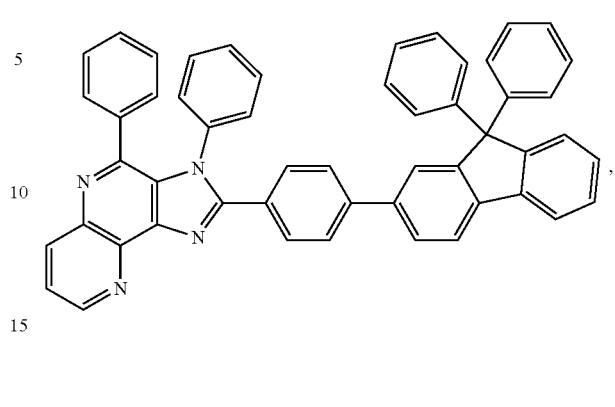
CJH-P58
CJH-P59
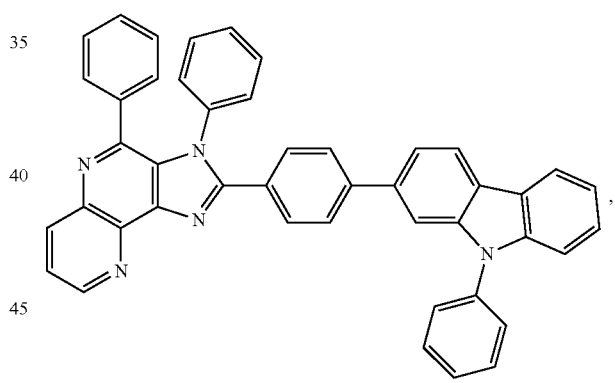
CJH-P60
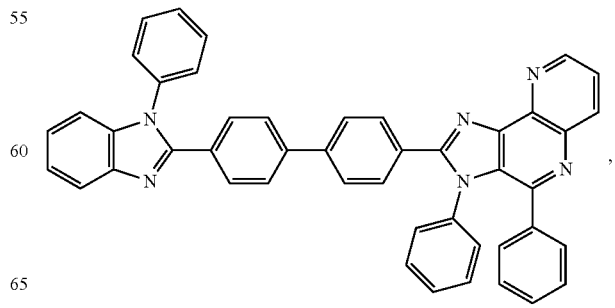

-continued
CJH-P61
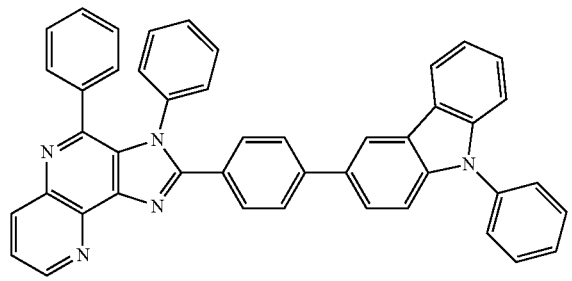,
CJH-P62
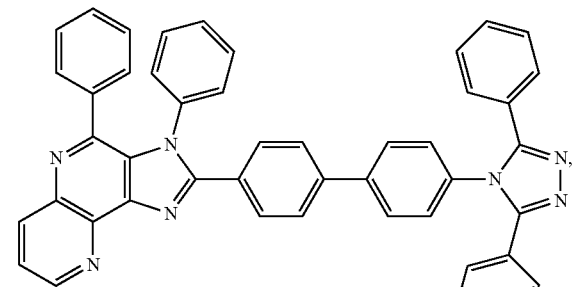,
CJH-P63
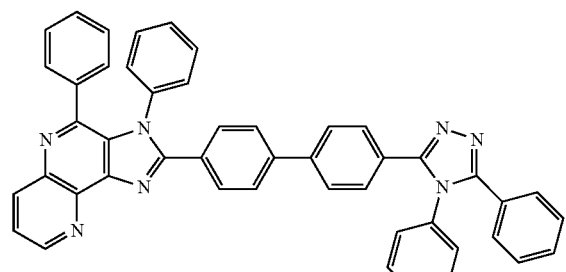,
CJH-P64
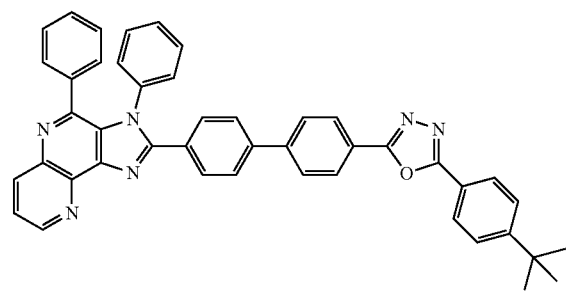,
CJH-P65
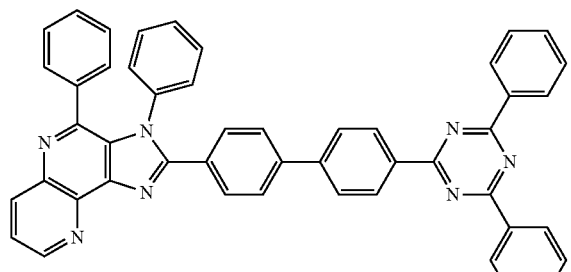,
-continued
CJH-P66
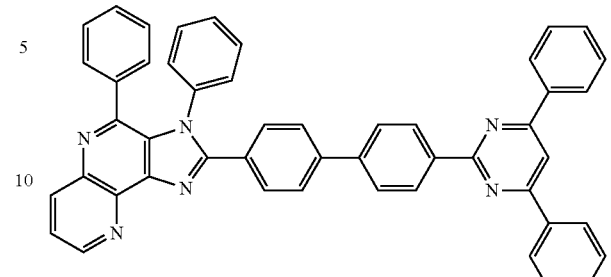,
CJH-P67
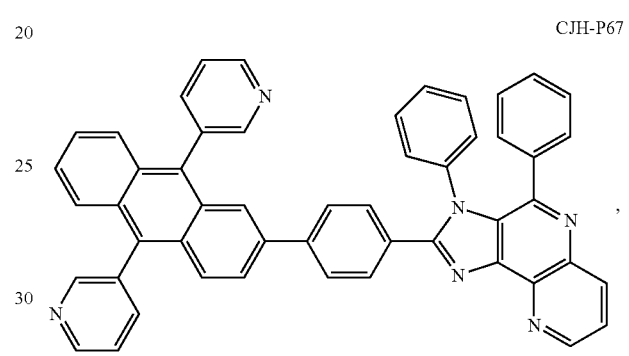,
CJH-P68
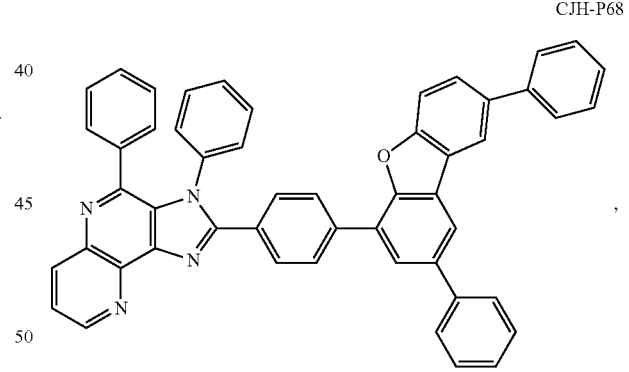,
CJH-P69
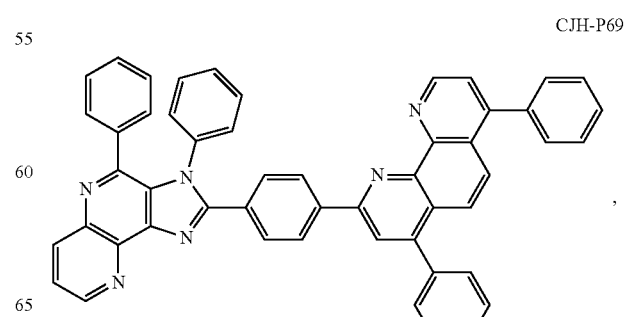, -continued
CJH-P70
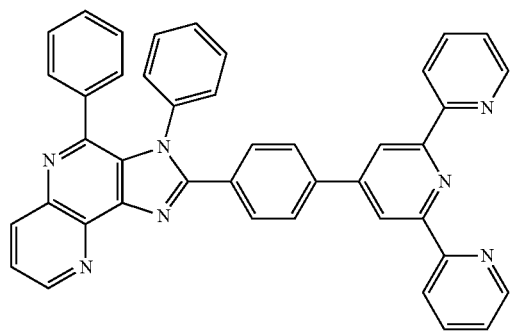
CJH-P74
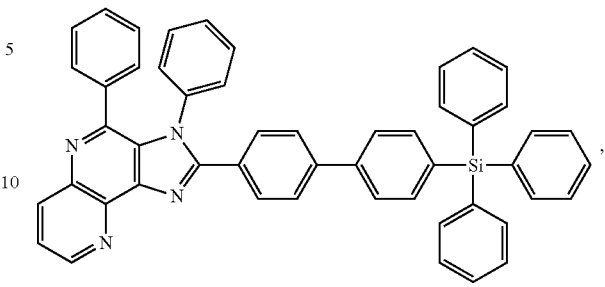
CJH-P71
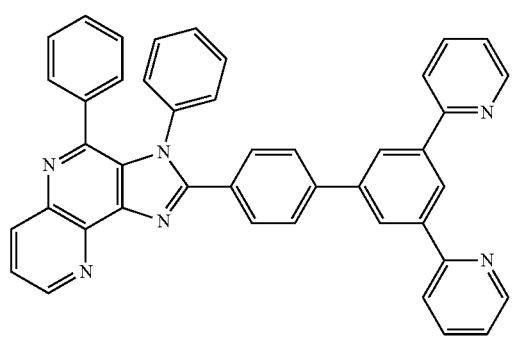
CJH-P75
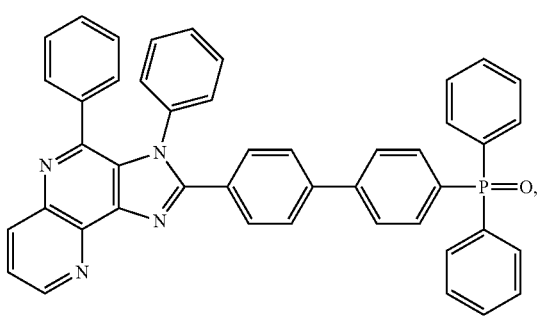
CJH-P72
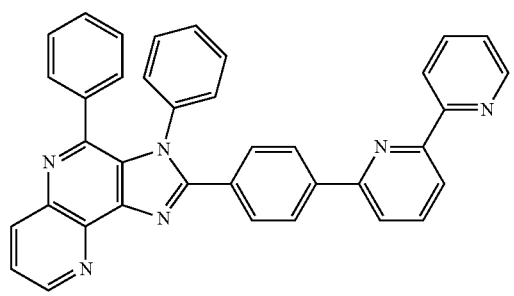
CJH-P76
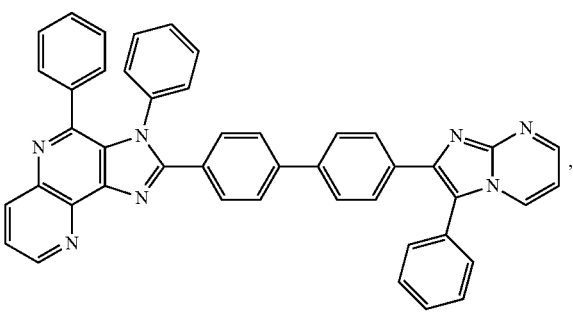
CJH-P73
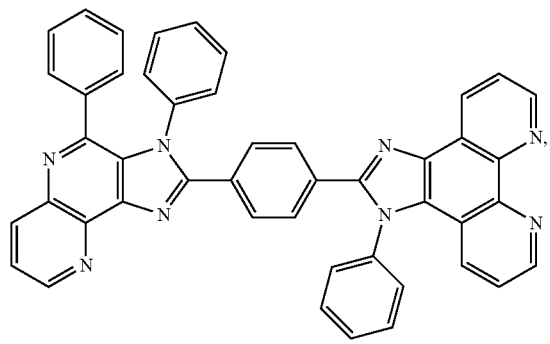
CJH-P77
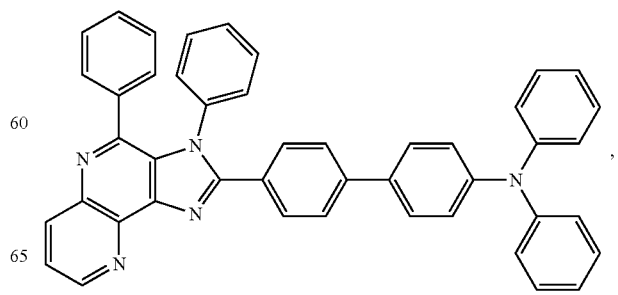

-continued
CJH-P78
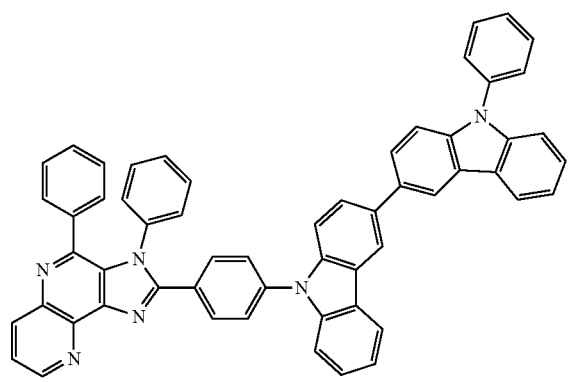,
CJH-P79
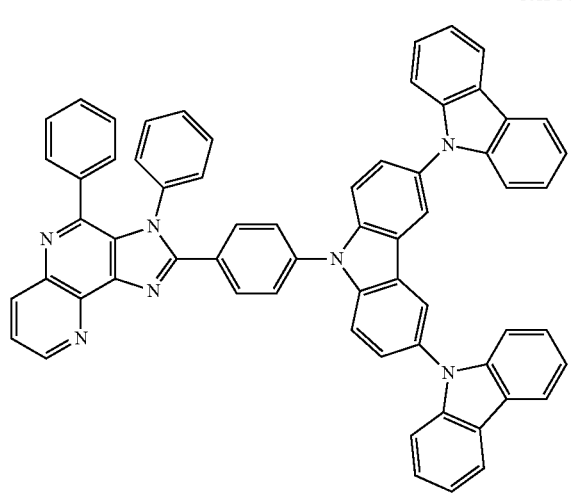,
CJH-P80
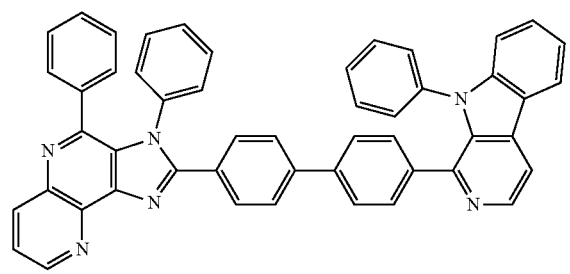,
CJH-P81
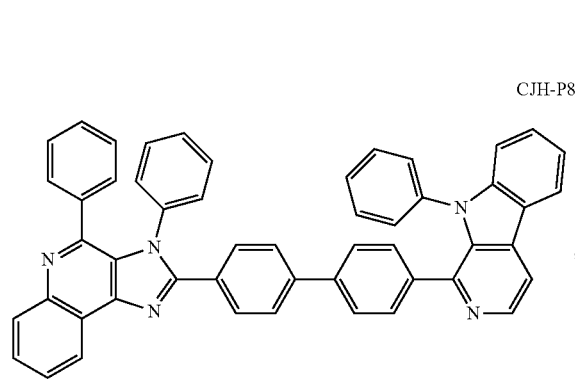,
-continued
CJH-P82
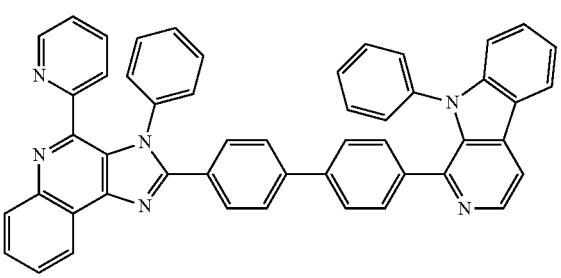,
CJH-P83
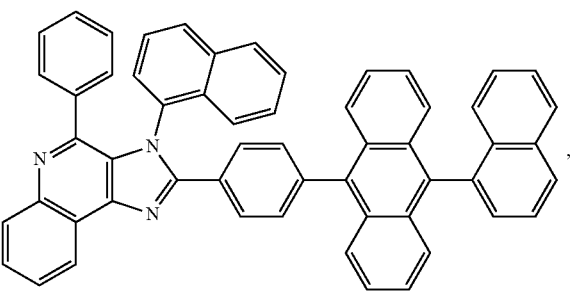,
CJH-P84
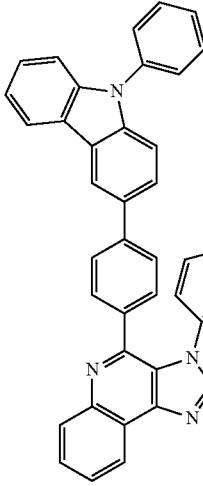,
CJH-P85
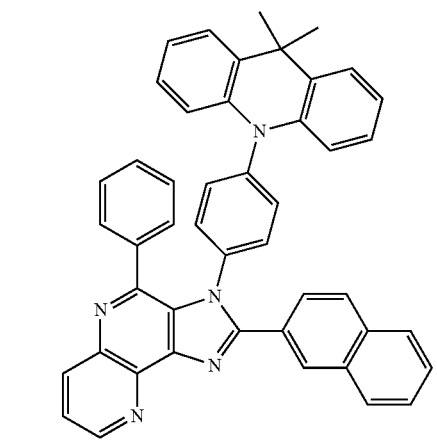, CJH-P86
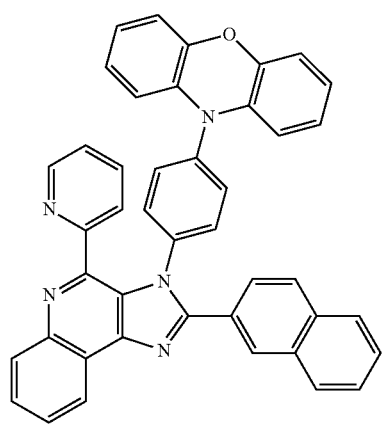
CJH-P90
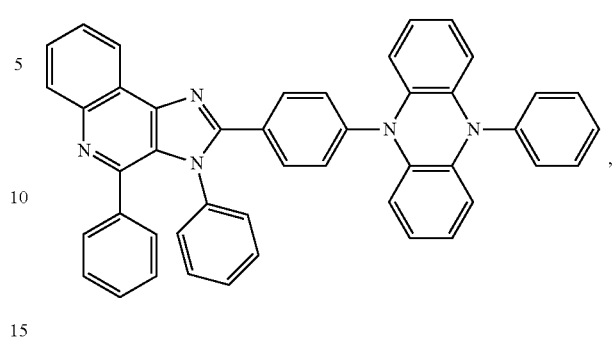
CJH-P87
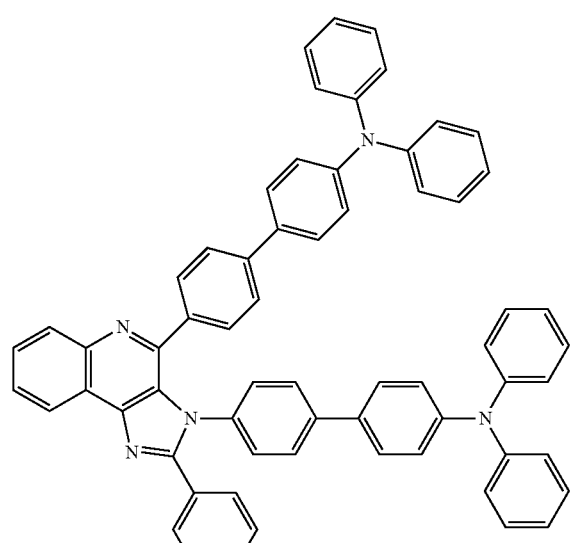
CJH-P91
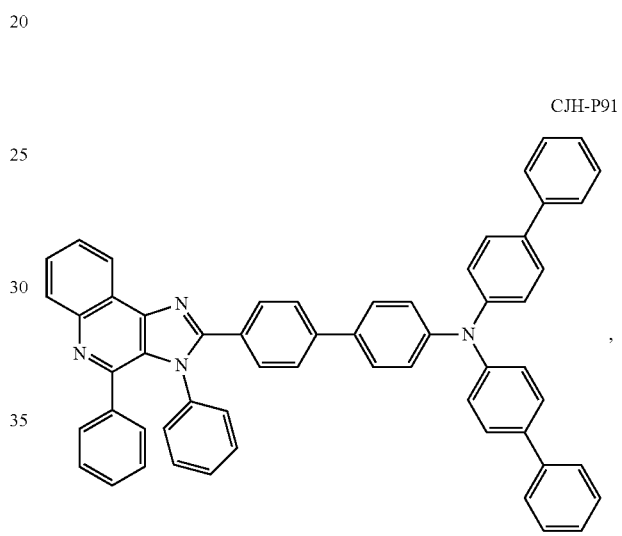
CJH-P88
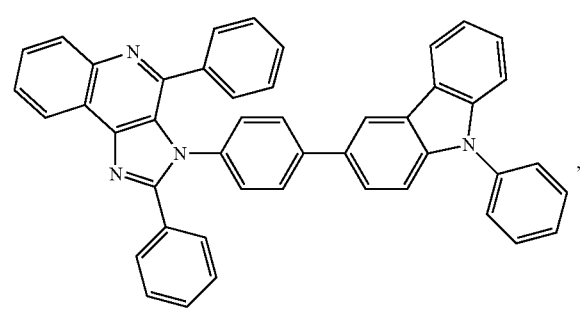
CJH-P92
CJH-P89
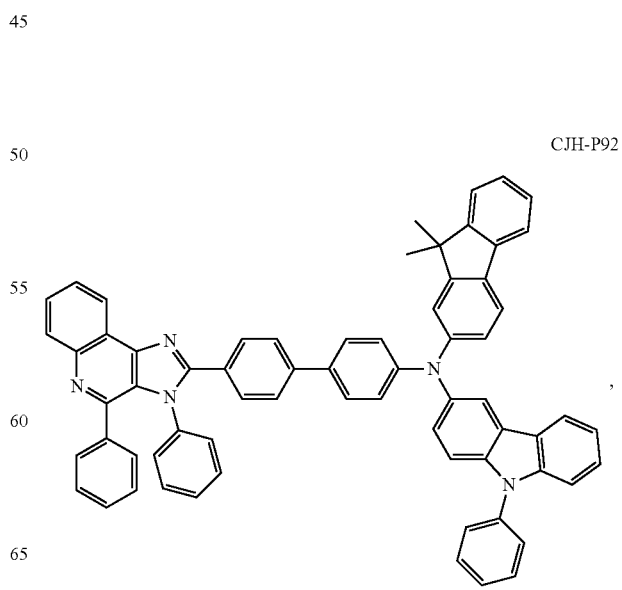

CJH-P93
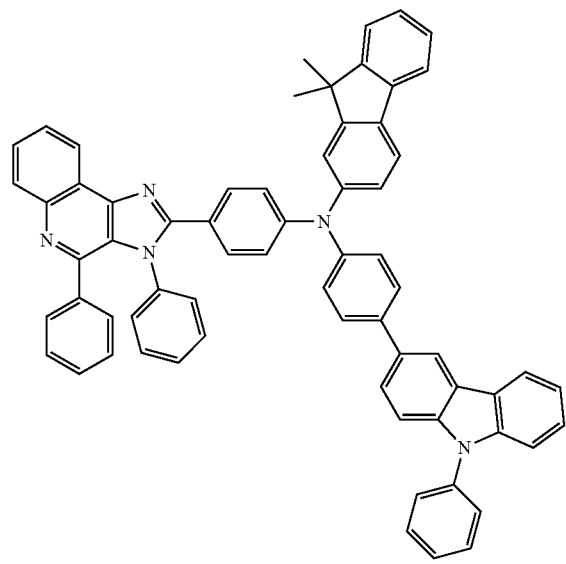
CJH-P94
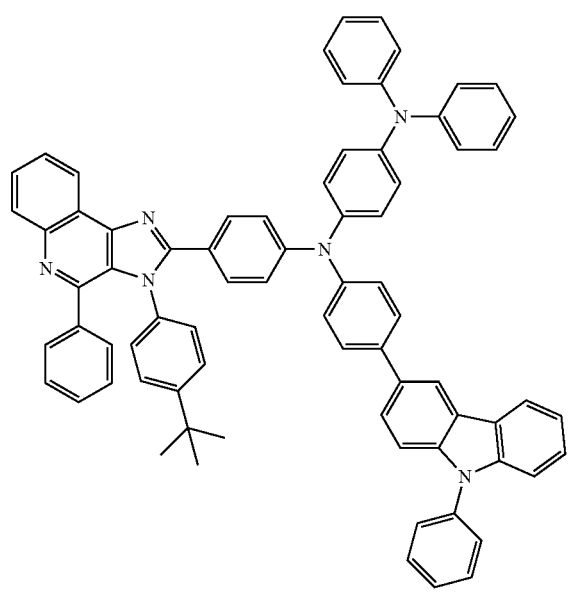
CJH-P95
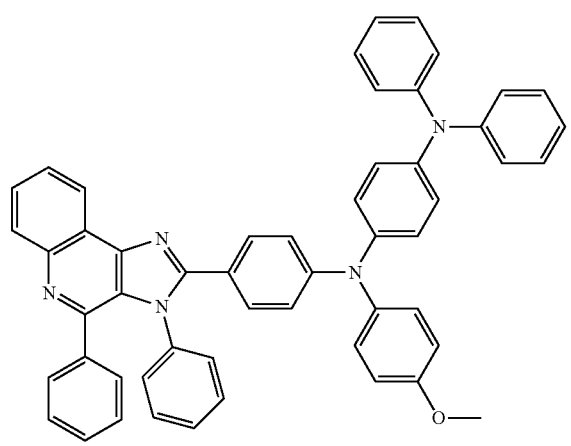
CJH-P96
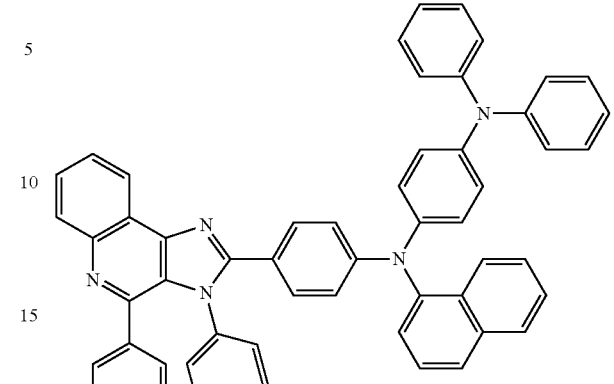
CJH-P97
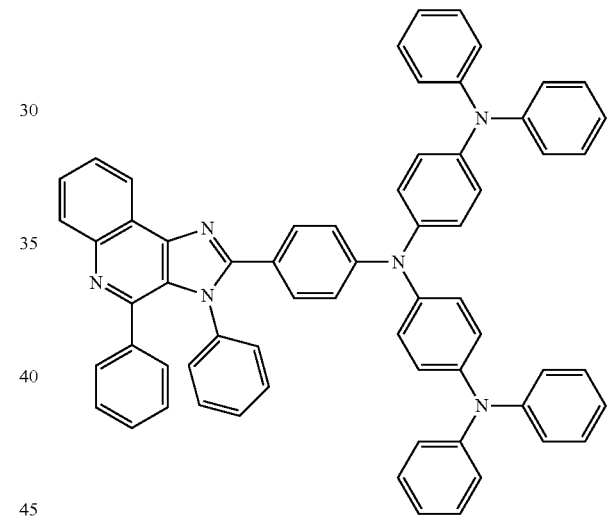
CJH-P98
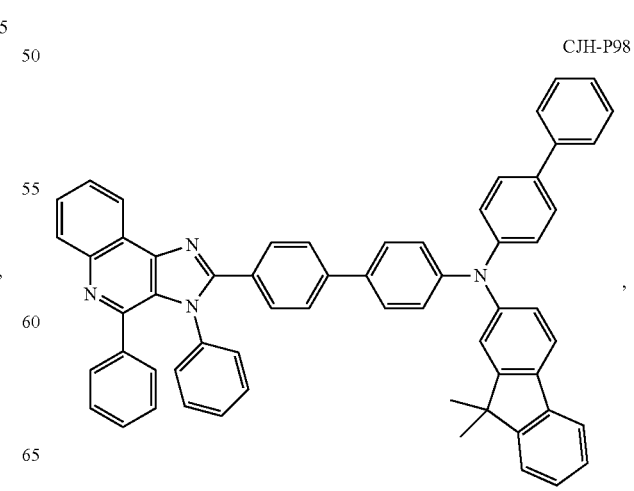

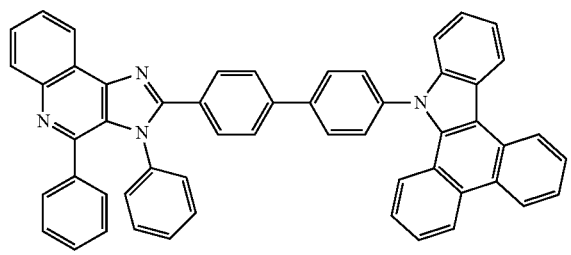

CJH-P99

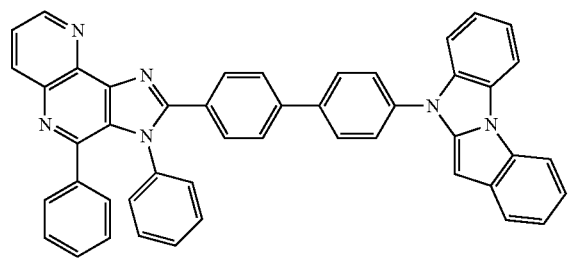

CJH-P100

In order to achieve the above second objective, the present invention further provides a material, wherein a raw material of the material contains one or a plurality of the above imidazole derivatives.

Preferably, the material is an organic light-emitting material. The material containing the compound of the present invention has the capability of carrier transport.

In order to achieve the above third objective, the present invention further provides an organic light-emitting device, wherein the material of the organic light-emitting device contains one or a plurality of the above imidazole derivatives. The organic light-emitting device of the present invention can be either a top-emitting device or a bottom-emitting device. The structure and preparation method of the organic light-emitting device are not limited in the present invention. The organic light-emitting device produced by using the compound of the present invention has a reduced starting voltage and improved luminous efficiency and luminance.

Preferably, the organic light-emitting device comprises a substrate, an anode layer disposed on the substrate, a hole transport layer disposed on the anode layer, an organic light-emitting layer disposed on the hole transport layer, an electron transport layer disposed on the organic light-emitting layer, and a cathode layer disposed on the electron transport layer.

Preferably, the material of at least one of the hole transport layer, the organic light-emitting layer, and the electron transport layer in the organic light-emitting device contains one or a plurality of the above imidazole derivatives.

Preferably, the material of the substrate is glass or a flexible substrate.

Preferably, the material of the anode layer is an inorganic material or organic conductive polymer, wherein the inorganic material is indium tin oxide, zinc oxide, tin zinc oxide, gold, silver, or copper, and the organic conductive polymer is selected from at least one of polythiophene, sodium polyvinyl benzene sulfonate, and polyaniline.

Preferably, the material of the hole transport layer further comprises but is not limited to one or a plurality of the following compounds:

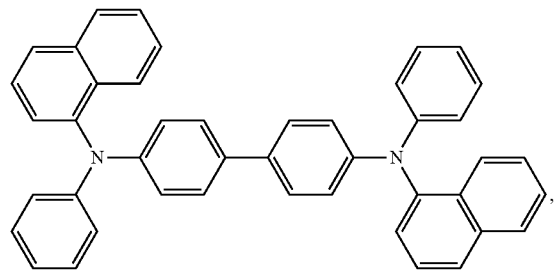

NPB

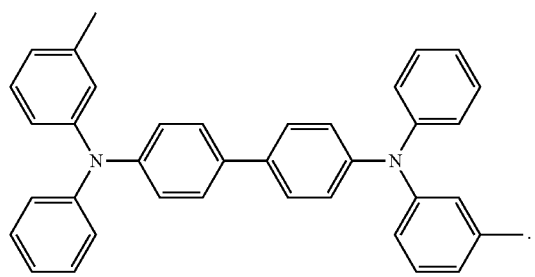

TPD

Preferably, the material of the organic light-emitting layer further comprises but is not limited to one or a plurality of the following compounds:

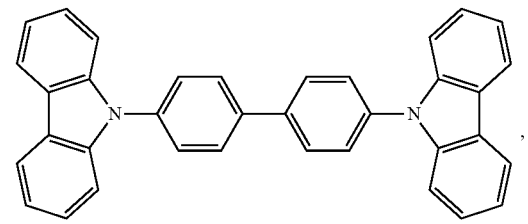

CBP

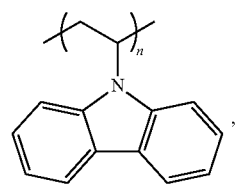

PVK

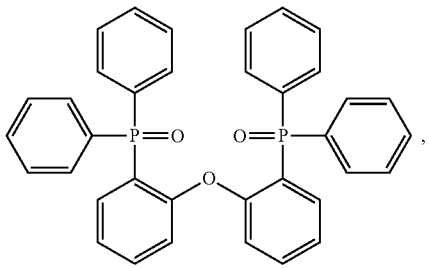

-continued
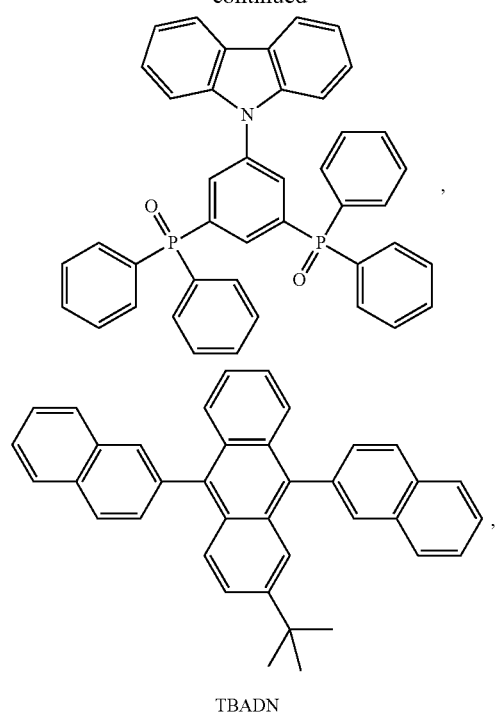
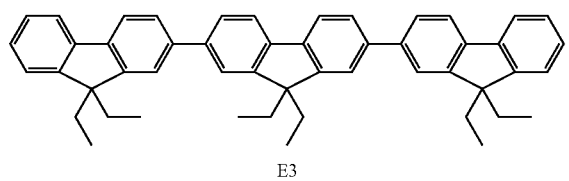
TBADN
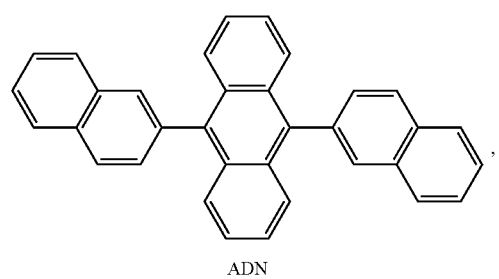
E3
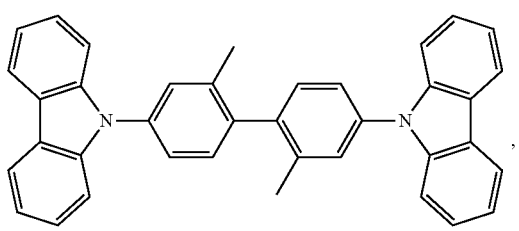
ADN
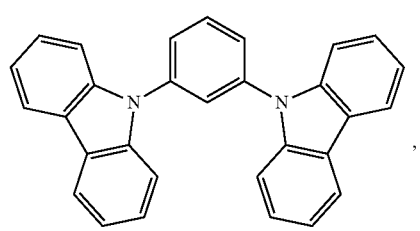
dmCBP
mCP
-continued
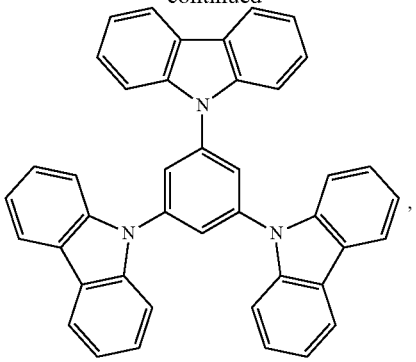
TCzP
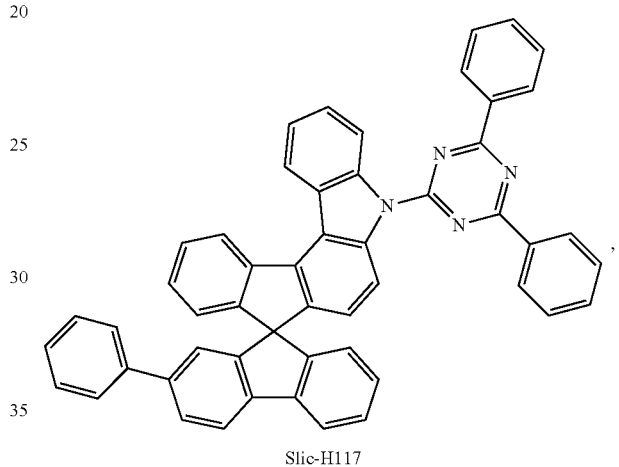
Slic-H117
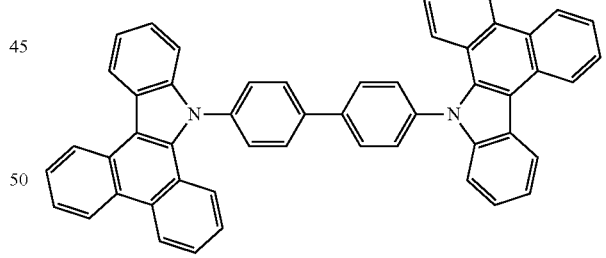
BCPB
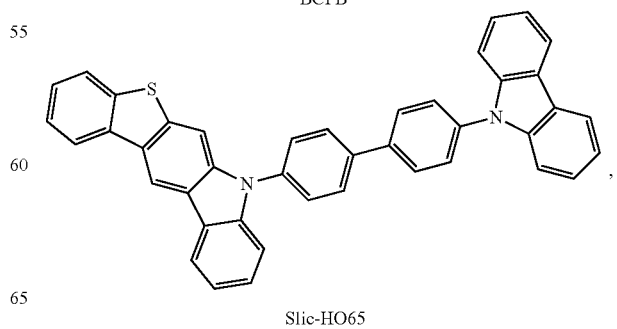
Slic-HO65

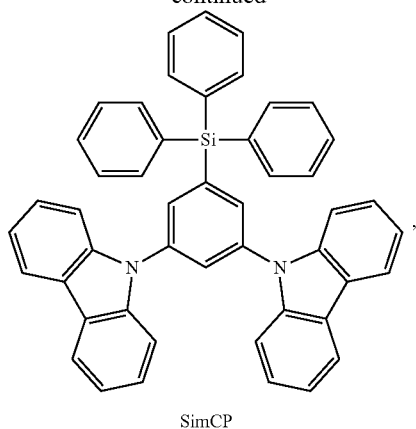
SimCP
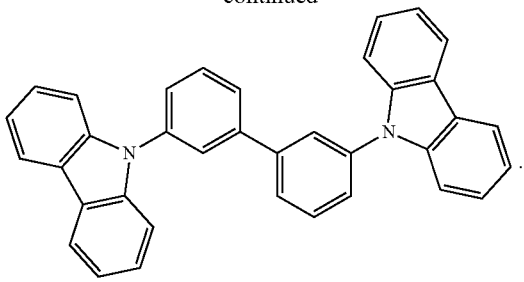
mCBP
Preferably, the material of the organic light-emitting layer further comprises doping materials, wherein the doping materials comprise red, green, and blue doping materials.
Preferably, the blue doping material comprises but is not limited to one or a plurality of the following compounds:
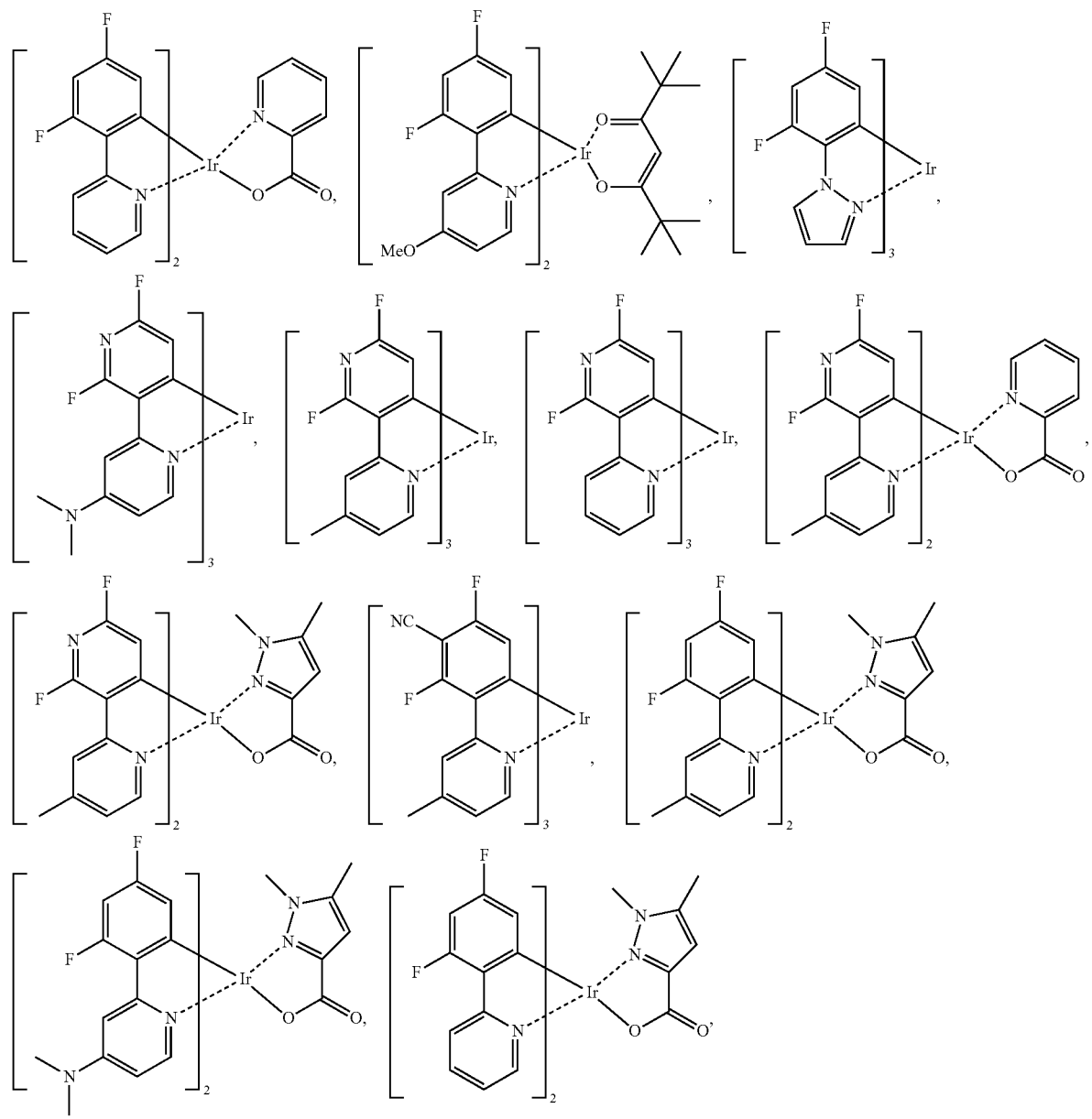

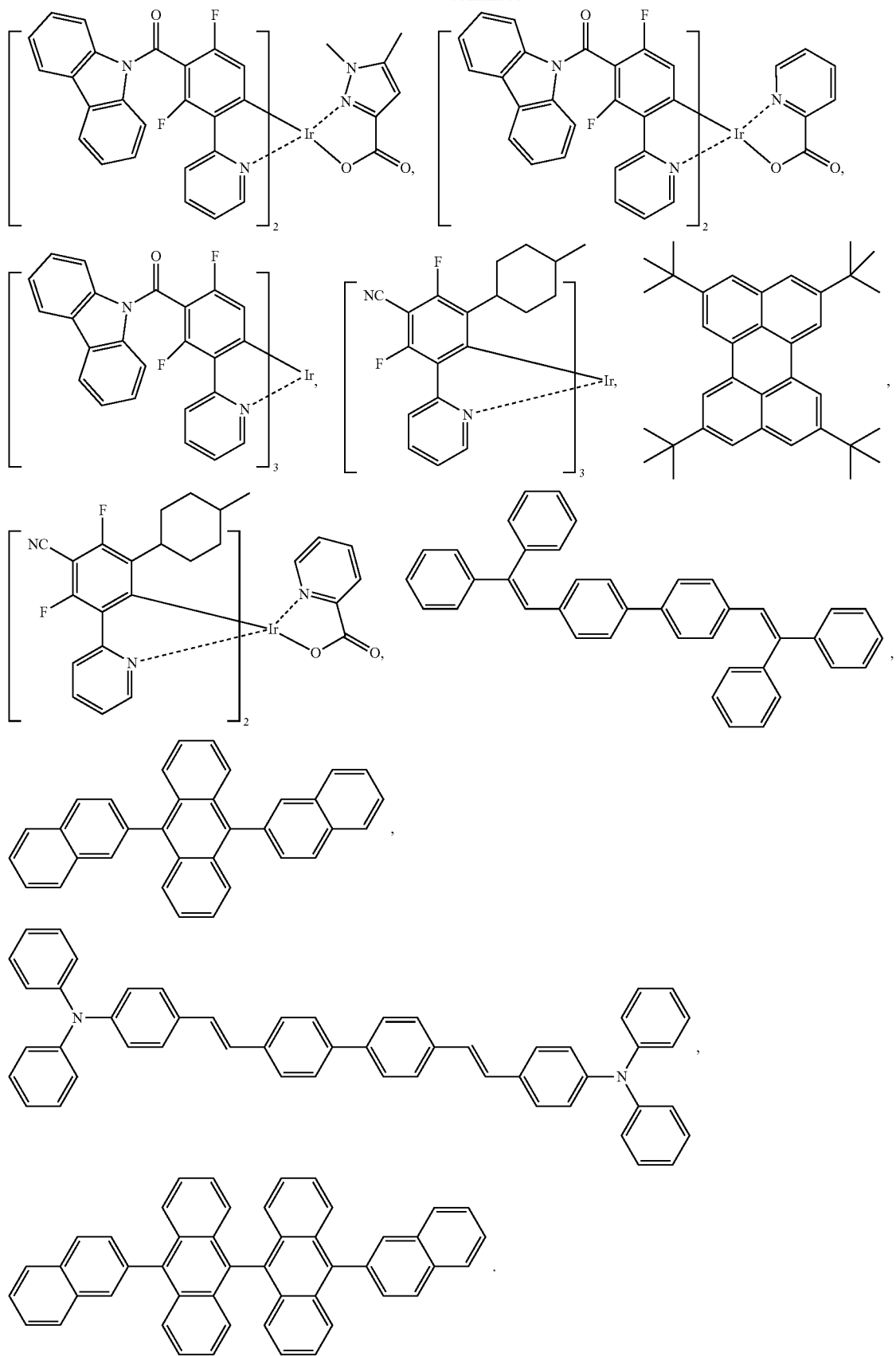

Preferably, the red doping material comprises but is not limited to one or a plurality of the following compounds:
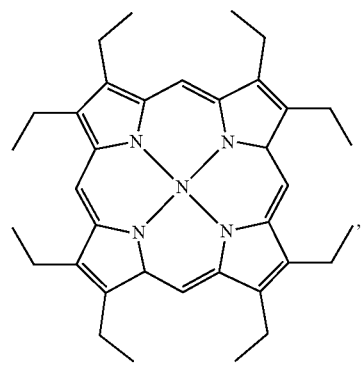
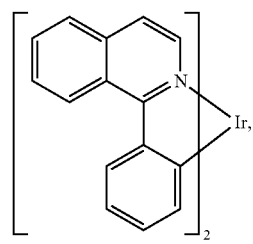
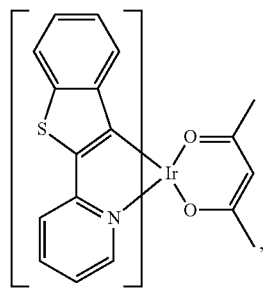
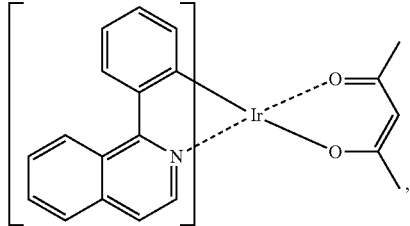
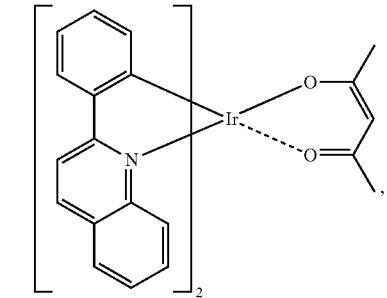
-continued
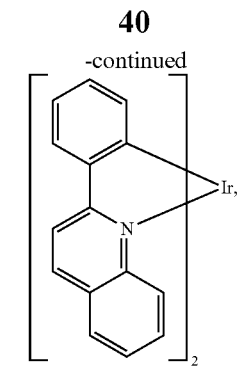
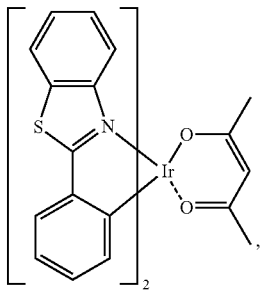
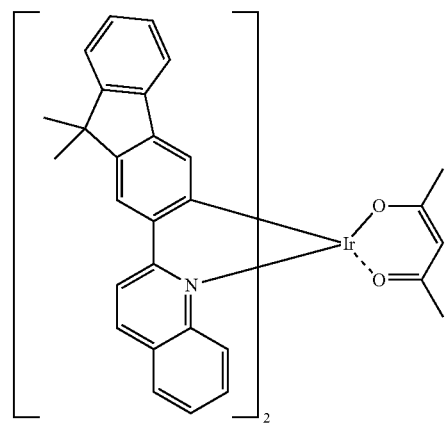
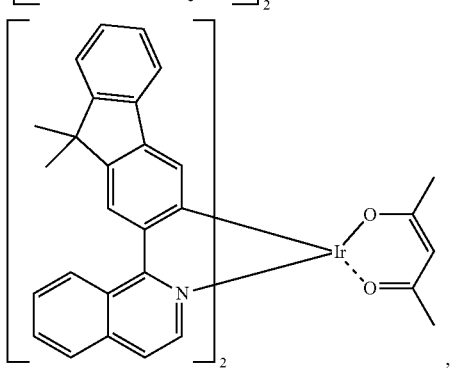
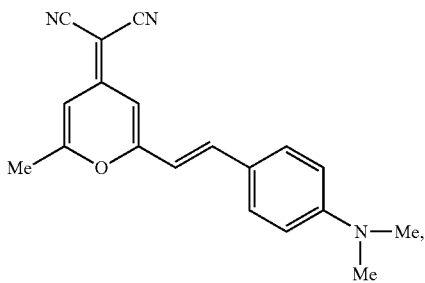

-continued
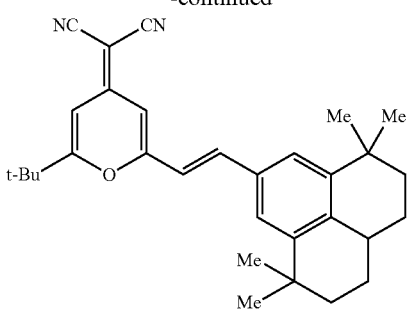
Preferably, the green doping material comprises but is not limited to one or a plurality of the following compounds:
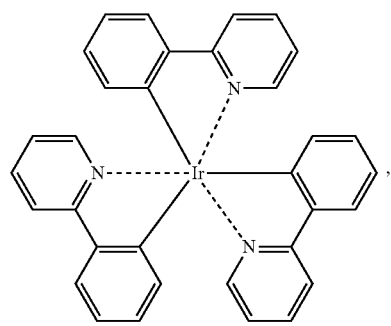
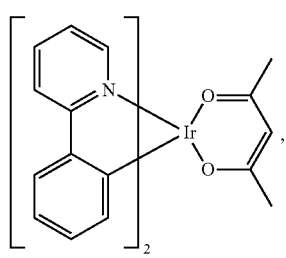
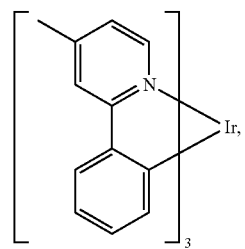
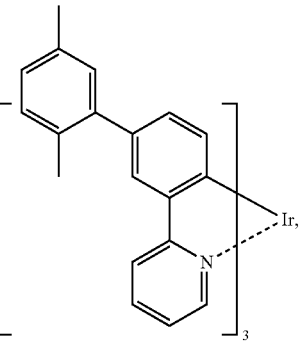
-continued
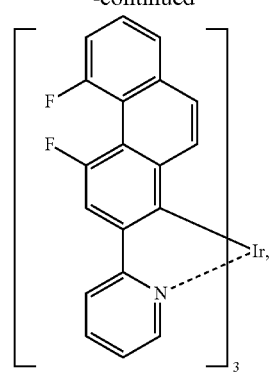
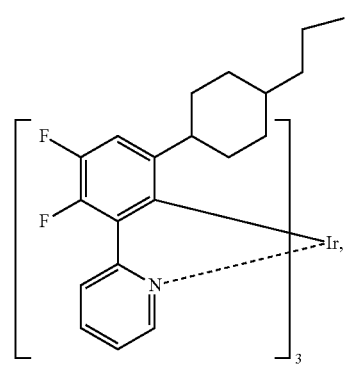
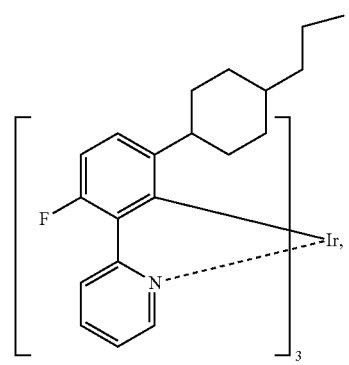
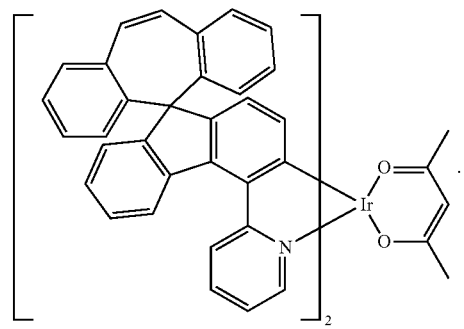
Preferably, the material of the electron transport layer further comprises but is not limited to one or a plurality of the following compounds:

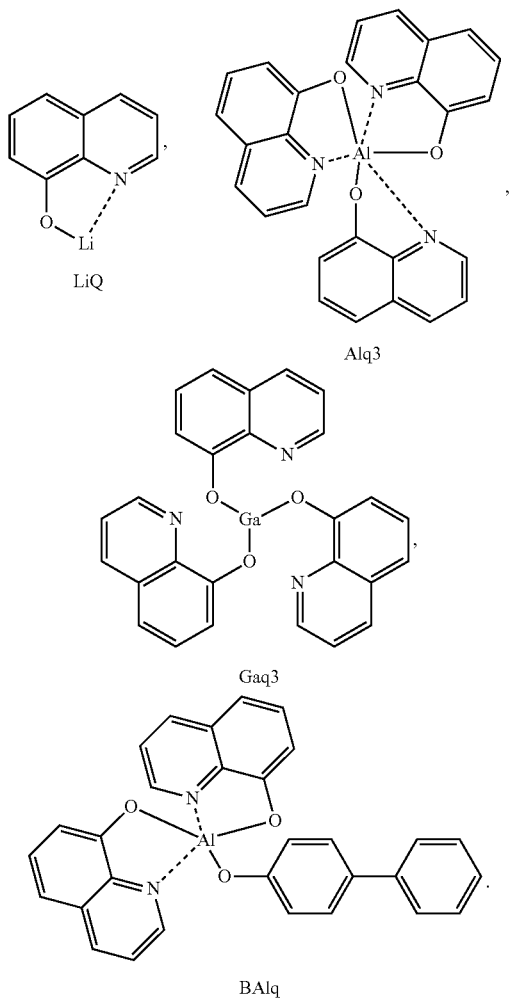

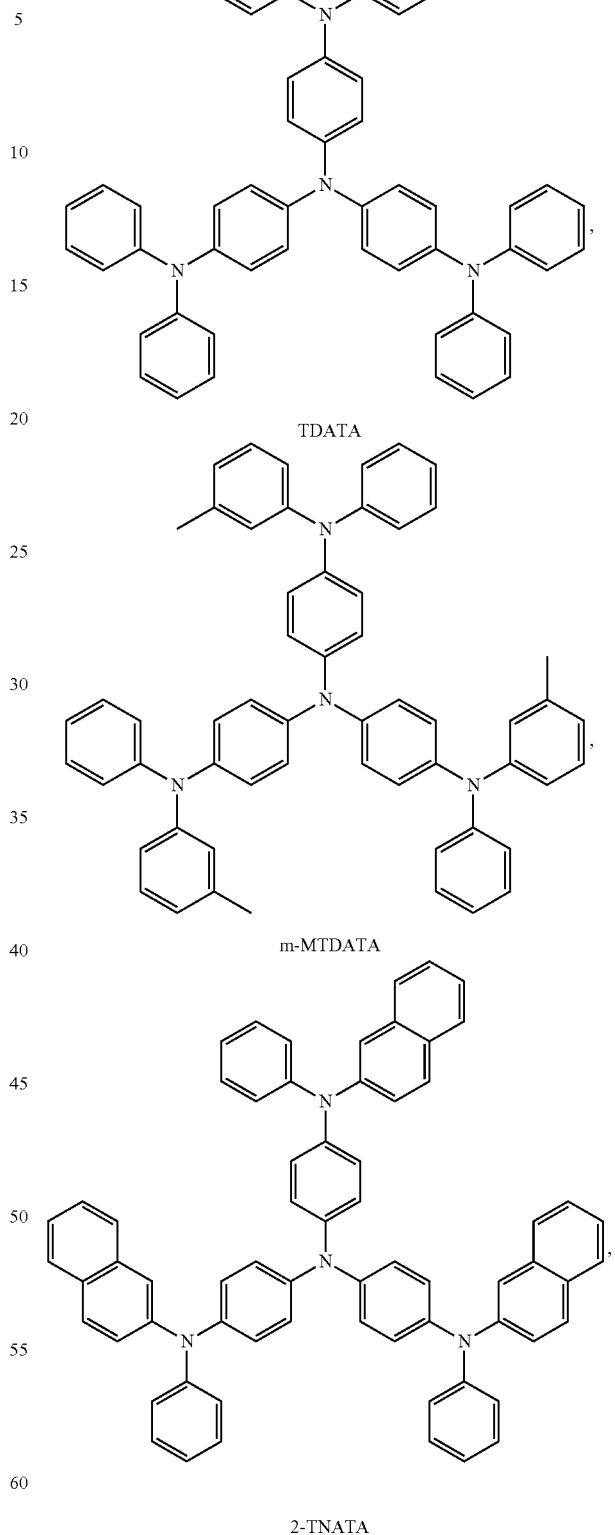

Preferably, the material of the cathode layer is selected from any one of or an alloy formed by any two of or a fluoride of the following elements: lithium, magnesium, silver, calcium, strontium, aluminum, indium, copper, gold, and silver.

Preferably, a hole injection layer is further disposed between the anode layer and the hole transport layer in the organic light-emitting device.

Preferably, the material of the hole injection layer comprises but is not limited to one or a plurality of the following compounds:

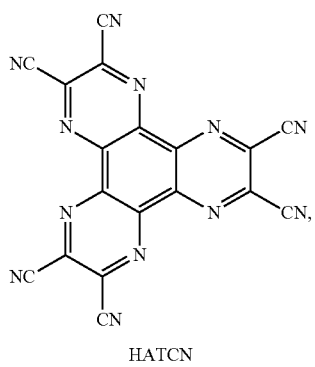

Preferably, the thickness of the hole injection layer is 30-50 nm, preferably 40 nm.

Preferably, the thickness of the hole transport layer is 5-15 nm, preferably 10 nm.

Preferably, the thickness of the organic light-emitting layer is 10-100 nm, preferably 40 nm.

Preferably, the thickness of the electron transport layer is 10-30 nm, preferably 50 nm.

Preferably, the thickness of the cathode layer is 90-110 nm, preferably 100 nm.

The present invention further provides use of an indeno-imidazole compound, comprising use in preparation of an organic light-emitting material and use in production of an organic light-emitting device.

In addition, unless otherwise specified, raw materials used in the present invention all can be obtained through commercial purchase. Any range described in the present invention comprises the end values and any value between the end values, and any sub-range formed by the end values or any values between the end values.

The present invention has the following beneficial effects:

The imidazole derivative represented by formula I and provided by the present invention has the capability of carrier transport, and the organic light-emitting device produced by using the material of the present invention has a reduced starting voltage and improved luminous efficiency and luminance. Due to the features such as relatively good film-forming performance and simple material synthesis and purification methods which are applicable to mass production, the series of imidazole derivatives are ideal options for an electron transport material of organic light-emitting devices. The use of the imidazole derivative as a light-emitting material, a host material in a light-emitting layer, a hole transport material, an electron transport material, or a hole block material also falls within the protection scope.

DESCRIPTION OF THE DRAWINGS

The specific implementations of the present invention are further described in detail below with reference to the drawings.

DETAILED DESCRIPTION OF THE PREFERRED EMBODIMENTS

Figure 1:
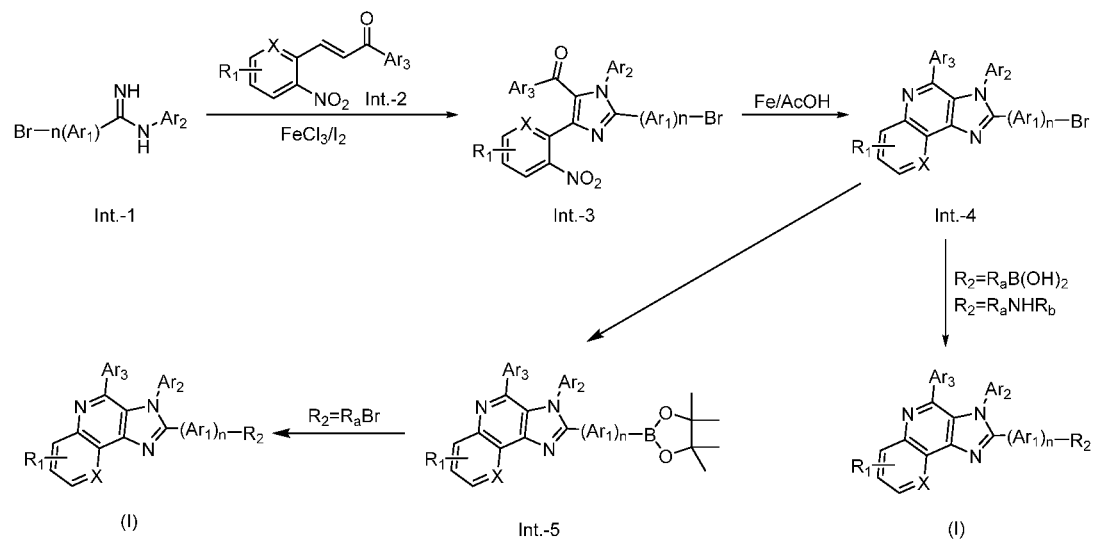
FIG. 1 illustrates a flow chart of a method for preparing a compound of formula I in the present invention.

In order to mom clearly describe the present invention, the present invention is further described below with reference to the preferred Examples and drawings. Similar components in the drawings are represented by the same reference number. A person skilled in the art should understand that the following specific description content is for description instead of for limitation, and the protection scope of the present invention shall not be limited thereto.

In the description of the present invention, unless otherwise stated, the "plurality" means two or more; the directions or positional relationships indicated by the terms "upper", "lower", et al. are based on the positions or positional relationships shown in the drawings, which are merely intended for convenience of describing the present invention and simplifying the description, but do not indicate or imply that the devices or elements referred to necessarily have a specific direction or constructed and operated in a specific direction, thus shall not be understood as a limitation to the present invention.

In the present invention, unless otherwise specified, the preparation methods are conventional methods. The used raw materials can be obtained from public commercial channels unless otherwise specified, and the percentages are mass percentages unless otherwise specified.

Test instruments and methods for performance tests of OLED materials and devices in the following examples are as follows:

Conditions for a performance test of an OLED device:

luminance and the chromaticity coordinates: tested by using a spectrum scanner PhotoResearch PR-71;

current density and turn-on voltage: tested by using a digital source meter Keithley 2420; and power efficiency: tested by using NEWPORT 1931-C.

Example 1

The structural formula of the compound CJH-P16 is as follows:

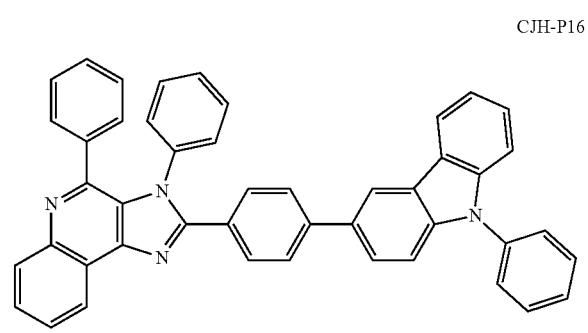 [SMILES: c1ccc(-c2nc3ccccc3c3nc(-c4ccc(-c5ccc6c(c5)c5ccccc5n6-c5ccccc5)cc4)n(-c4ccccc4)c23)cc1]

CJH-P16

A preparation route thereof is as follows:

Step 1: Preparation of an Intermediate Int.-2

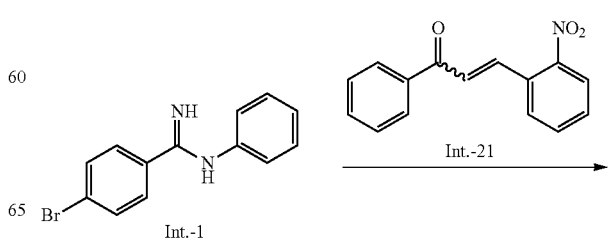

47
-continued

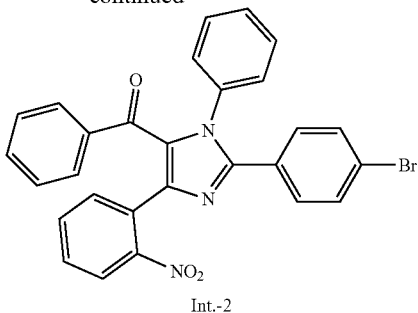
Int.-2

1.2 g of iodine and 80 ml of dichlorobenzene are added to 15 g (54.5 mmol) of 4-bromo-N-phenylbenzamidine Int.-1, 14 g (54.5 mmol) of Int.-21, and 1.5 g of anhydrous ferric chloride, oxygen is introduced, heating is performed to 110° C., stirring is performed for a reaction for 8 hours, then a mixture is cooled to room temperature and filtered, a filter cake is washed with petroleum ether, and recrystallization is performed by means of ethanol, so as to obtain 21.7 g of Int.-2 in yellow solid, with a yield of 76%.

Step 2: Preparation of an Intermediate Int.-3

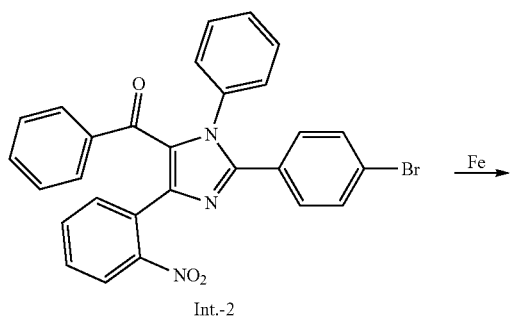

20 g (38.1 mmol) of the intermediate Int.-2 is dispersed in 150 ml of glacial acetic acid and heated to 100° C. under the protection of nitrogen, 10.6 g (0.19 mol) of iron powder is added in batches during stirring for a reaction for 1 hour, heating is performed for a reflux reaction for 10 hours, then a mixture is cooled to room temperature and filtered, a filtrate is decompression-concentrated to dryness, and separation and purification are performed by means of a silica gel column, so as to obtain 15.2 g of Int.-3 in yellow solid, with a yield of 84%.

48
Step 3: Preparation of the Compound CJH-P16

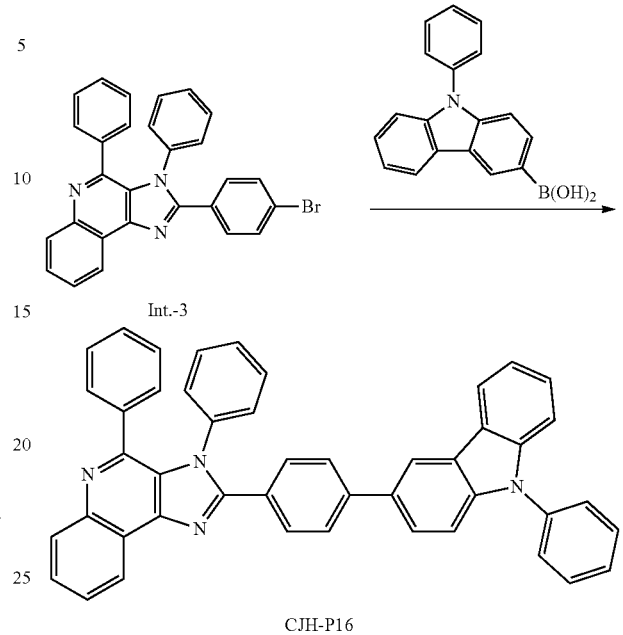

Figure 3:
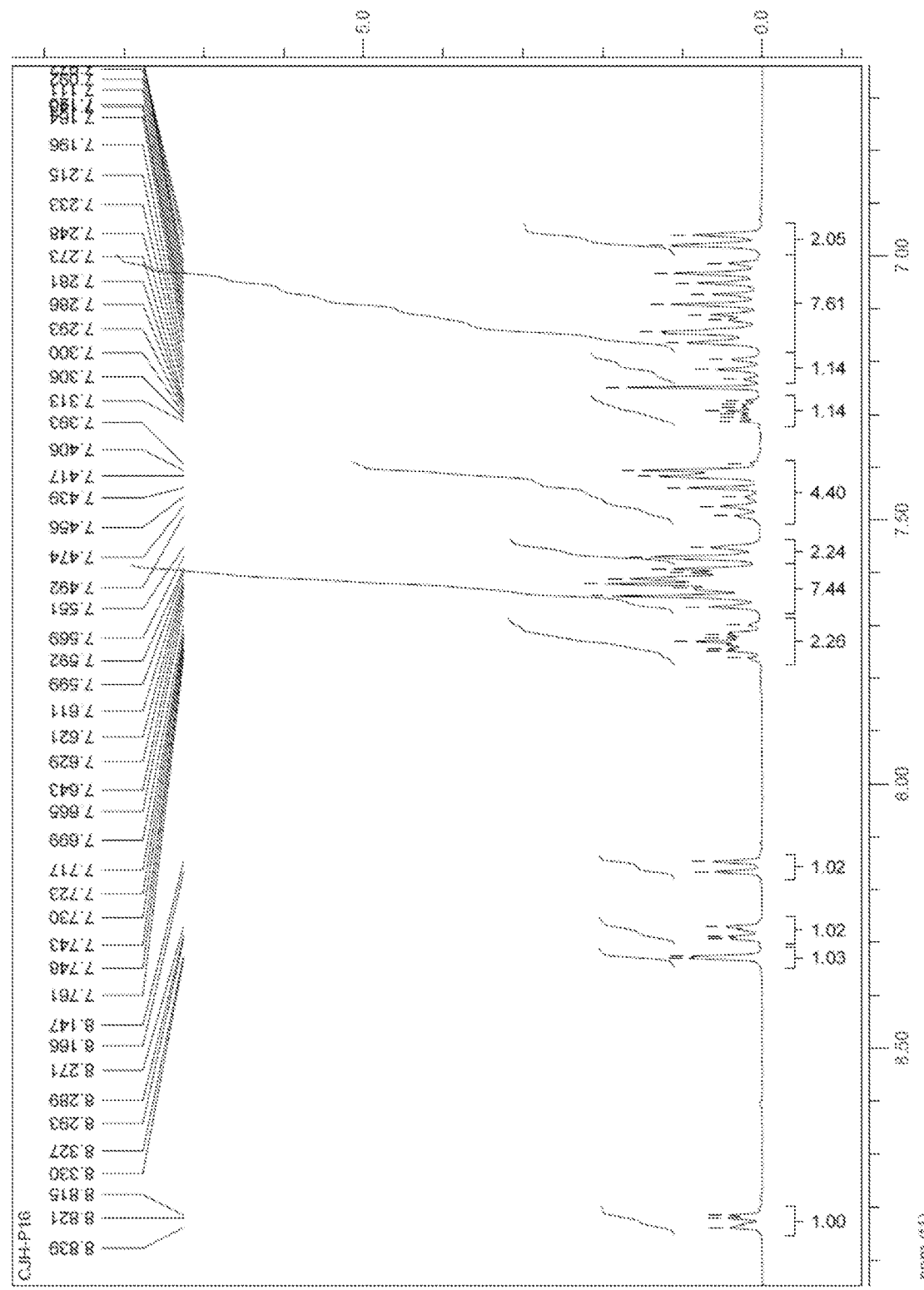
FIG. 3 illustrates a $^1$H-NMR spectrum of the compound of formula CJH-P16 in Example 1 of the present invention.
Figure 4:
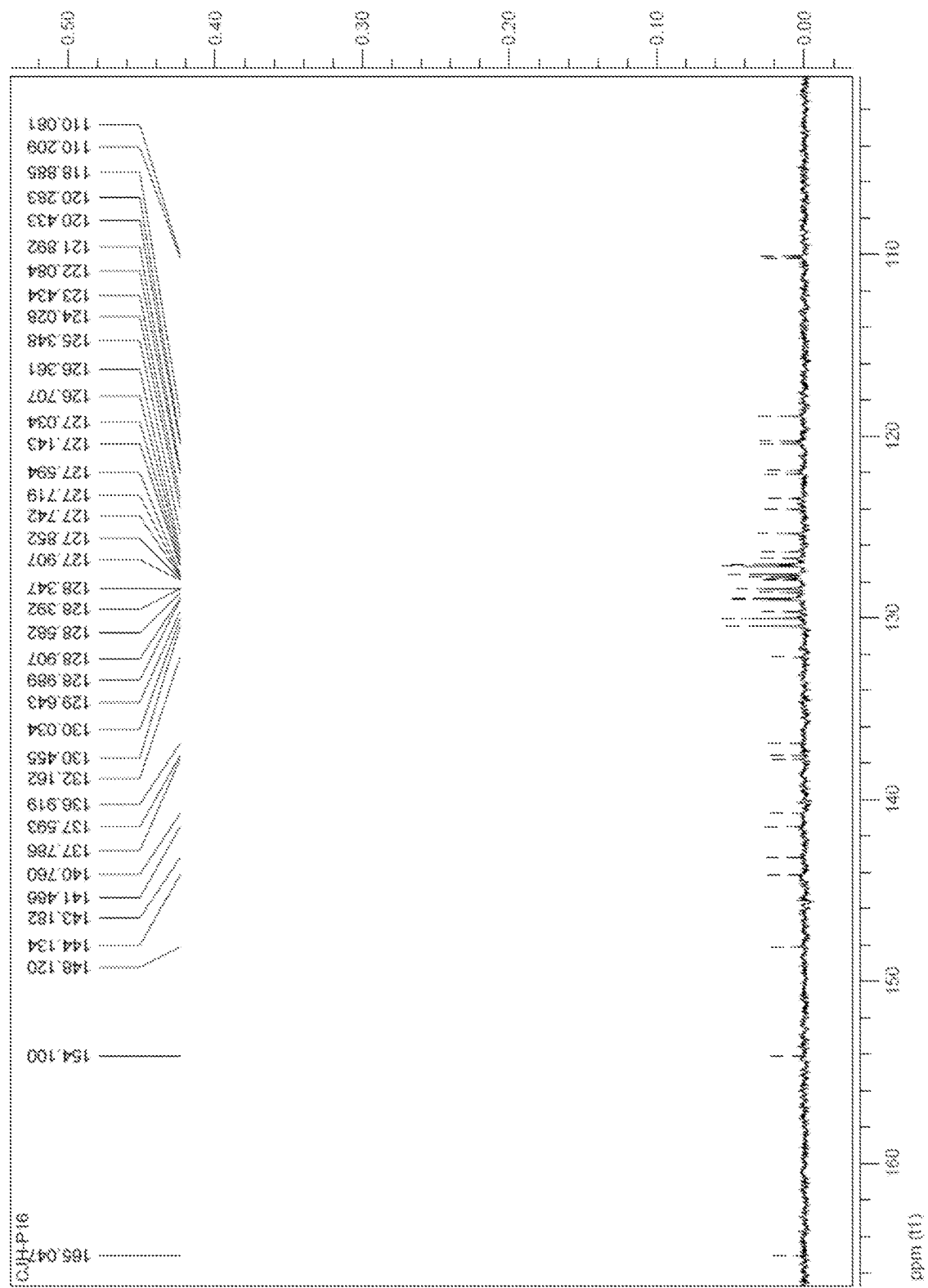
FIG. 4 illustrates a $^{13}$C-NMR spectrum of the compound of formula CJH-P16 in Example 1 of the present invention.
Figure 5:
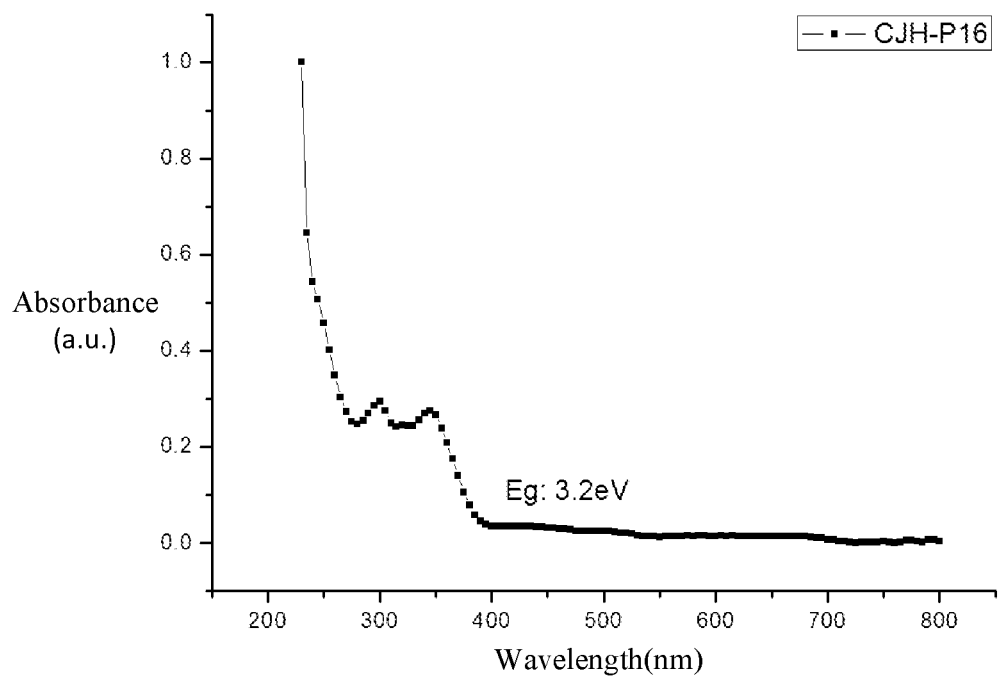
FIG. 5 illustrates a visible-ultraviolet absorption spectrum of the compound of formula CJH-P16 in Example 1 of the present invention.
Figure 6:
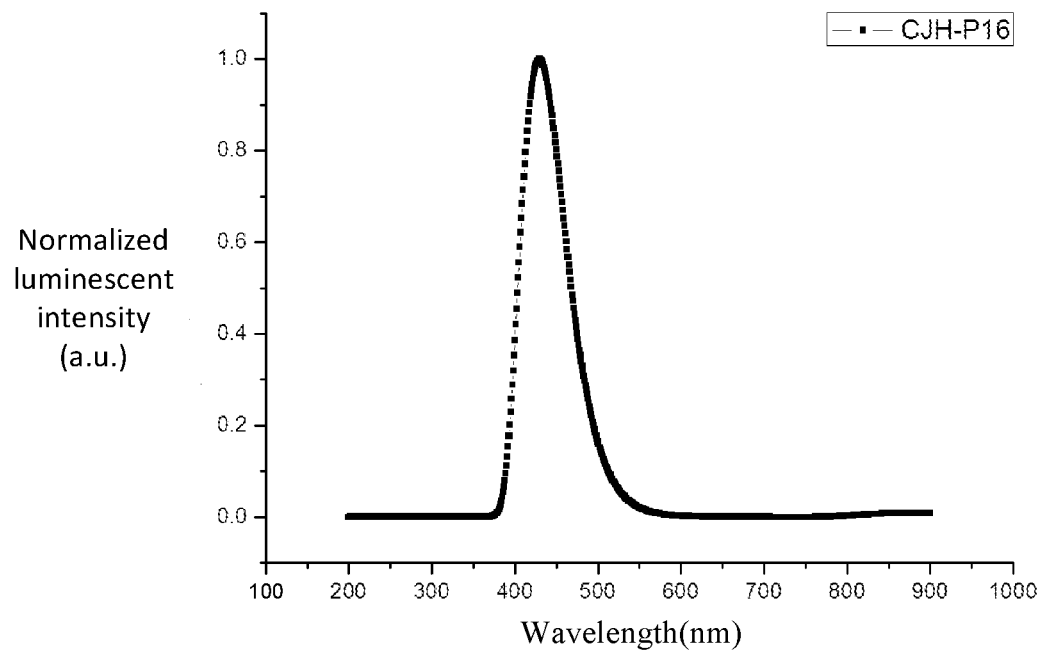
FIG. 6 illustrates a fluorescent spectrum of the compound of formula CJH-P16 in Example 1 of the present invention.

40 mL of toluene, 10 mL of ethanol, and 5 mL of water are added to 5 g (10.5 mmol) of the intermediate Int.-3, 3.6 g (12.6 mmol) of 9-phenyl-9H-carbazole-3-boronic acid, 4.5 g (42 mmol) of sodium carbonate, and 5 mg of a $Pd(PPh_3)_4$ catalyst, heating is performed for refluxing, stirring is performed for a reaction for 12 hours, then a mixture is cooled to room temperature, extraction is performed by means of ethyl acetate, an organic phase is dried and filtered, a filtrate is decompression-concentrated to dryness, and separation and purification are performed by means of a silica gel column, hot refluxing is performed by means of ethanol, and filtering is performed while the heat remains, so as to obtain 5.9 g of CJH-P16 in yellow solid, with a yield of 88%. With HRMS $C_{46}H_{30}N_4$, a standard molecular weight 638.247, and a test result 639.2562, for nuclear magnetic $^1$HNMR and $^{13}$CNMR, reference is made to FIGS. 3 and 4, and for a visible-ultraviolet absorption spectrum and a fluorescent spectrum, reference is made to FIGS. 5 and 6.

The following compounds are prepared with reference to the synthetic method of Example 1, that is, the method steps are the same as those in Example 1, except that a different compound is used to replace the 9-phenyl-9H-carbazole-3-boronic acid in step 3 of Example 1 according to actual needs so as to obtain a different desired product, and the mass amount of the compound is changed according to the molar amount. The results are shown in Table 1:

TABLE 1

Mass spectrum test results and carrier mobility of different compounds

| Serial number | Compound No. | Mass spectrum test result | Carrier mobility ($cm^2/VS$) |
|---|---|---|---|
| 1 | CJH-P01 | 755.2932 | $7.6 \times 10^{-5}$ |
| 2 | CJH-P02 | 727.2915 | $4.8 \times 10^{-5}$ |
| 3 | CJH-P03 | 754.2979 | $5.5 \times 10^{-5}$ |
| 4 | CJH-P04 | 744.3131 | $5.9 \times 10^{-5}$ |
| 5 | CJH-P05 | 627.2553 | $5.3 \times 10^{-5}$ |
| 6 | CJH-P06 | 700.2765 | $4.4 \times 10^{-5}$ |

TABLE 1-continued

Mass spectrum test results and carrier mobility of different compounds

| Serial number | Compound No. | Mass spectrum test result | Carrier mobility (cm$^2$/VS) |
|---|---|---|---|
| 7 | CJH-P07 | 700.2762 | $5.2 \times 10^{-5}$ |
| 8 | CJH-P08 | 675.2557 | $5.7 \times 10^{-5}$ |
| 9 | CJH-P09 | 690.2554 | $7.8 \times 10^{-5}$ |
| 10 | CJH-P10 | 728.2716 | $4.7 \times 10^{-5}$ |
| 11 | CJH-P11 | 712.2761 | $4.4 \times 10^{-5}$ |
| 12 | CJH-P12 | 714.2918 | $5.5 \times 10^{-5}$ |
| 13 | CJH-P13 | 652.2508 | $6.4 \times 10^{-5}$ |
| 14 | CJH-P14 | 639.2553 | $3.4 \times 10^{-5}$ |
| 15 | CJH-P15 | 666.2664 | $6.2 \times 10^{-5}$ |
| 16 | CJH-P16 | 639.2562 | $3.7 \times 10^{-5}$ |
| 17 | CJH-P17 | 693.2778 | $5.8 \times 10^{-5}$ |
| 18 | CJH-P18 | 693.2776 | $7.4 \times 10^{-5}$ |
| 19 | CJH-P19 | 674.2928 | $5.5 \times 10^{-5}$ |
| 20 | CJH-P20 | 705.2775 | $8.4 \times 10^{-5}$ |
| 21 | CJH-P21 | 704.2822 | $5.8 \times 10^{-5}$ |
| 22 | CJH-P22 | 728.2821 | $7.3 \times 10^{-5}$ |
| 23 | CJH-P23 | 716.2710 | $3.5 \times 10^{-5}$ |
| 24 | CJH-P24 | 728.2824 | $6.7 \times 10^{-5}$ |
| 25 | CJH-P25 | 629.2463 | $5.5 \times 10^{-5}$ |
| 26 | CJH-P26 | 628.2512 | $8.6 \times 10^{-5}$ |
| 27 | CJH-P27 | 552.2203 | $7.2 \times 10^{-5}$ |
| 28 | CJH-P28 | 630.2415 | $6.9 \times 10^{-5}$ |
| 29 | CJH-P29 | 732.2847 | $5.2 \times 10^{-5}$ |
| 30 | CJH-P30 | 674.2378 | $5.8 \times 10^{-5}$ |
| 31 | CJH-P31 | 667.2624 | $6.8 \times 10^{-5}$ |
| 32 | CJH-P32 | 641.2719 | $5.5 \times 10^{-5}$ |
| 33 | CJH-P81 | 716.2825 | $7.1 \times 10^{-5}$ |
| 34 | CJH-P83 | 748.2765 | $6.3 \times 10^{-5}$ |
| 35 | CJH-P84 | 880.3453 | $4.0 \times 10^{-5}$ |
| 36 | CJH-P88 | 639.2556 | $4.5 \times 10^{-5}$ |
| 37 | CJH-P99 | 739.2874 | $4.1 \times 10^{-5}$ |

Example 2

The structural formula of the compound CJH-P37 is as follows:

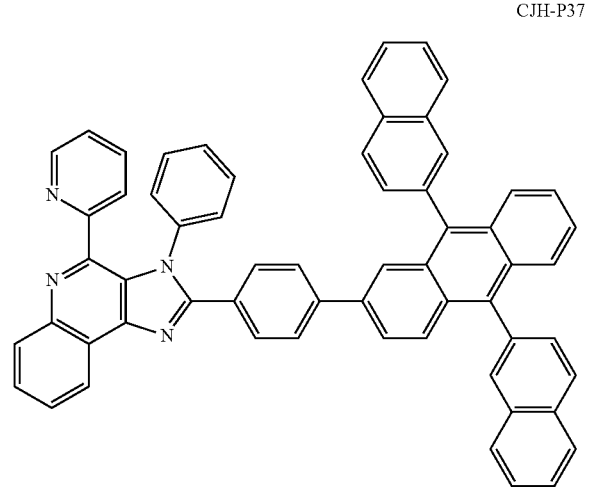 [SMILES: c1ccc(-n2c(-c3ccc(-c4ccc5c(-c6ccc7ccccc7c6)c6ccccc6c(-c6ccc7ccccc7c6)c5c4)cc3)nc3c4ccccc4nc(-c4ccccn4)c32)cc1]

CJH-P37

A preparation route thereof is as follows:

Step 1: Preparation of an Intermediate Int.-4

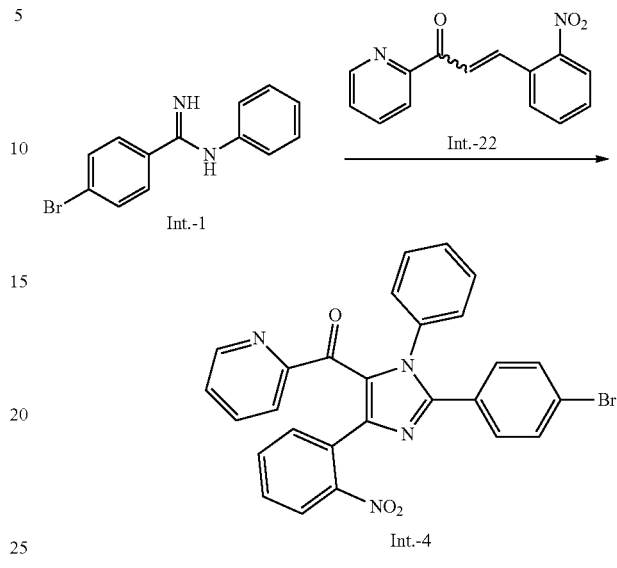

For a synthetic operation, reference is made to step 1 of Example 1, wherein Int.-21 in step 1 of Example 1 is replaced with Int.-22 (3-(2-nitrophenyl)-1-(2-pyridyl)propyl-2-en-1-one), so as to obtain the intermediate Int.-4 in yellow solid, with a yield of 88%.

Step 2: Preparation of an Intermediate Int.-5

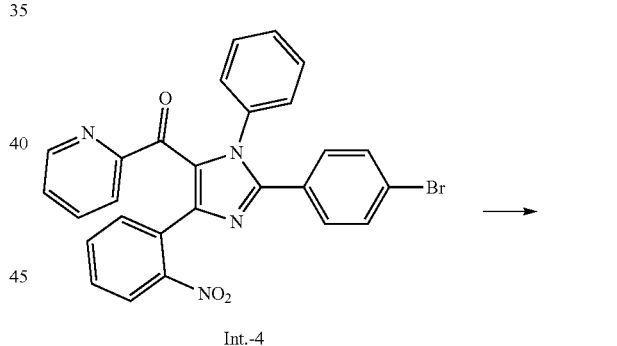

Int.-4

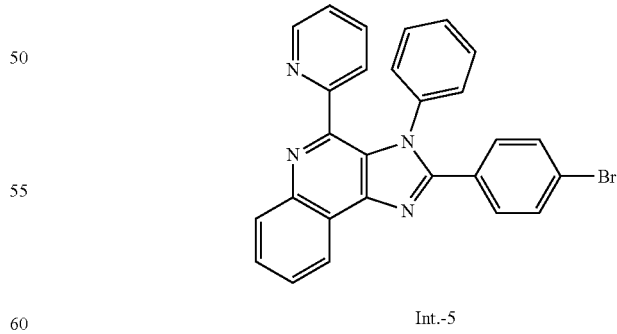

Int.-5

For a synthetic operation, reference is made to step 2 of Example 1, wherein the intermediate Int.-2 in step 2 of Example 1 is replaced with the intermediate Int.-4, so as to obtain the intermediate Int.-5 in white solid, with a yield of 90%.

Step 3: Preparation of an Intermediate Int.-6

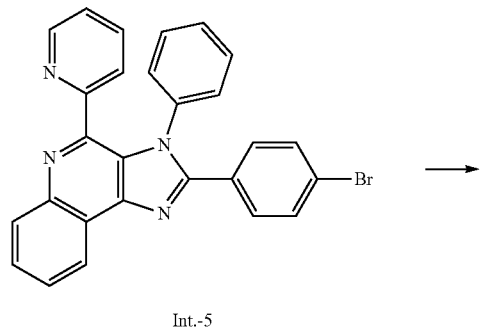

Int.-5

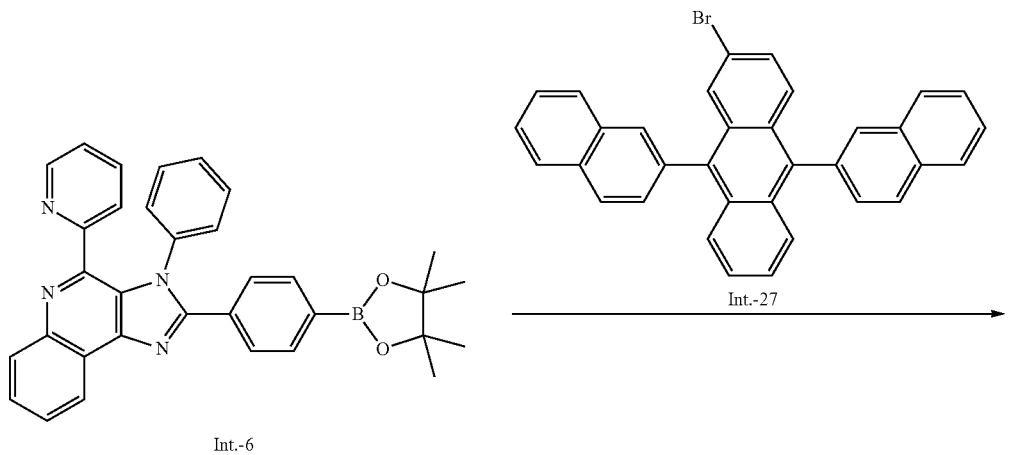

Int.-6

10 g (20.9 mmol) of the intermediate Int.-5, 6.4 g (25 mmol) of bis(pinacolate)diboron, and 3.0 g (31.4 mmol) of potassium acetate are mixed, then 54 mg of a $PdCl_2(dppf)$ $CH_2Cl_2$ catalyst and 80 mL of N,N-dimethylformamide are added, heating is performed under the protection of nitrogen to 90° C., stirring is performed for a reaction for 12 hours, then a mixture is cooled to room temperature, poured into ice water, and filtered, a filter cake is washed with water, and separation and purification are performed by means of a silica gel column, so as obtain 10 g of Int.-6 in white solid, with a yield of 92%.

Step 4: Preparation of the Compound CJH-P37

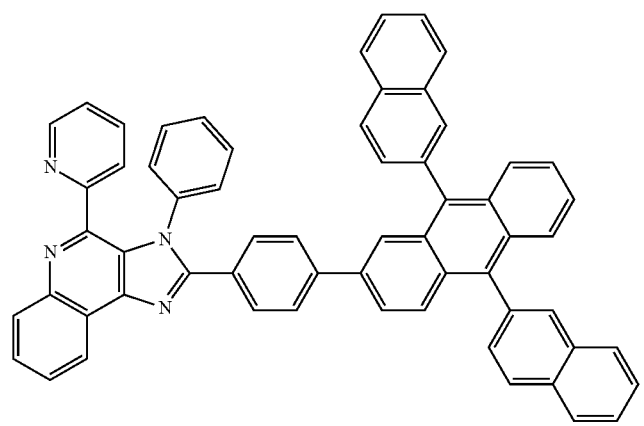

CJH-P37

Figure 7:
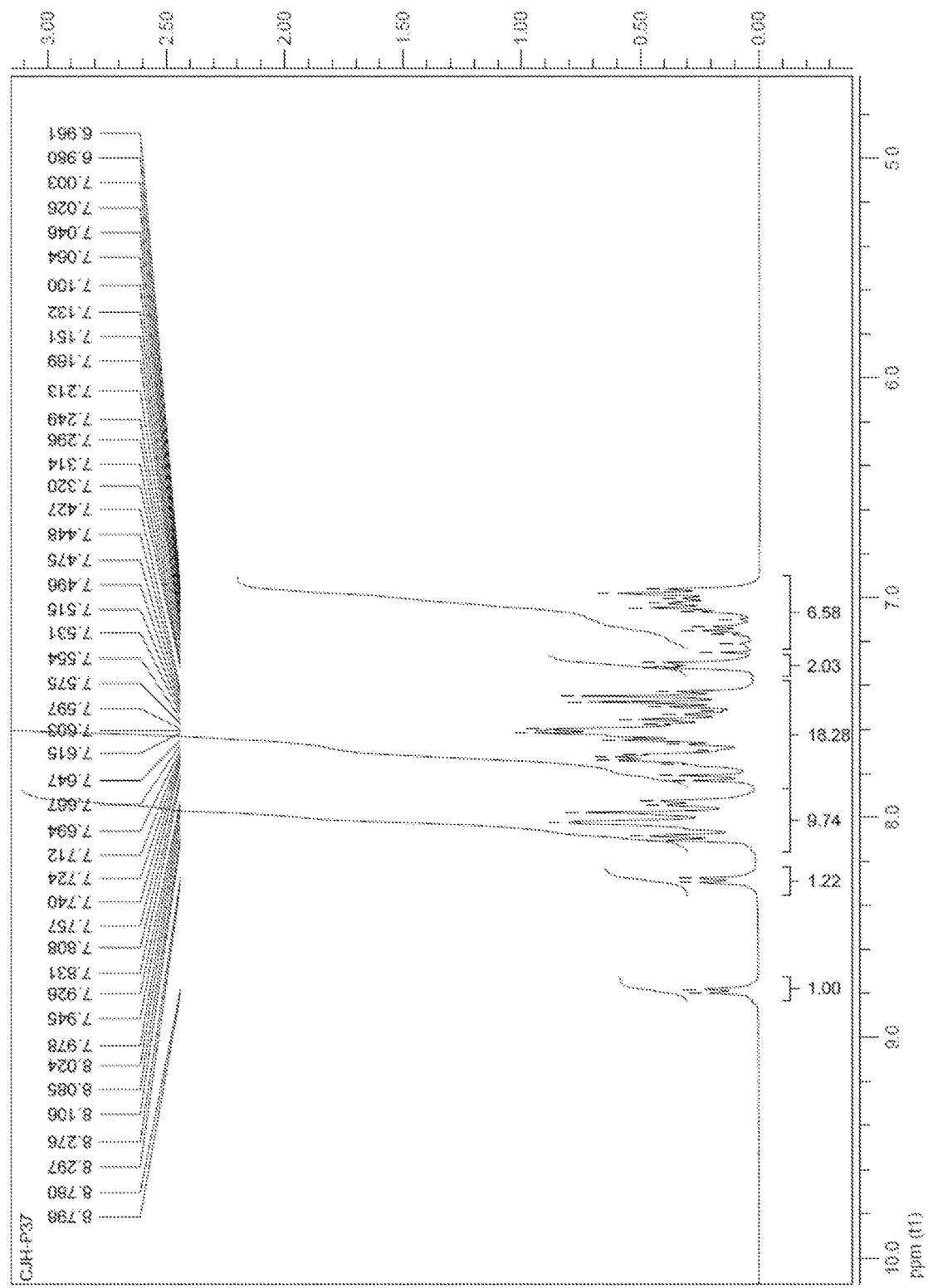
FIG. 7 illustrates a $^1$H-NMR spectrum of the compound of formula CJH-P37 in Example 2 of the present invention.
Figure 8:
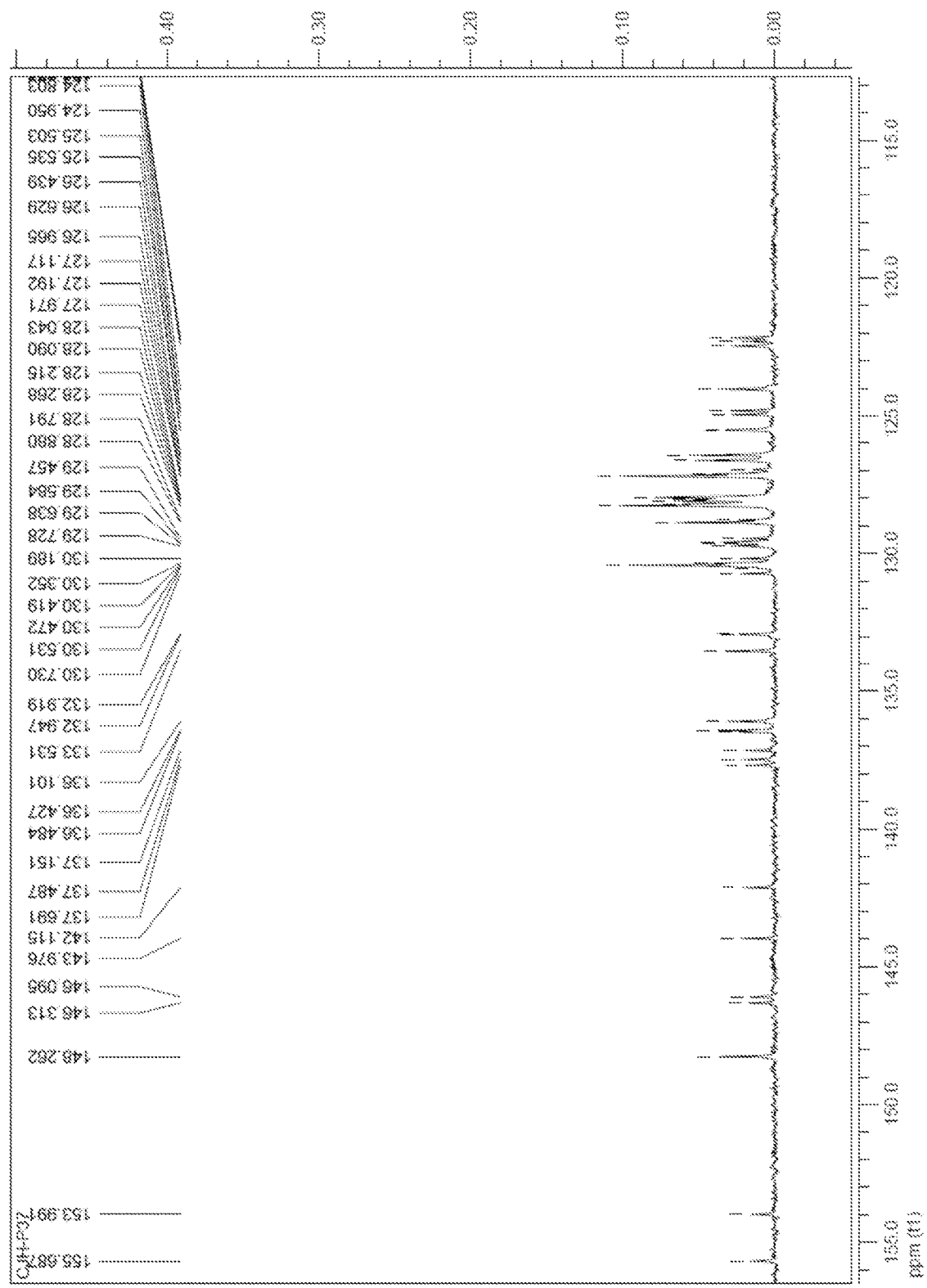
FIG. 8 illustrates a $^{13}$C-NMR spectrum of the compound of formula CJH-P37 in Example 2 of the present invention.
Figure 9:
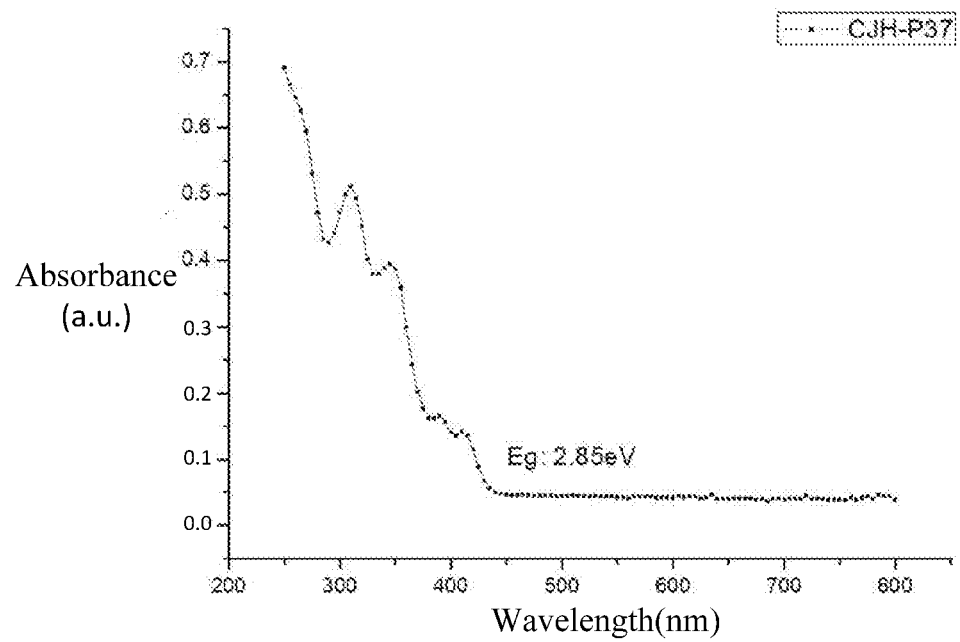
FIG. 9 illustrates a visible-ultraviolet absorption spectrum of the compound of formula CJH-P37 in Example 2 of the present invention.
Figure 10:
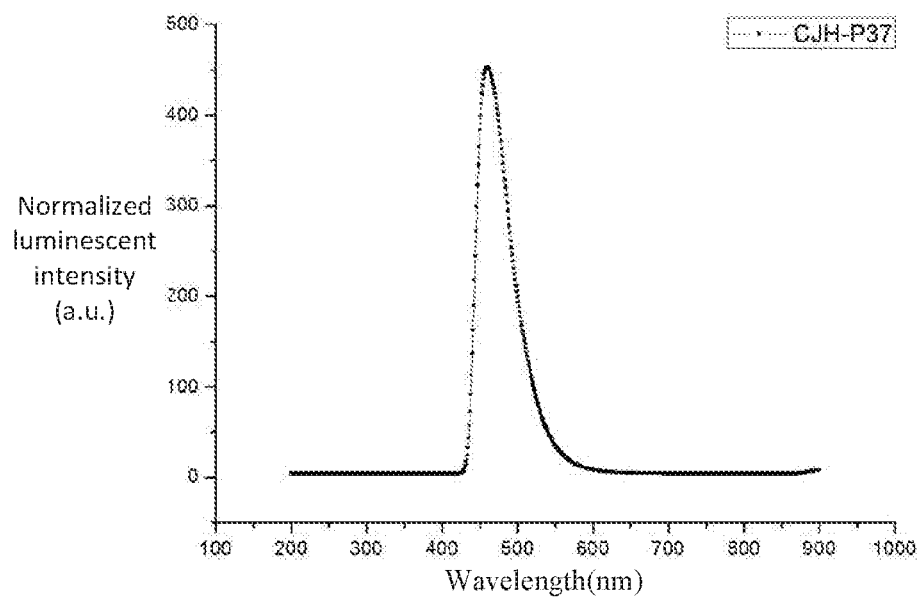
FIG. 10 illustrates a fluorescent spectrum of the compound of formula CJH-P37 in Example 2 of the present invention.

40 mL of toluene, 10 mL of ethanol, and 5 mL of water are added to 5 g (9.5 mmol) of the intermediate Int.-6, 4.4 g (8.6 mmol) of Int.-27, 3.7 g (34.9 mmol) of sodium carbonate, and 5 mg of a Pd(PPh$_3$)$_4$ catalyst, heating is performed for refluxing, stirring is performed for a reaction for 12 hours, then a mixture is cooled to room temperature, extraction is performed by means of ethyl acetate, an organic phase is dried and filtered, a filtrate is decompression-concentrated to dryness, separation and purification are performed by means of a silica gel column, heating is performed to boiling by means of ethanol, and then filtering is performed while the heat remains, so as to obtain 4.9 g of CJH-P37 in yellow solid, with a yield of 68.5%. With HRMS C$_{61}$H$_{38}$N$_4$, a standard molecular weight 826.3096, and a test result 827.3182, for nuclear magnetic $^1$HNMR and $^{13}$CNMR, reference is made to FIGS. 7 and 8, and for a visible-ultraviolet absorption spectrum and a fluorescent spectrum, reference is made to FIGS. 9 and 10.

The following compounds are prepared with reference to the synthetic method of Example 2, that is, the method steps are the same as those in Example 2, except that a different compound is used to replace the Int.-27 in step 4 of Example 2 according to actual needs so as to obtain a different desired product, and the mass amount of the compound is changed according to the molar amount. The results are shown in Table 2:

TABLE 2

Mass spectrum test results and carrier mobility of different compounds

| Serial number | Compound No. | Mass spectrum test result | Carrier mobility (cm$^2$/VS) |
|---|---|---|---|
| 38 | CJH-P35 | 705.2776 | 8.6 × 10$^{-5}$ |
| 39 | CJH-P36 | 701.2715 | 7.6 × 10$^{-5}$ |
| 40 | CJH-P37 | 827.3182 | 5.3 × 10$^{-5}$ |
| 41 | CJH-P38 | 745.3092 | 6.4 × 10$^{-5}$ |
| 42 | CJH-P39 | 716.2822 | 8.3 × 10$^{-5}$ |
| 43 | CJH-P40 | 839.3502 | 4.4 × 10$^{-4}$ |
| 44 | CJH-P41 | 837.3356 | 4.7 × 10$^{-4}$ |
| 45 | CJH-P42 | 795.2994 | 5.8 × 10$^{-5}$ |
| 46 | CJH-P43 | 806.2935 | 9.6 × 10$^{-5}$ |
| 47 | CJH-P44 | 675.2323 | 6.8 × 10$^{-5}$ |
| 48 | CJH-P82 | 717.2773 | 8.4 × 10$^{-5}$ |

Example 3

The structural formula of the compound CJH-P50 is as follows:

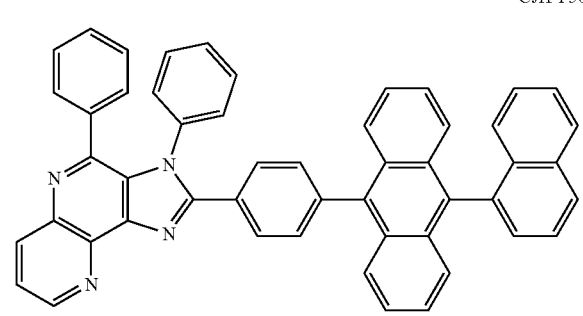

CJH-P50

A preparation route thereof is as follows:

Step 1: Preparation of an Intermediate Int.-7

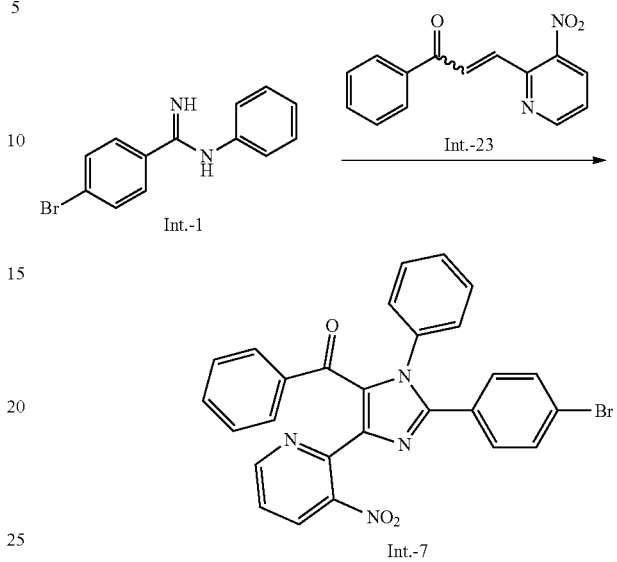

For a synthetic operation, reference is made to step 1 of Example 1, wherein Int.-21 in step 1 of Example 1 is replaced with an intermediate Int.-23, so as to obtain the intermediate Int.-7 in yellow solid, with a yield of 56%.

Step 2: Preparation of an Intermediate Int.-8

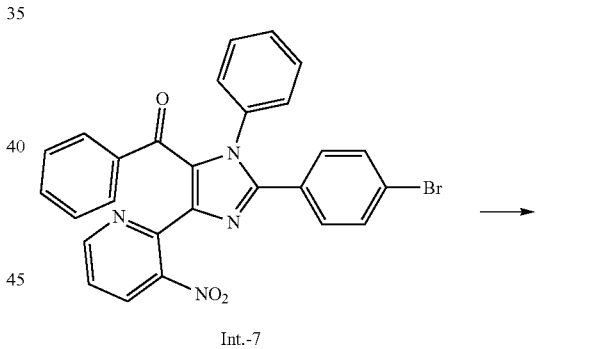

Int.-7

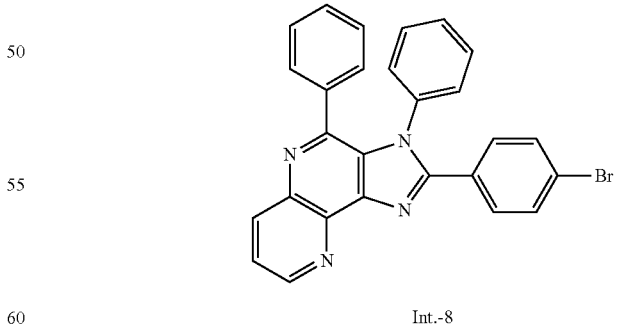

Int.-8

For a synthetic operation, reference is made to step 2 of Example 1, wherein the Int.-2 in step 2 of Example 1 is replaced with the Int.-7, so as to obtain the intermediate Int.-8 in yellow solid, with a yield of 87%.

Step 3: Preparation of an Intermediate Int.-9
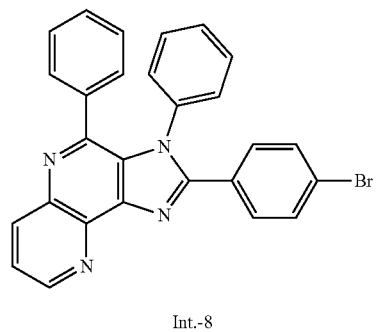 
Int.-8
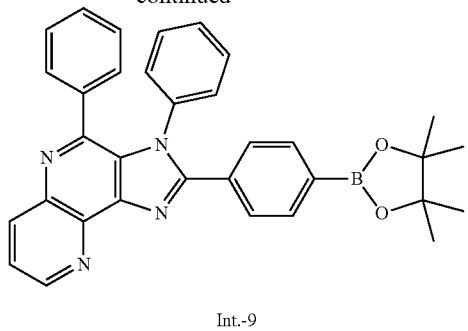
Int.-9
For a synthetic operation, reference is made to step 3 of Example 2, wherein the Int.-5 in step 3 of Example 2 is replaced with the Int.-8, so as to obtain the intermediate Int.-9 in yellow solid, with a yield of 92%.
Step 4: Preparation of the Compound CJH-P50
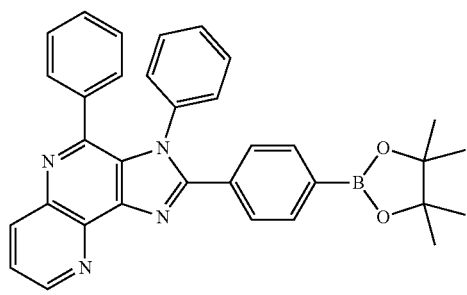  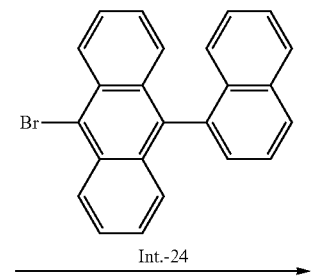
Int.-9

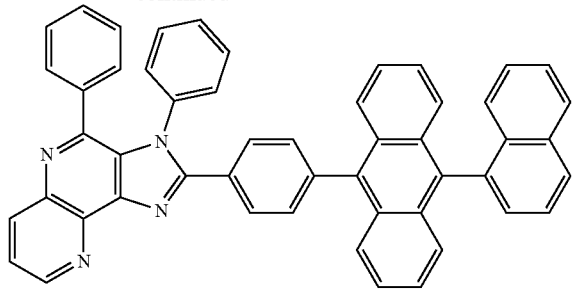

CJH-P50

40 mL of toluene, 10 mL of ethanol, and 5 mL of water are added to 5 g (9.5 mmol) of the intermediate Int.-9, 3.3 g (8.6 mmol) of Int.-24, 3.7 g (34.9 mmol) of sodium carbonate, and 5 mg of a Pd(PPh$_3$)$_4$ catalyst, heating is performed for refluxing, stirring is performed for a reaction for 12 hours, then a mixture is cooled to room temperature, extraction is performed by means of ethyl acetate, an organic phase is dried and filtered, a filtrate is decompression-concentrated to dryness, separation and purification are performed by means of a silica gel column, heating is performed to boiling by means of ethyl acetate, and then filtering is performed while the heat remains, so as to obtain 4.0 g of CJH-P50 in white solid, with a yield of 66%. The HRMS is $C_{51}H_{32}N_4$, a standard molecular weight is 700.2627, a test result is 701.2714, $^1$HNMR (δ, CDCl3) is as follows: 8.89-8.86 (1H, m); 8.32-8.30 (1H, m); 8.06-7.99 (2H, m); 7.80-7.65 (8H, m); 7.55-7.41 (7H, m); 8.35-7.29 (2H, m); 7.26-7.13 (6H, m); and 7.10-7.02 (5H, m). The carrier mobility is $5.8 \times 10^{-4}$ cm$^2$/VS.

The following compounds are prepared with reference to the synthetic method of Example 3, that is, the method steps are the same as those in Example 3, except that a different compound is used to replace the Int.-24 in step 4 of Example 3 according to actual needs so as to obtain a different desired product, and the mass amount of the compound is changed according to the molar amount. The results are shown in Table 3:

TABLE 3

Mass spectrum test results and carrier mobility of different compounds

| Serial number | Compound No. | Mass spectrum test result | Carrier mobility (cm$^2$/VS) |
|---|---|---|---|
| 49 | CJH-P45 | 756.2887 | $8.8 \times 10^{-5}$ |
| 50 | CJH-P46 | 727.2874 | $6.4 \times 10^{-5}$ |
| 51 | CJH-P47 | 755.2936 | $7.4 \times 10^{-5}$ |
| 52 | CJH-P48 | 745.3088 | $6.6 \times 10^{-5}$ |
| 53 | CJH-P49 | 628.2512 | $6.7 \times 10^{-5}$ |
| 54 | CJH-P50 | 701.2714 | $5.8 \times 10^{-4}$ |
| 55 | CJH-P51 | 701.2716 | $6.4 \times 10^{-5}$ |
| 56 | CJH-P52 | 676.2515 | $6.2 \times 10^{-5}$ |
| 57 | CJH-P53 | 681.2662 | $6.0 \times 10^{-5}$ |
| 58 | CJH-P54 | 729.2664 | $7.2 \times 10^{-5}$ |
| 59 | CJH-P55 | 707.3186 | $5.6 \times 10^{-5}$ |
| 60 | CJH-P56 | 713.2714 | $6.7 \times 10^{-5}$ |
| 61 | CJH-P57 | 715.2875 | $6.9 \times 10^{-5}$ |
| 62 | CJH-P58 | 653.2466 | $4.2 \times 10^{-5}$ |
| 63 | CJH-P59 | 640.2512 | $5.8 \times 10^{-5}$ |
| 64 | CJH-P60 | 667.2621 | $4.2 \times 10^{-4}$ |
| 65 | CJH-P61 | 640.2513 | $5.5 \times 10^{-5}$ |
| 66 | CJH-P62 | 694.2724 | $8.6 \times 10^{-5}$ |
| 67 | CJH-P63 | 694.2726 | $5.2 \times 10^{-4}$ |
| 68 | CJH-P64 | 675.2885 | $3.7 \times 10^{-4}$ |
| 69 | CJH-P65 | 706.2724 | $7.5 \times 10^{-5}$ |
| 70 | CJH-P66 | 705.2774 | $4.4 \times 10^{-4}$ |
| 71 | CJH-P67 | 729.2776 | $8.2 \times 10^{-5}$ |
| 70 | CJH-P68 | 717.2665 | $7.1 \times 10^{-5}$ |
| 73 | CJH-P69 | 729.2774 | $6.3 \times 10^{-4}$ |
| 74 | CJH-P70 | 630.2414 | $3.0 \times 10^{-4}$ |
| 75 | CJH-P71 | 629.2462 | $8.4 \times 10^{-5}$ |
| 76 | CJH-P72 | 553.2153 | $7.6 \times 10^{-5}$ |
| 77 | CJH-P73 | 693.2525 | $7.2 \times 10^{-5}$ |
| 78 | CJH-P74 | 733.2794 | $8.0 \times 10^{-5}$ |
| 79 | CJH-P75 | 675.2322 | $8.8 \times 10^{-5}$ |
| 80 | CJH-P76 | 668.2572 | $5.2 \times 10^{-4}$ |
| 81 | CJH-P77 | 642.2665 | $6.6 \times 10^{-5}$ |
| 82 | CJH-P80 | 717.2772 | $6.2 \times 10^{-4}$ |
| 83 | CJH-P100 | 679.2618 | $8.6 \times 10^{-5}$ |

Example 4

The structural formula of the compound CJH-P87 is as follows:

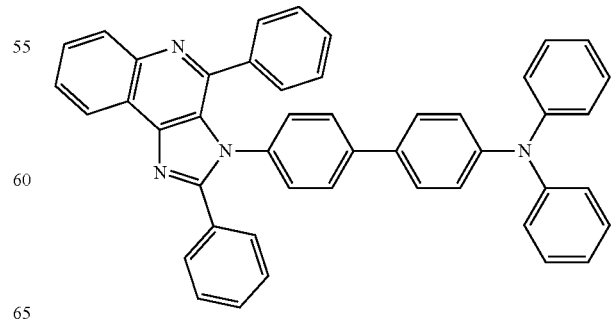

CJH-P87

A preparation route thereof is as follows:
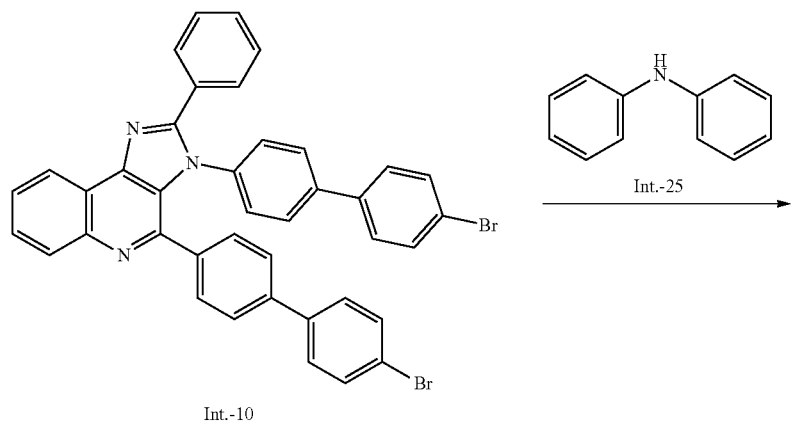
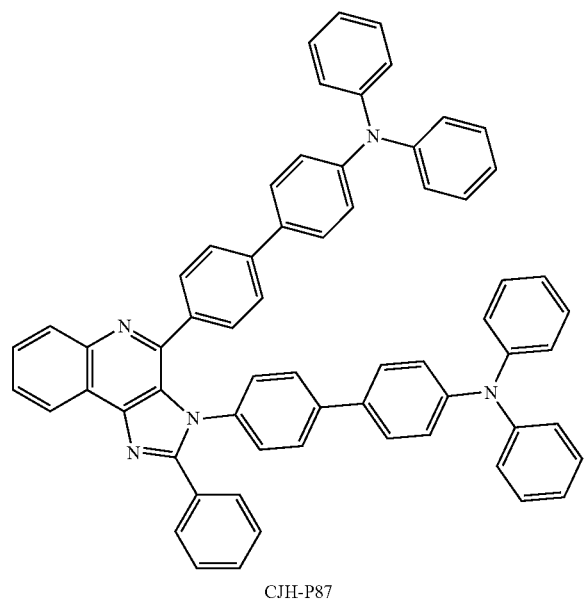

5 g (7.0 mmol) of an intermediate Int.-40, 2.6 g (15.5 mmol) of diphenylamine, and 2.0 g (21.2 mmol) of sodium tert-butoxide are mixed, then 73 mg (0.08 mmol) of a Pd2(dba)3 catalyst and 80 mL of toluene are added, 0.2 mL of a 10% tri-tert-butyl phosphorus toluene solution is added under the protection of nitrogen, heating is performed to 90° C., stirring is performed for a reaction for 16 hours, then a mixture is cooled to room temperature. 80 mL of water is added to separate an organic phase, an aqueous phase is extracted by means of ethyl acetate, the organic phase is dried by means of anhydrous sodium sulfate and filtered, a filtrate is decompression-concentrated to dryness, and separation and purification are performed by means of a silica gel column, so as to obtain 4.7 g of white solid, with a yield of 76%. The HRMS is $C_{64}H_{45}N_5$, a standard molecular weight is 883.3675, a test result is 884.3762, $^1$HNMR (δ, CDCl3) is as follows: 8.81-8.79 (1H, m); 8.30-8.28 (1H, d); 7.76-7.69 (2H, m); 7.60-7.59 (2H, d); 7.37-7.12 (22H, m); and 7.08-6.93 (17H, m). The carrier mobility is $6.4 \times 10^{-5}$ cm$^2$/VS.

Example 5

The structural formula of the compound CJH-P98 is as follows:

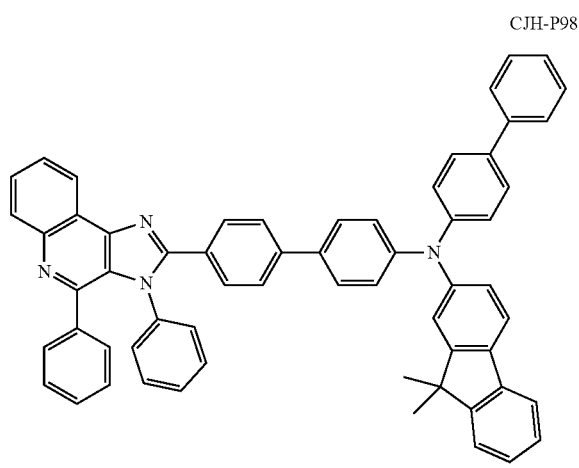 [SMILES: CC1(C)c2ccccc2-c2ccc(N(c3ccc(-c4ccccc4)cc3)c3ccc(-c4ccc(-c5nc6c7ccccc7nc(-c7ccccc7)c6n5-c5ccccc5)cc4)cc3)cc21]

CJH-P98

A preparation route thereof is as follows:

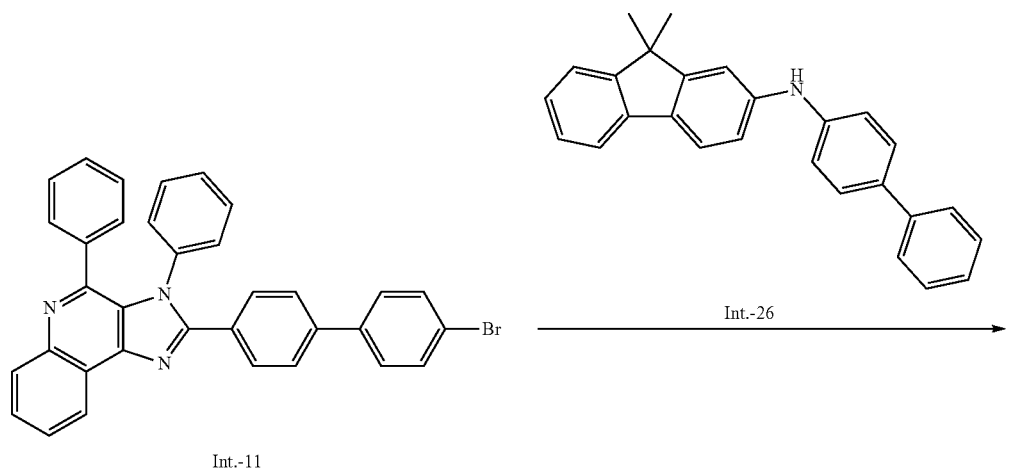

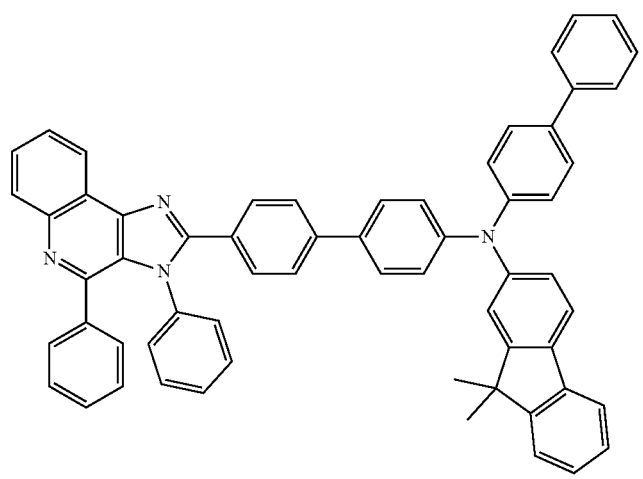

CJH-P98

5 g (9.0 mmol) of an intermediate Int.-11, 3.0 g (8.5 mmol) of an intermediate Int.-26, and 1.2 g (12.75 mmol) of sodium tert-butoxide are mixed, then 73 mg (0.08 mmol) of a Pd2(dba)3 catalyst and 80 mL of toluene are added. 0.2 mL of a 10% tri-tert-butyl phosphorus toluene solution is added under the protection of nitrogen, heating is performed to 90° C., stirring is performed for a reaction for 16 hours, then a mixture is cooled to room temperature, 80 mL of water is added for filtering, a filter cake is washed with water and ethanol, and separation and purification are performed by means of a silica gel column, so as to obtain 4.5 g of white solid, with a yield of 64%. The HRMS is $C_{61}H_{44}N_4$, a standard molecular weight is 832.3566, a test result is 833.3653, $^1$HNMR (δ, CDCl3) is as follows: 8.33-8.29 (1H, m); 7.76-7.71 (2H, m); 7.49-7.44 (2H, m); 7.31-7.16 (27H, m); 7.12-7.01 (5H, m); 6.99-6.96 (1H, d); and 1.41 (6H, s). The carrier mobility is $5.8\times10^{-5}$ cm$^2$/VS.

The following compounds are prepared with reference to the synthetic method of Example 5, that is, the method steps are the same as those in Example 5, except that a different compound is used to replace the Int.-26 in Example 5 according to actual needs so as to obtain a different desired product, and the mass amount of the compound is changed according to the molar amount. The results are shown in Table 4:

| Mass spectrum test results and carrier mobility of different compounds | | | |
|---|---|---|---|
| Serial number | Compound No. | Mass spectrum test result | Carrier mobility (cm$^2$/VS) |
| 84 | CJH-P33 | 804.3135 | $4.7 \times 10^{-5}$ |
| 85 | CJH-P34 | 893.3402 | $5.0 \times 10^{-5}$ |
| 86 | CJH-P78 | 805.3092 | $4.5 \times 10^{-5}$ |
| 87 | CJH-P79 | 894.3354 | $6.0 \times 10^{-5}$ |
| 88 | CJH-P85 | 656.2822 | $5.2 \times 10^{-5}$ |
| 89 | CJH-P86 | 630.2304 | $5.5 \times 10^{-5}$ |
| 90 | CJH-P87 | 884.3762 | $6.4 \times 10^{-5}$ |
| 91 | CJH-P89 | 564.2192 | $5.9 \times 10^{-5}$ |
| 92 | CJH-P90 | 654.2664 | $7.7 \times 10^{-5}$ |
| 93 | CJH-P91 | 793.3342 | $5.6 \times 10^{-5}$ |
| 94 | CJH-P92 | 922.3922 | $4.2 \times 10^{-5}$ |
| 95 | CJH-P93 | 922.3920 | $3.8 \times 10^{-5}$ |
| 96 | CJH-P94 | 1029.4653 | $8.5 \times 10^{-5}$ |
| 97 | CJH-P95 | 762.3242 | $7.7 \times 10^{-5}$ |
| 98 | CJH-P96 | 782.3294 | $7.5 \times 10^{-5}$ |
| 99 | CJH-P97 | 899.3874 | $5.5 \times 10^{-4}$ |
| 100 | CJH-P98 | 833.3653 | $5.8 \times 10^{-5}$ |

Example 6

Figure 2:
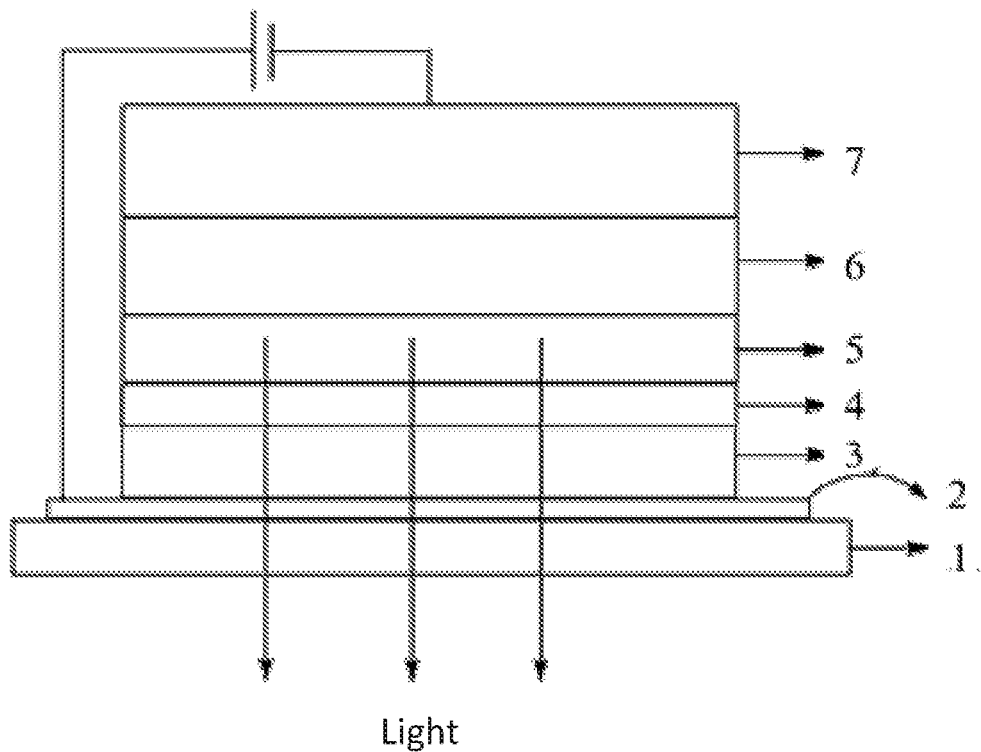
FIG. 2 illustrates a schematic structural diagram of an OLED device in Example 6 of the present invention, with a substrate 1, an anode layer 2, a hole injection layer 3, a hole transport layer 4, an organic light-emitting layer 5, an electron transport layer 6, and a cathode layer 7.

An organic light-emitting device, which is a bottom-emitting device, has a structure as shown in FIG. 2 and comprises a substrate 1, an anode layer 2 disposed on the substrate 1, a hole injection layer 3 disposed on the anode layer 2, a hole transport layer 4 disposed on the hole injection layer 3, an organic light-emitting layer 5 disposed on the hole transport layer 4, an electron transport layer 6 disposed on the organic light-emitting layer 5, and a cathode layer 7 disposed on the electron transport layer 6, wherein the preparation thereof comprises the following steps:

1) the glass substrate coated with an ITO conductive layer is sonicated in a cleaning agent for 30 minutes, washed in deionized water, sonicated in an acetone/ethanol mixed solvent for 30 minutes, baked in a clean environment to complete dryness, and irradiated with an ultraviolet cleaning machine for 10 minutes, and the surface thereof is bombarded with a low energy cation beam;

2) the treated ITO glass substrate is placed in a vacuum chamber, which is vacuumized to 1×10-5-9×10-3 Pa, and a compound 2-TNATA is evaporated on a film of the anode layer to form a hole injection layer, wherein an evaporation rate is 0.1 nm/s, and the thickness of an evaporation film is 40 nm;

3) NPB is evaporated on the hole injection layer to form a hole transport layer, wherein an evaporation rate is 0.1 nm/s, and the thickness of an evaporation film is 10 nm;

4) ADN is evaporated on the hole transport layer as a host material and DPVBi as a doping material, with the mass ratio of AND to DPVBi being 98:2, so as to form an organic light-emitting layer of the device, wherein an evaporation rate is 0.1 nm/s, and the film thickness of the organic light-emitting layer obtained by means of the evaporation is 40 nm;

5) the compound (of formula I) of the present invention is evaporated on the organic light-emitting layer as a host material and LiQ as a doping material, with the mass ratio of the compound (of formula I) to LiQ being 90:10, so as to form an electron transfer layer, wherein an evaporation rate is 0.1 nm/s, and the thickness of an evaporation film is 50 nm;

6) a magnesium/silver alloy is sequentially evaporated on the electron transfer layer to form a cathode layer of the device, wherein an evaporation rate of the magnesium/silver alloy is 2.0-3.0 nm/s, the thickness of an evaporation film is 100 nm, and the mass ratio of magnesium to silver is 1:9, so as to obtain the OLED device provided by the present invention.

An OLED-1 provided by the present invention is obtained through the same steps as described above, wherein CJH-P19 is selected as the compound (of formula I) in step 5).

An OLED-2 provided by the present invention is obtained through the same steps as described above, wherein CJH-P36 is selected as the compound (of formula I) in step 5).

An OLED-3 provided by the present invention is obtained through the same steps as described above, wherein CJH-P37 is selected as the compound (of formula I) in step 5).

An OLED-4 provided by the present invention is obtained through the same steps as described above, wherein CJH-P50 is selected as the compound (of formula I) in step 5).

An OLED-5 provided by the present invention is obtained through the same steps as described above, wherein CJH-P63 is selected as the compound (of formula I) in step 5).

A comparative OLED-6 is obtained through the same steps as described above, wherein the compound (of formula I) in step 5) is replaced with Alq3. The performance test results of the obtained devices OLED-1 to OLED-6 are shown in Table 5.

TABLE 5

| Performance test results of OLED-1 to OLED-6 | | | | | | | |
|---|---|---|---|---|---|---|---|
| Device No. | Material | Turn-on Voltage (V) | Current density (mA/cm$^2$) | Luminance (Cd/m$^2$) | Current efficiency (Cd/A) | Emission color | Half life (hour) |
| OLED-1 | CJH-P19 | 4.6 | 50 | 3018 | 6.03 | Blue | 455 |
| OLED-2 | CJH-P36 | 4.2 | 50 | 3092 | 6.18 | Blue | 483 |
| OLED-3 | CJH-P37 | 4.8 | 50 | 3037 | 6.07 | Blue | 474 |
| OLED-4 | CJH-P50 | 4.3 | 50 | 3478 | 6.94 | Blue | 486 |

TABLE 5-continued

Performance test results of OLED-1 to OLED-6

| Device No. | Material | Turn-on Voltage (V) | Current density (mA/cm$^2$) | Luminance (Cd/m$^2$) | Current efficiency (Cd/A) | Emission color | Half life (hour) |
|---|---|---|---|---|---|---|---|
| OLED-5 | CJH-P63 | 4.2 | 50 | 3332 | 6.65 | Blue | 505 |
| OLED-6 | Alq3 | 7.8 | 50 | 1564 | 3.12 | Blue | 114 |

It can be known from the above that the device produced by using the organic material of the present invention has a low turn-on voltage, and in the case of the same current density, the luminance and efficiency are significantly higher than the case where Alq3 is used to form an electron transport layer, and the half-life of the device is much longer.

Apparently, the above-described examples of the present invention are merely illustrations for clear description of the present invention instead of limitation to the implementation manners of the present invention, a person skilled in the art can further make other variations or modifications of different forms on the basis of the above description, all of the implementation manners cannot be listed herein, and any obvious variations or modifications derived from the technical solutions of the present invention still fall within the protection scope of the present invention.

What is claimed is:

1. An imidazole derivative, wherein the structural formula of the imidazole derivative is as represented by formula I:

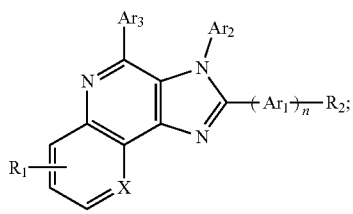

I wherein $R_1$ and $R_2$ respectively and independently represent hydrogen, deuterium, a $C_1$-$C_8$ linear or branched alkyl group, a $C_1$-$C_8$ linear or branched alkoxy group, a substituted or unsubstituted $C_6$-$C_{60}$ aryl group, a substituted or unsubstituted $C_6$-$C_{60}$ aryl vinyl group, a substituted or unsubstituted $C_{10}$-$C_{60}$ fused-ring aryl group, a substituted or unsubstituted $C_6$-$C_{60}$ arylamine group, a substituted or unsubstituted $C_{10}$-$C_{60}$ nitrogen atom-containing fused-ring aryl group, a substituted or unsubstituted $C_{10}$-$C_{60}$ sulfur or oxygen atom-containing fused-ring aryl group, a substituted or unsubstituted $C_{10}$-$C_{60}$ phosphorus, silicon, or boron atom-containing fused-ring aryl group, or a substituted or unsubstituted $C_2$-$C_{60}$ heterocyclic aryl group;

$Ar_1$, $Ar_2$, and $Ar_3$ respectively and independently represent a substituted or unsubstituted phenyl group, a substituted or unsubstituted naphthyl group, a substituted or unsubstituted fluorenyl group, a substituted or unsubstituted spirofluorenyl group, a substituted or unsubstituted anthryl group, a substituted or unsubstituted pyridyl group, a substituted or unsubstituted pyrimidyl group, a substituted or unsubstituted quinolyl group, a substituted or unsubstituted carbazolyl group, or a substituted or unsubstituted $C_2$-$C_{60}$ heterocyclic aryl group;

n represents an integer of 1-5; and x represents —CH or a nitrogen atom.

2. The imidazole derivative according to claim 1, wherein in the $R_1$, $R_2$, $Ar_1$, $Ar_2$, and $Ar_3$ groups, the $C_2$-$C_{60}$ heterocyclic aryl groups are respectively and independently selected from one or a plurality of the following structures of formulas II-1 to II-15:

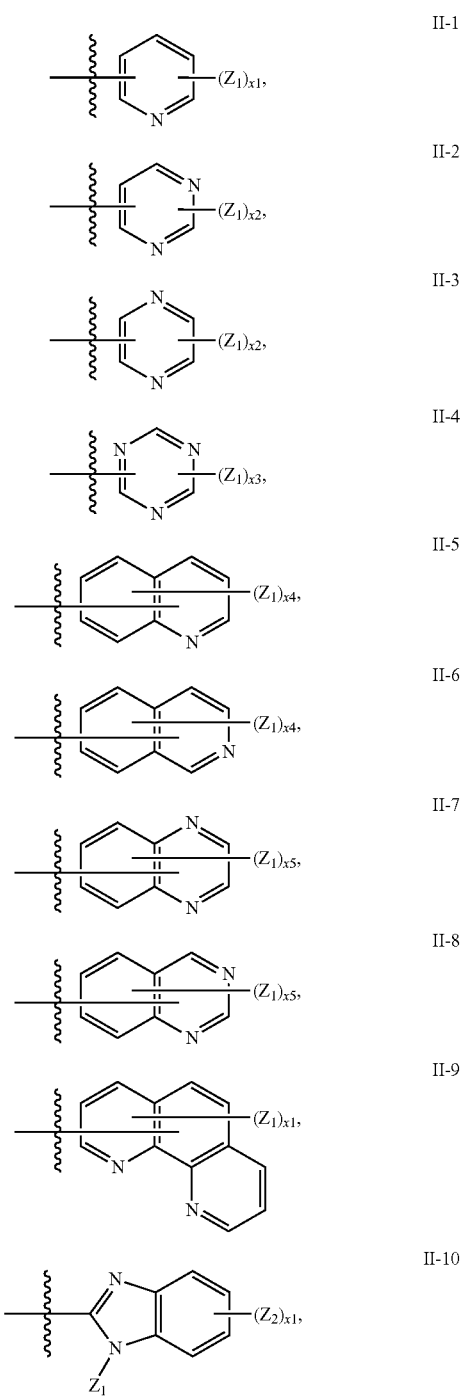

-continued

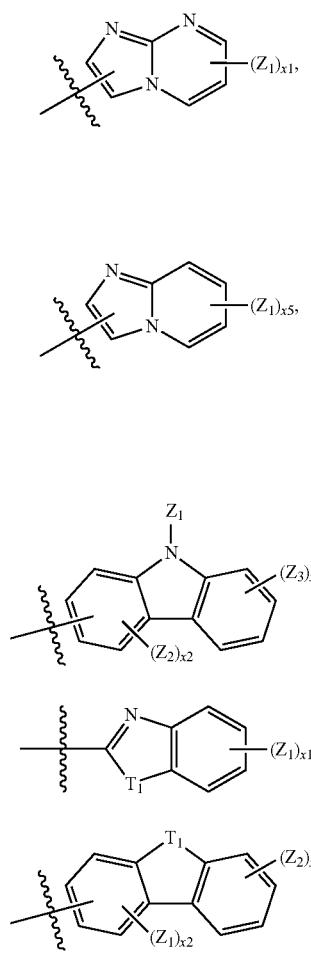

wherein $Z_1$, $Z_2$, and $Z_3$ respectively and independently represent hydrogen, deuterium, a halogen atom, a hydroxyl group, a nitrile group, a nitro group, an amino group, an amidine group, a hydrazine group, a hydrazone group, a carboxyl group or a carboxylate thereof, a sulfonic group or a sulfonate thereof, a phosphate group or a phosphate thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkane group, a $C_3$-$C_{60}$ cycloolefin group, a $C_6$-$C_{60}$ aryl group, a $C_6$-$C_{60}$ aryl group containing at least one of —F, —CN, or a $C_1$-$C_{10}$ alkyl group, a substituted or unsubstituted $C_6$-$C_{60}$ aryloxy group, a substituted or unsubstituted $C_6$-$C_{60}$ aryl thioether group, or a substituted or unsubstituted $C_2$-$C_{60}$ heterocyclic aryl group;

x1 represents an integer of 1-4; x2 represents an integer of 1-3; x3 represents an integer of 1 or 2; x4 represents an integer of 1-6; x5 represents an integer of 1-5;

$T_1$ represents an oxygen atom or a sulfur atom; and

∽∽∽ represents a bond between a substituent and a main structure.

3. The imidazole derivative according to claim 1, wherein the structural formula of the compound having a structural formula I is specifically represented by the following formulas CJH-P01 to CJH-P100:

-continued
CJH-P06
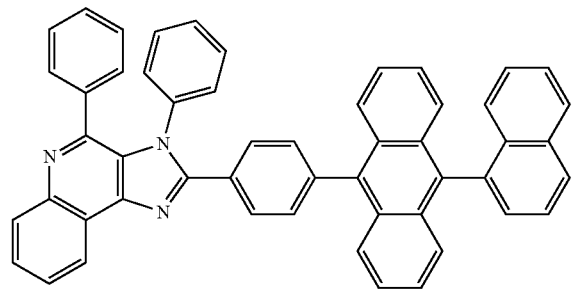
CJH-P07
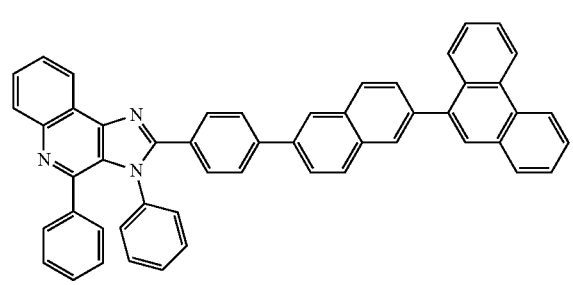
CJH-P08
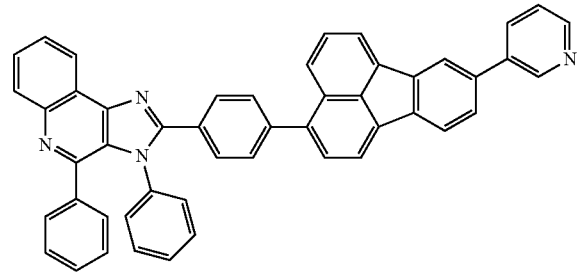
CJH-P09
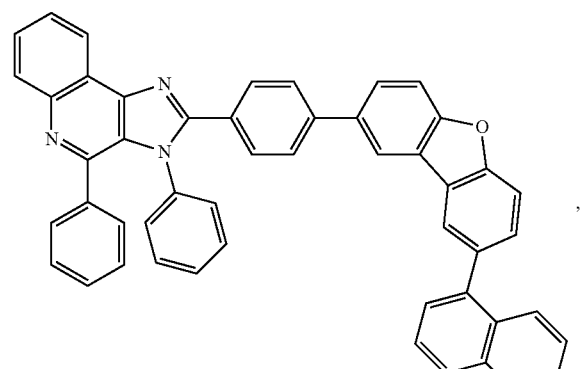
CJH-P10
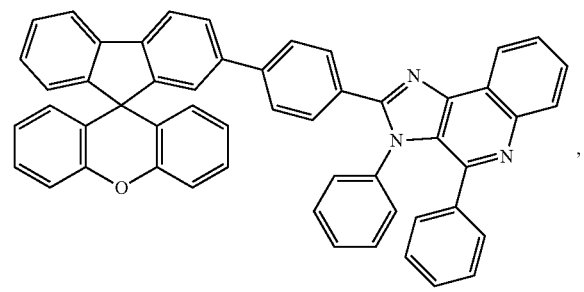
-continued
CJH-P11
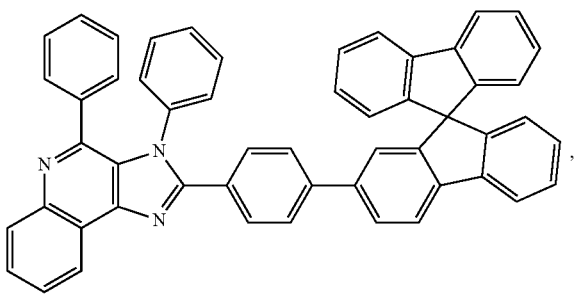
CJH-P12
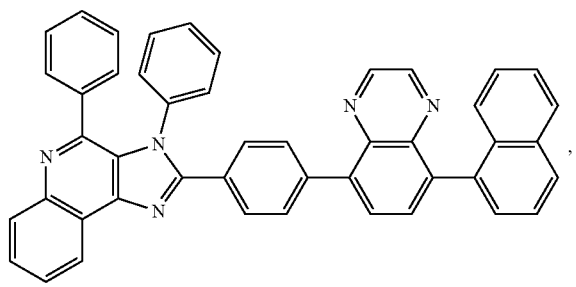
CJH-P13
CJH-P14
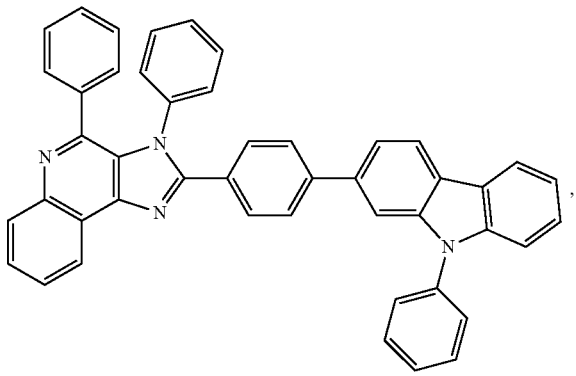

-continued
CJH-P15
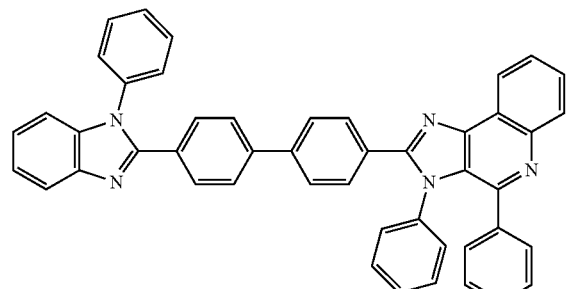
CJH-P16
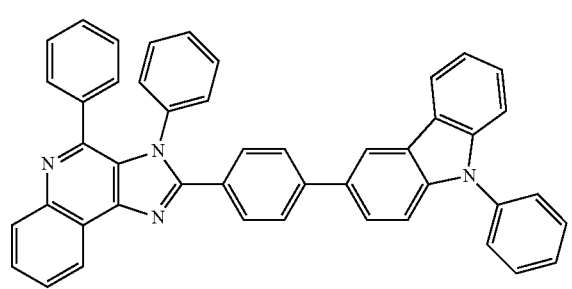
CJH-P17
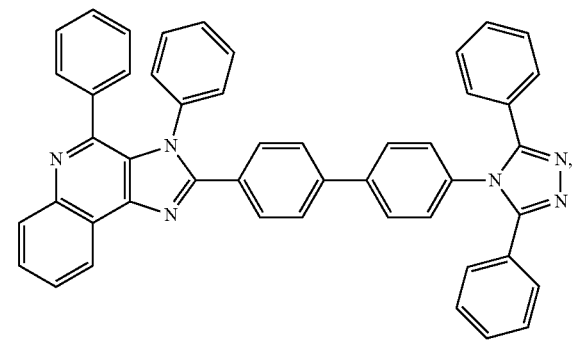
CJH-P18
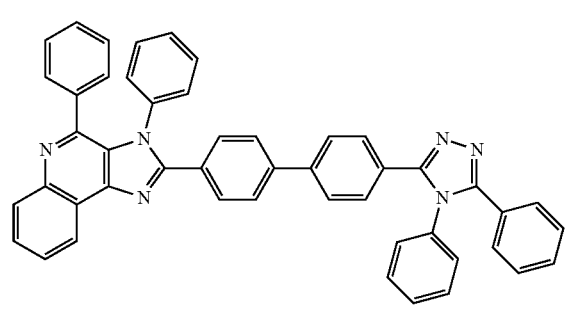
CJH-P19
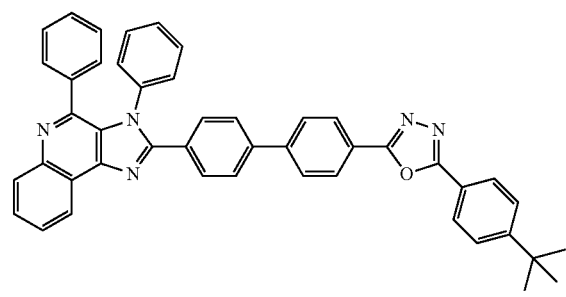
-continued
CJH-P20
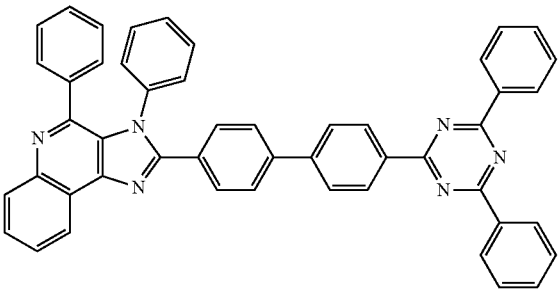
CJH-P21
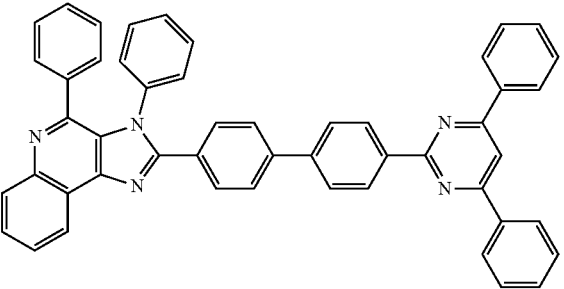
CJH-P22
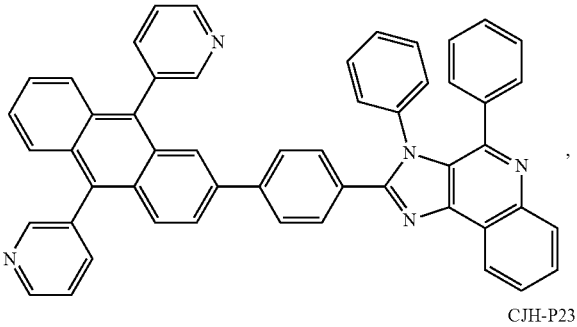
CJH-P23
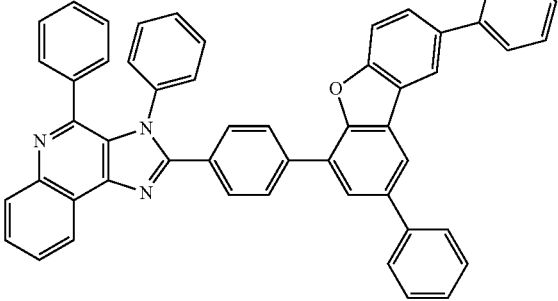
CJH-P24
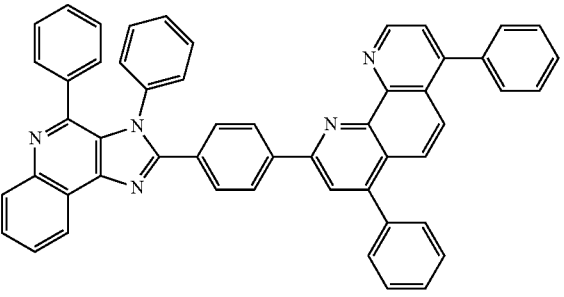

CJH-P25
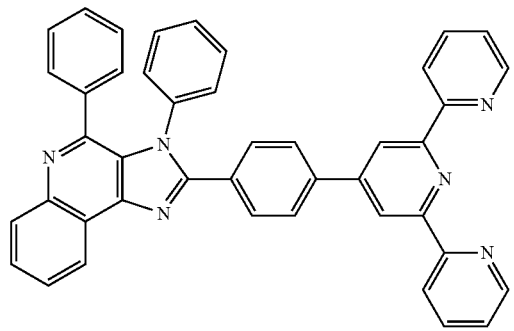
CJH-P26
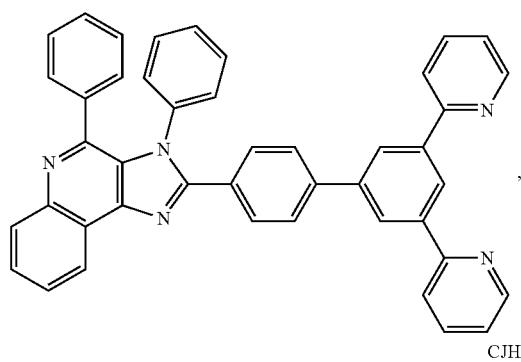
CJH-P27
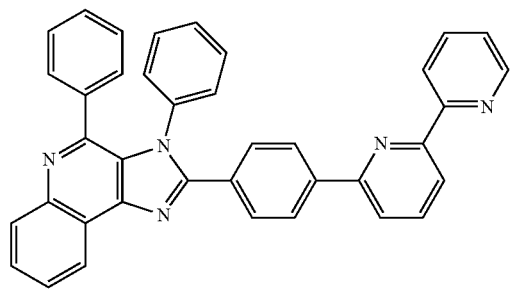
CJH-P28
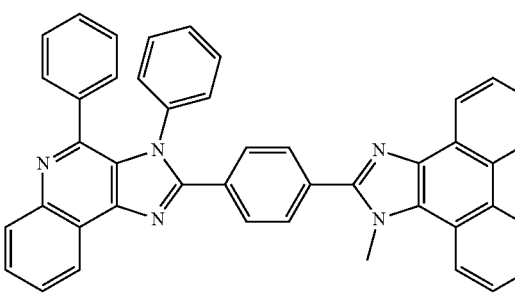
CJH-P29
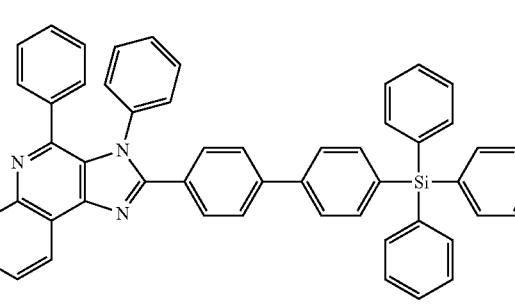
CJH-P30
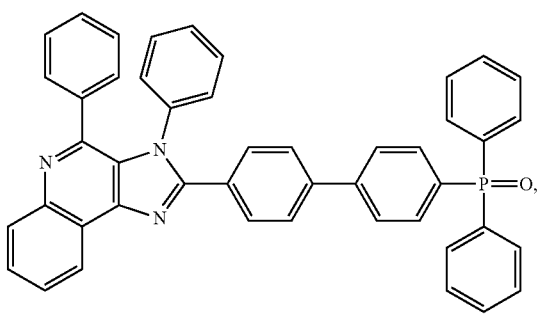
CJH-P31
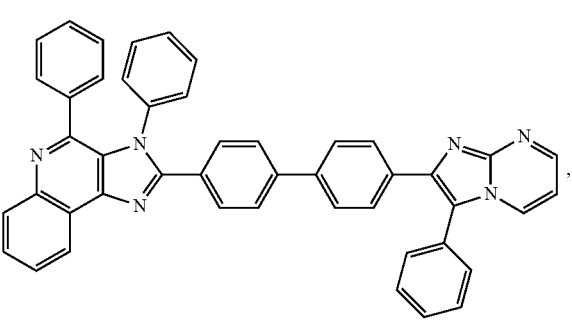
CJH-P32
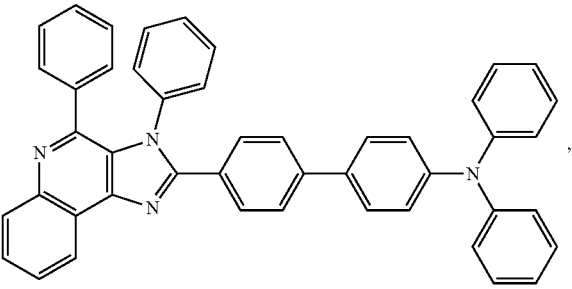
CJH-P33
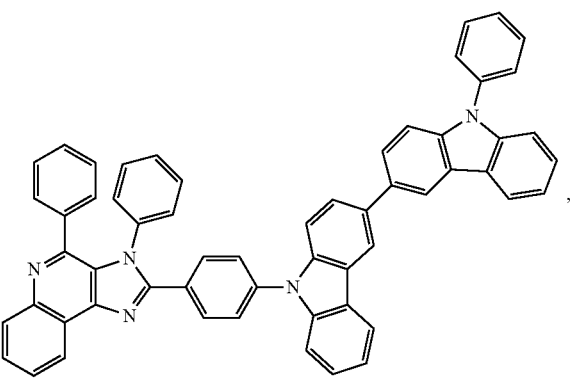

-continued
CJH-P34
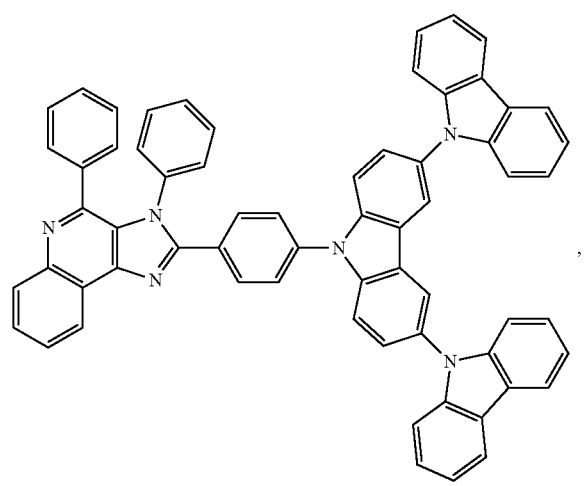
CJH-P35
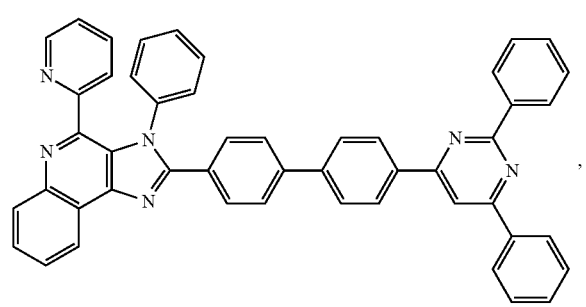
CJH-P36
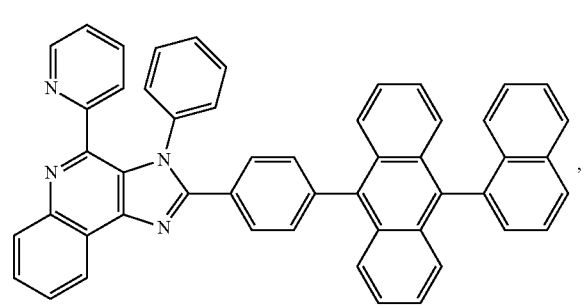
CJH-P37
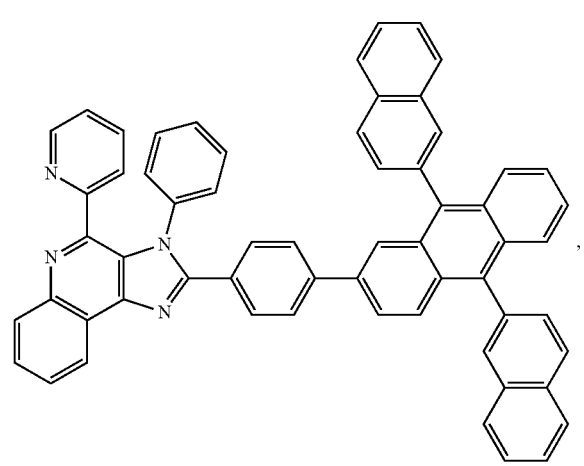
CJH-P38
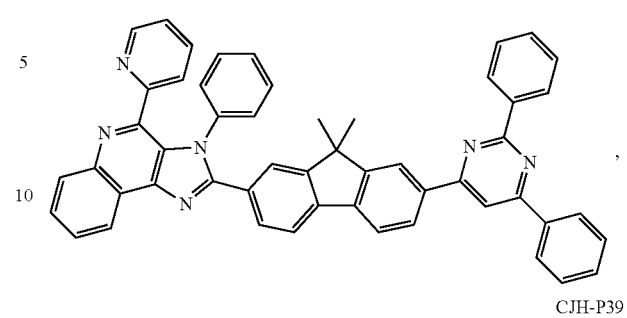
CJH-P39, CJH-P40, CJH-P41
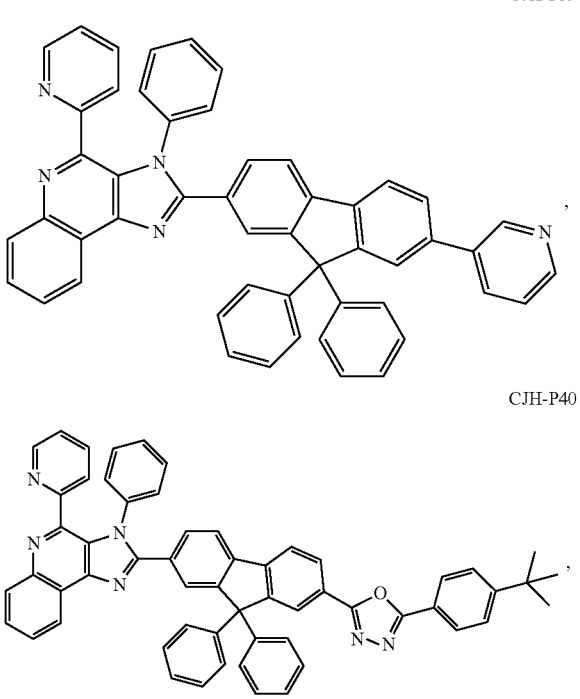
CJH-P42
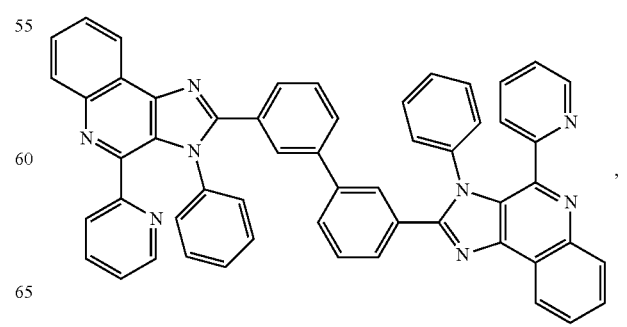

77
-continued
CJH-P43
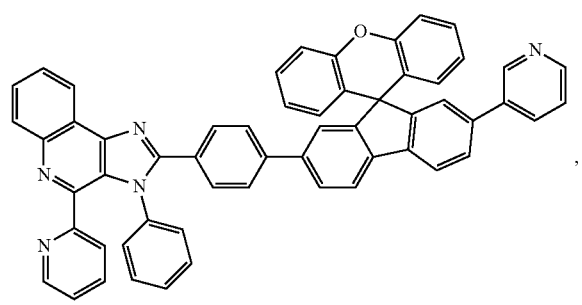
CJH-P44
CJH-P45
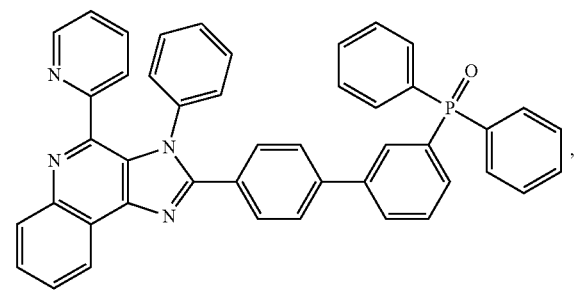
CJH-P46
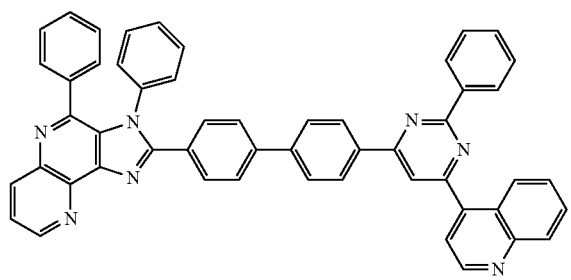
CJH-P47
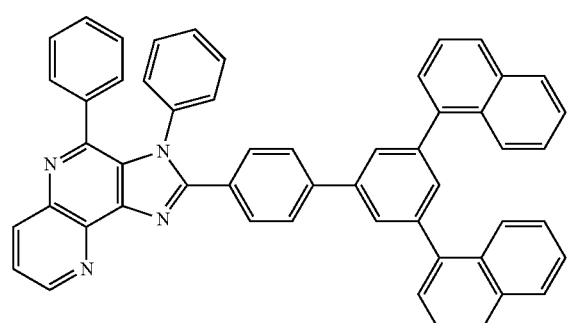
78
-continued
CJH-P48
CJH-P49
CJH-P50
CJH-P51
CJH-P52
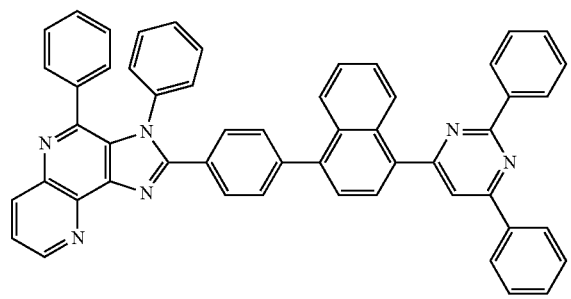

CJH-P53
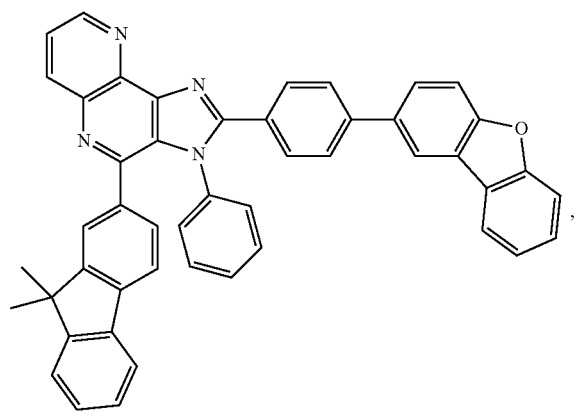
CJH-P57
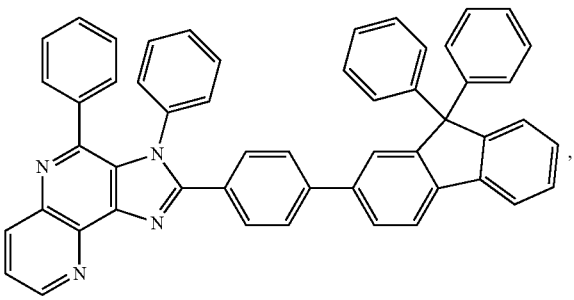
CJH-P54
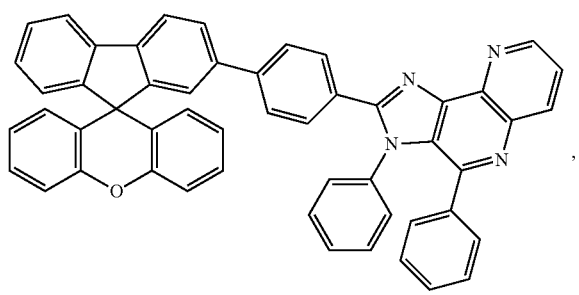
CJH-P58
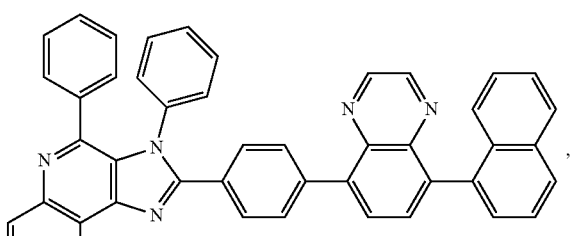
CJH-P55
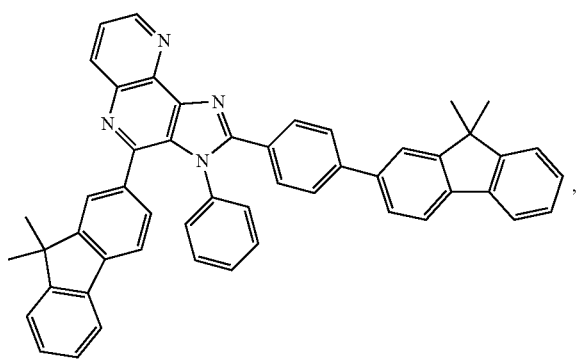
CJH-P59
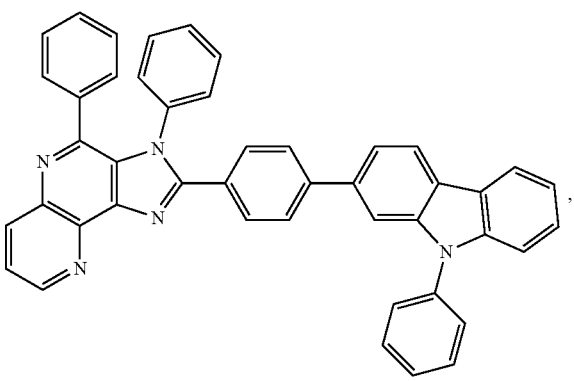
CJH-P56
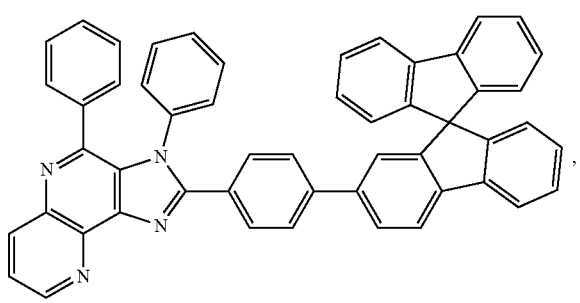
CJH-P60
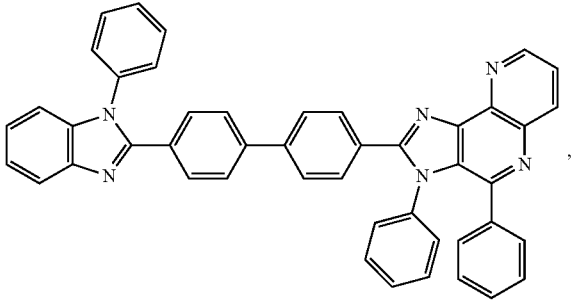

CJH-P61
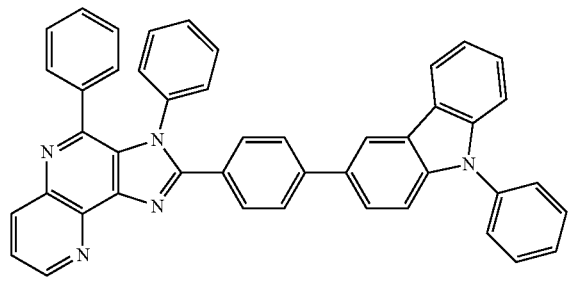
CJH-P66
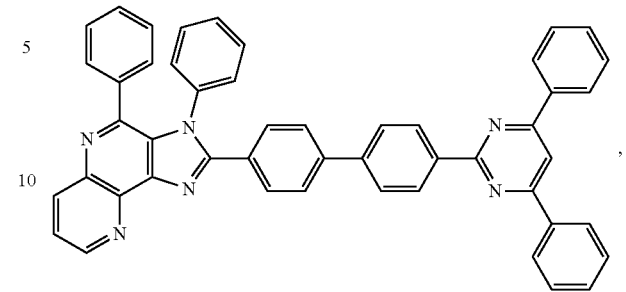
CJH-P62
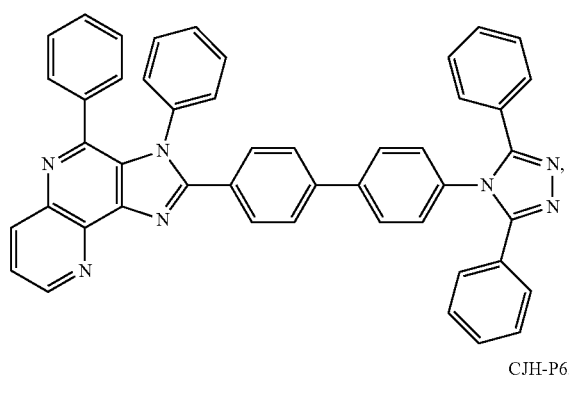
CJH-P67
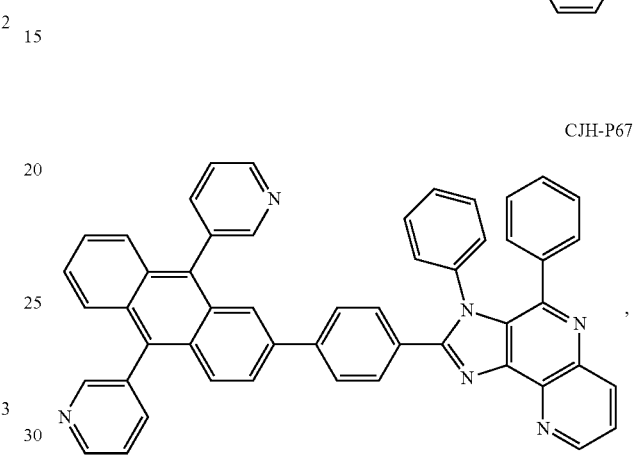
CJH-P63
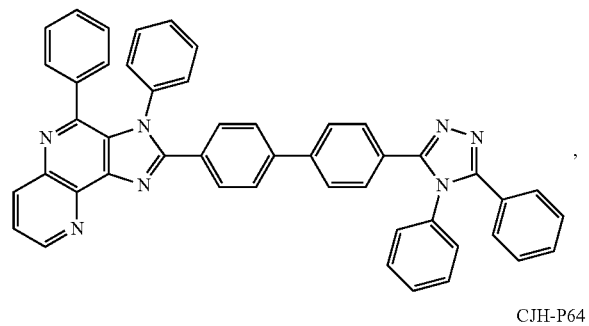
CJH-P68
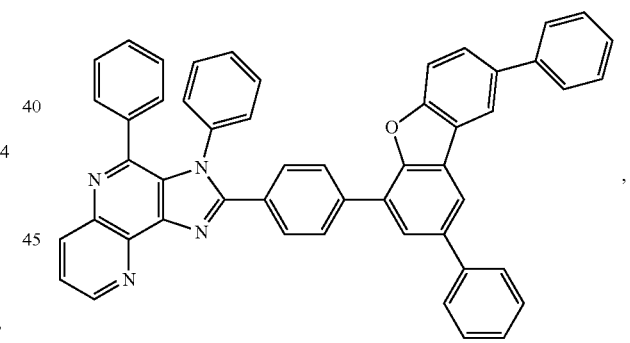
CJH-P64
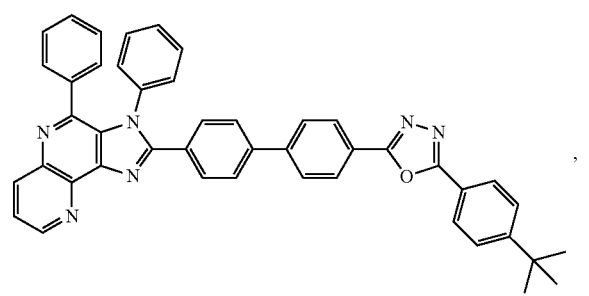
CJH-P65
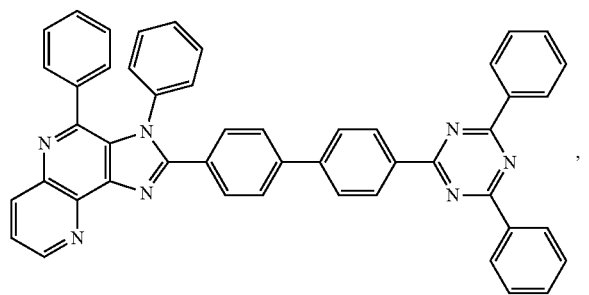
CJH-P69
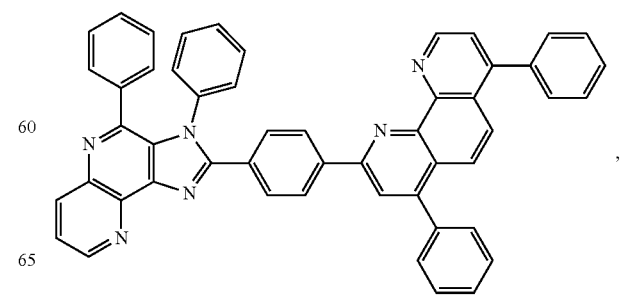

-continued
CJH-P70
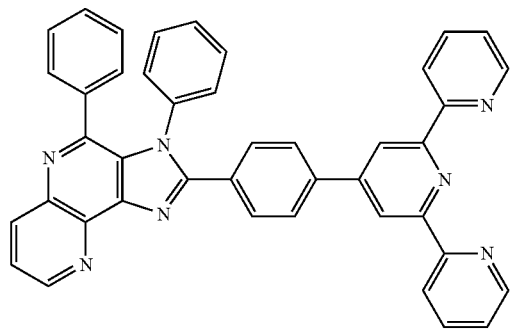
CJH-P74
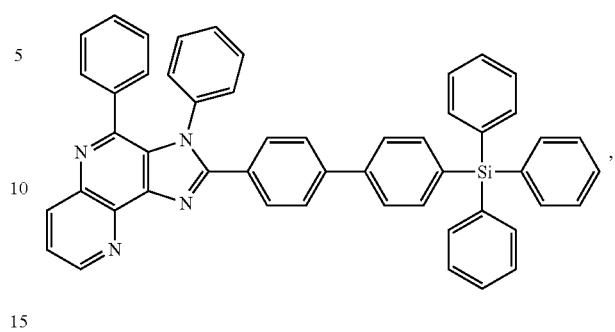
CJH-P71
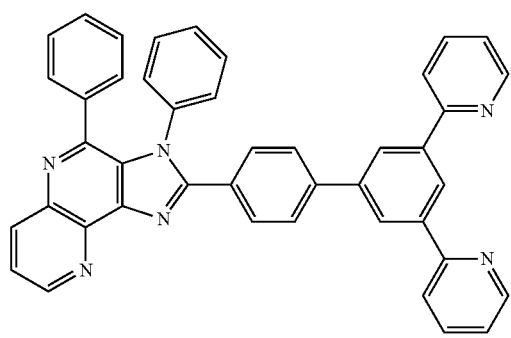
CJH-P75
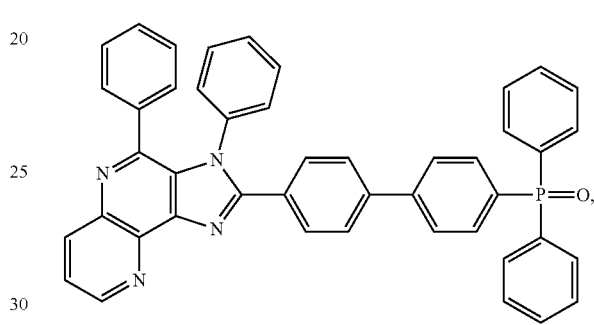
CJH-P72
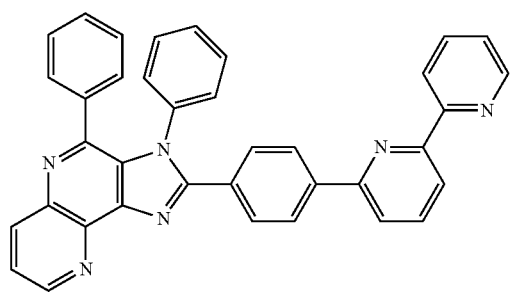
CJH-P76
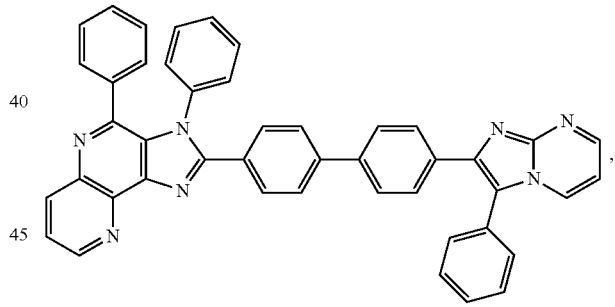
CJH-P73
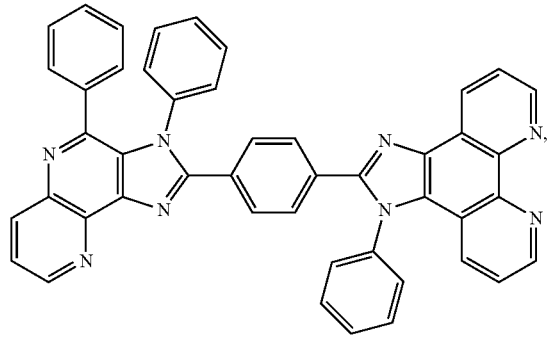
CJH-P77
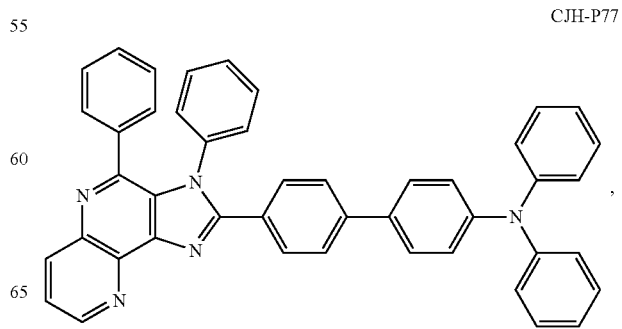

CJH-P78
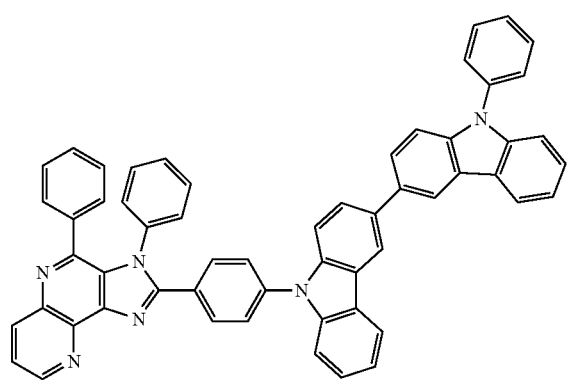
CJH-P82
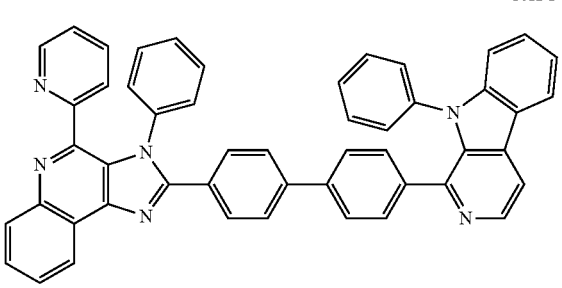
CJH-P83
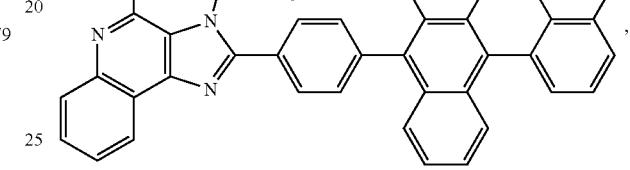
CJH-P79
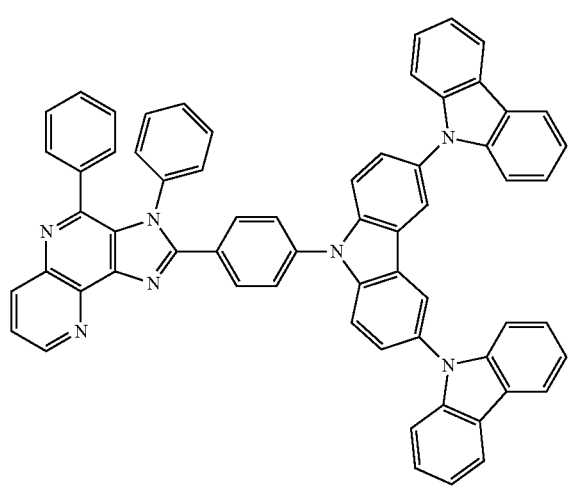
CJH-P84
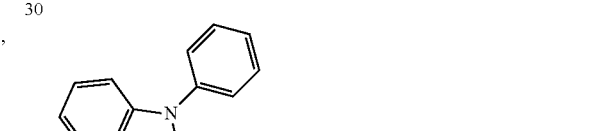
CJH-P80
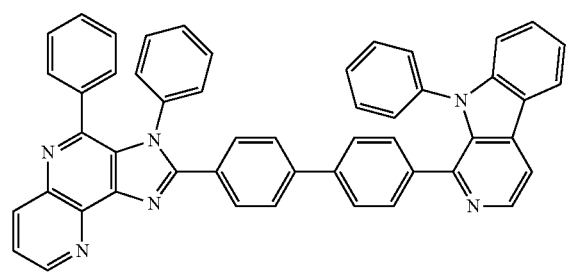
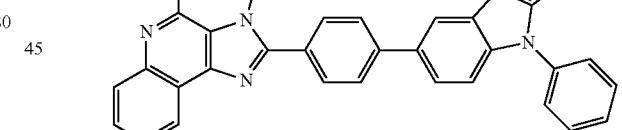
CJH-P85
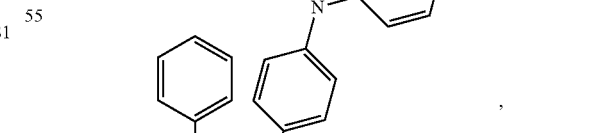
CJH-P81
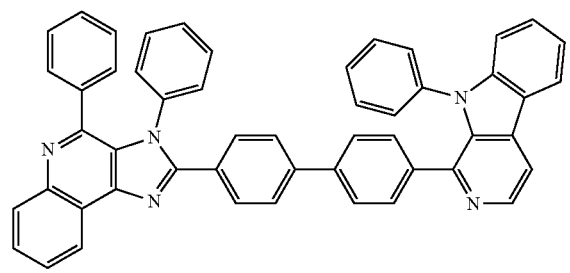
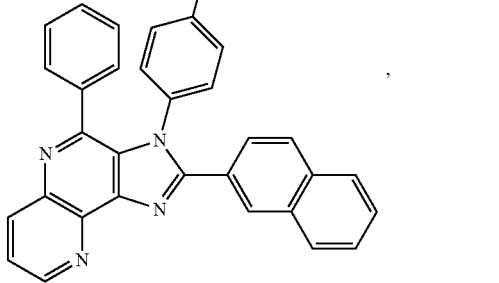

-continued
CJH-P86
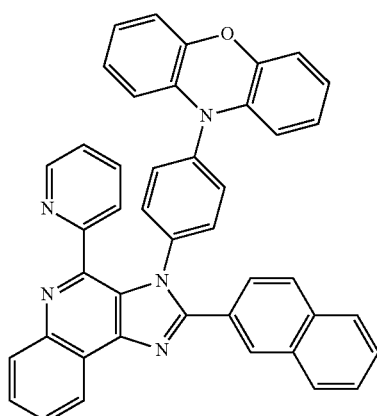
CJH-P87
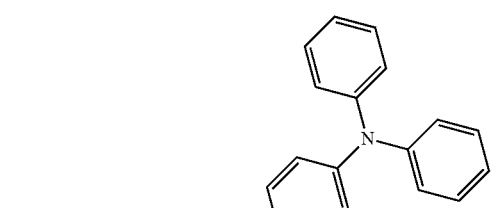
CJH-P88
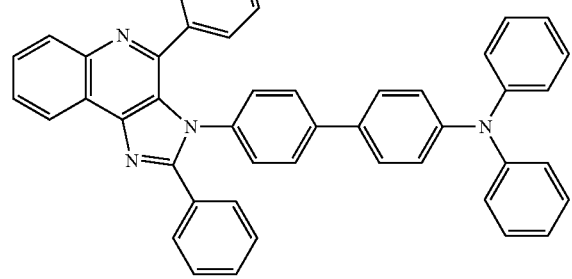
CJH-P89
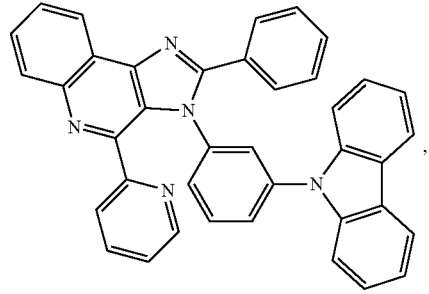
-continued
CJH-P90
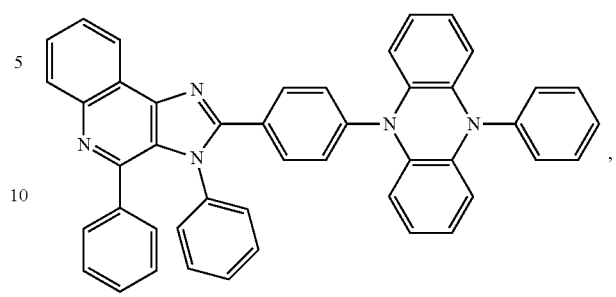
CJH-P91
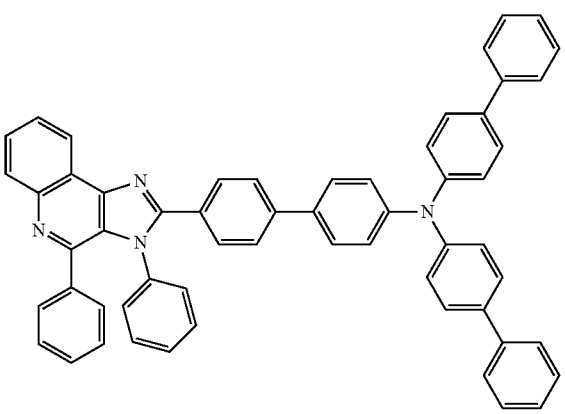
CJH-P92
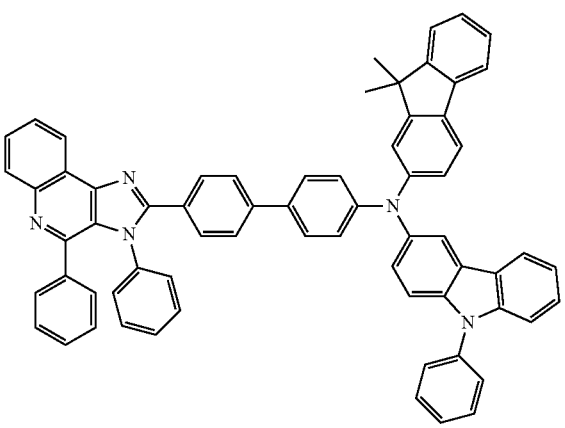

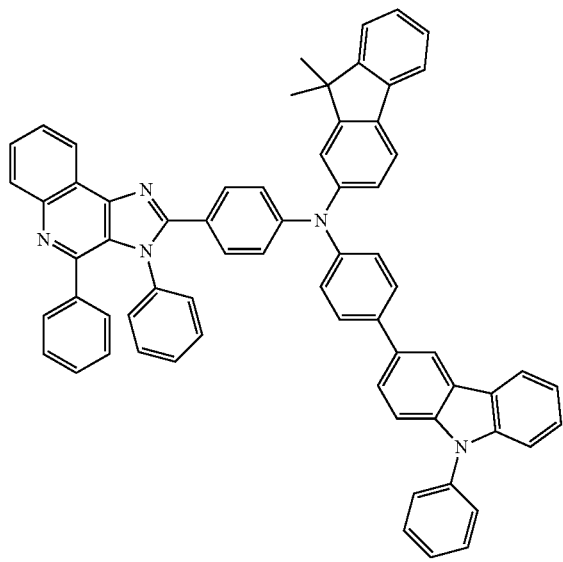
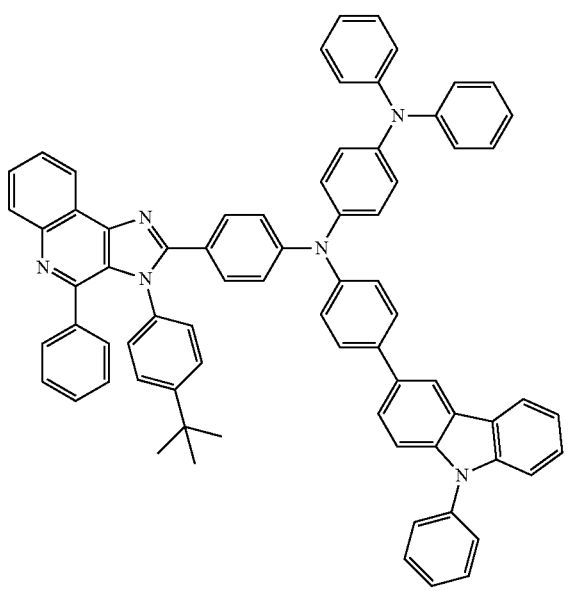
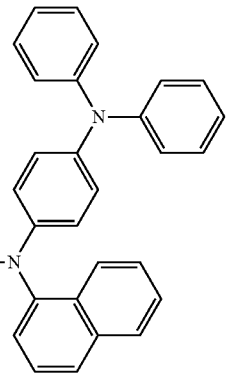

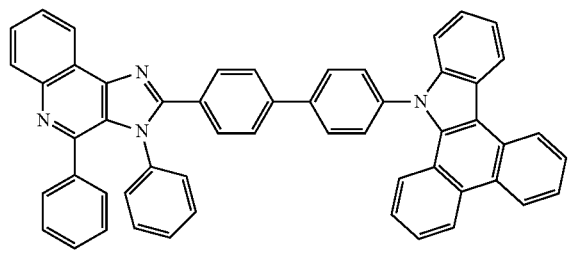

CJH-P99

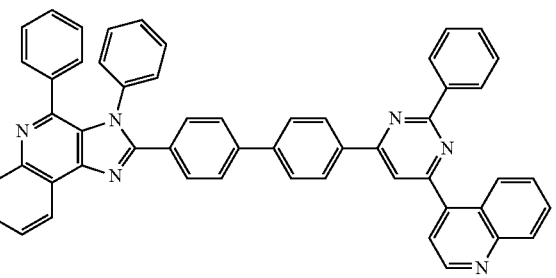

CJH-P01

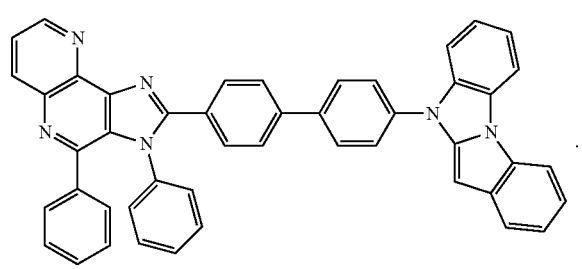

CJH-P100

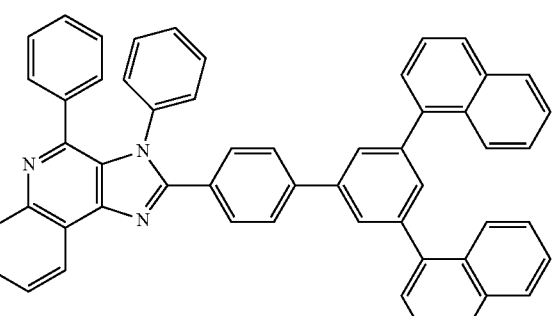

CJH-P02

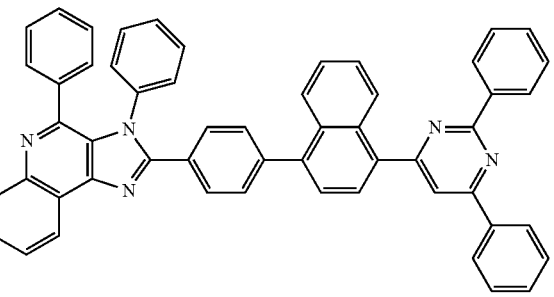

CJH-P03

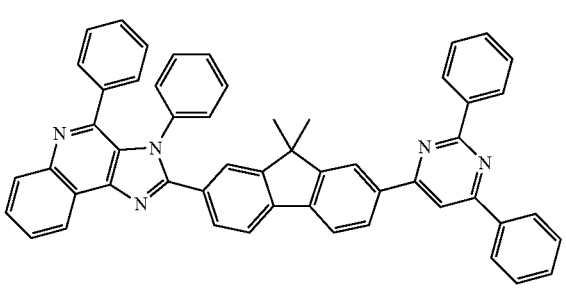

CJH-P04

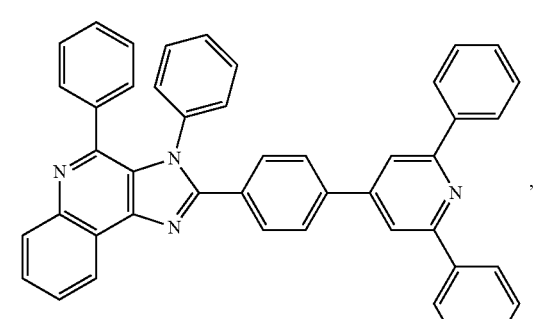

CJH-P05

4. A material, wherein a raw material of the material contains one or a plurality of the imidazole derivatives according to claim 1.

5. The material according to claim 4, wherein the material is an organic light-emitting material.

6. An organic light-emitting device, wherein a material of the organic light-emitting device contains one or a plurality of the imidazole derivatives according to claim 1.

7. The organic light-emitting device according to claim 6, wherein the material of at least one of a hole transport layer, an organic light-emitting layer, and an electron transport layer in the organic light-emitting device contains one or a plurality of the imidazole derivatives.

8. The organic light-emitting device according to claim 7, wherein the thickness of the hole injection layer is 30-50 nm; the thickness of the hole transport layer is 5-15 nm; the thickness of the organic light-emitting layer is 10-100 nm; the thickness of the electron transport layer is 10-30 nm; and the thickness of the cathode layer is 90-110 nm.

9. A method of preparing an organic light-emitting material comprising steps of preparing a layer of the imidazole derivative according to claim 1 and forming the organic light-emitting material including the layer of the imidazole derivative according to claim 1.

10. A method of preparing an organic light-emitting device comprising steps of preparing a layer of the imidazole derivative according to claim 1 and forming the organic light-emitting device including the layer of the imidazole derivative according to claim 1.

11. The imidazole derivative according to claim 2, wherein the structural formula of the compound having a structural formula I is specifically represented by the following formulas CJH-P01 to CJH-P100:

CJH-P06
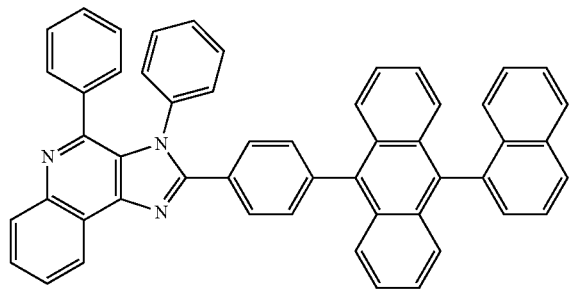
CJH-P07
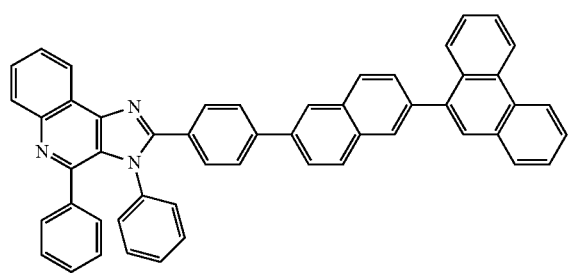
CJH-P08
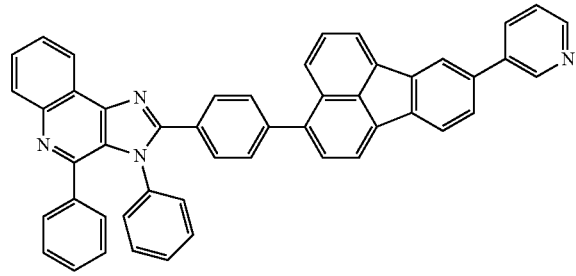
CJH-P09
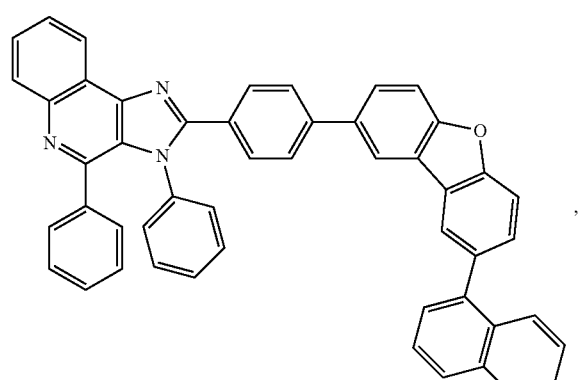
CJH-P10
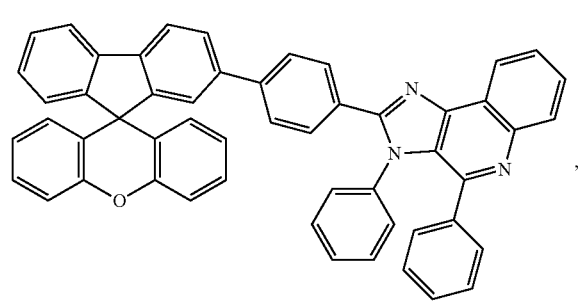
CJH-P11
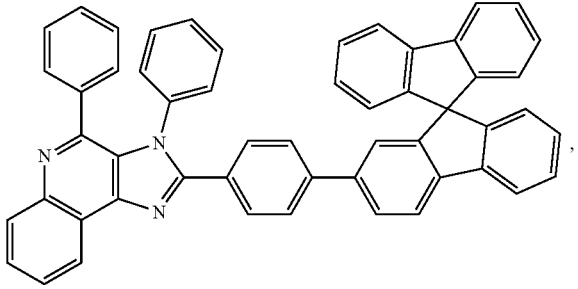
CJH-P12
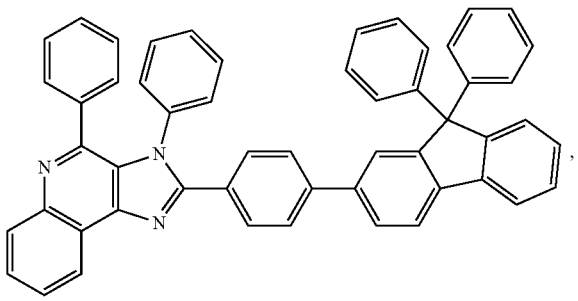
CJH-P13
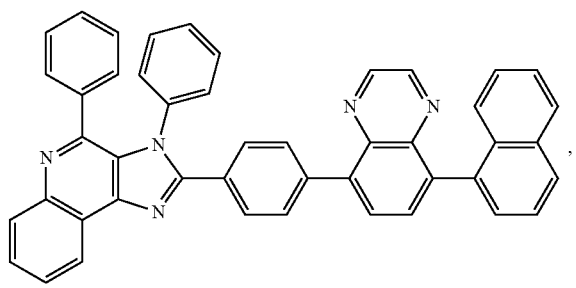
CJH-P14
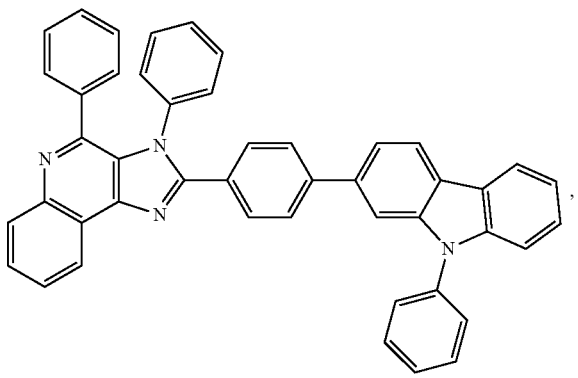

-continued
CJH-P15
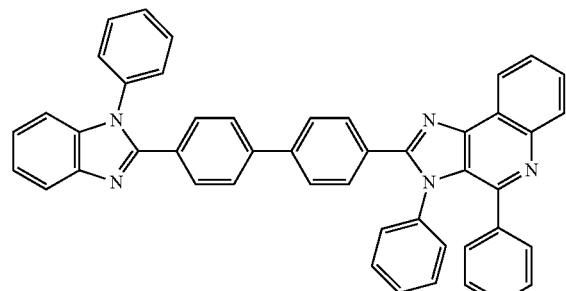
CJH-P16
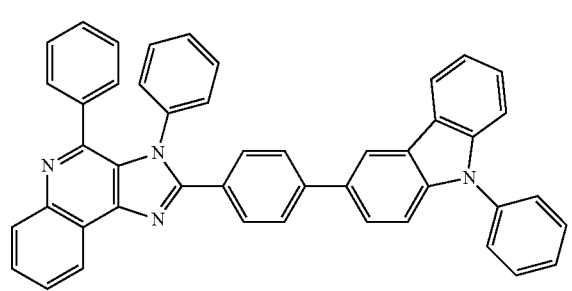
CJH-P17
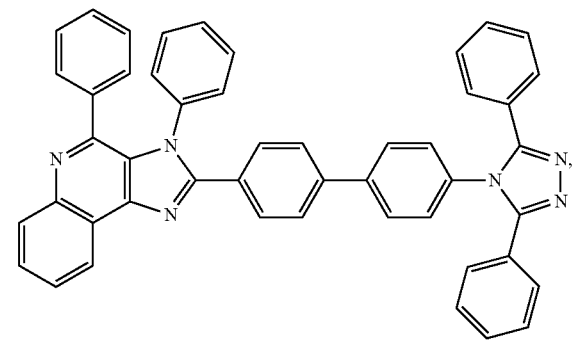
CJH-P18
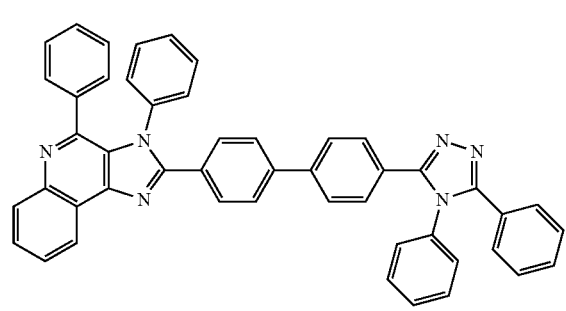
CJH-P19
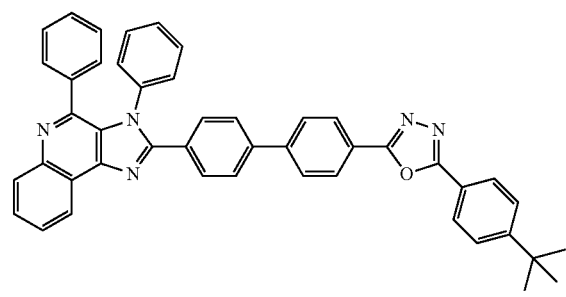
-continued
CJH-P20
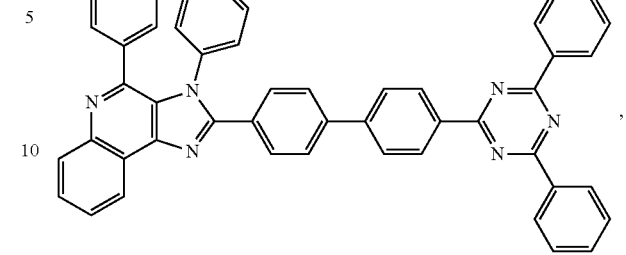
CJH-P21
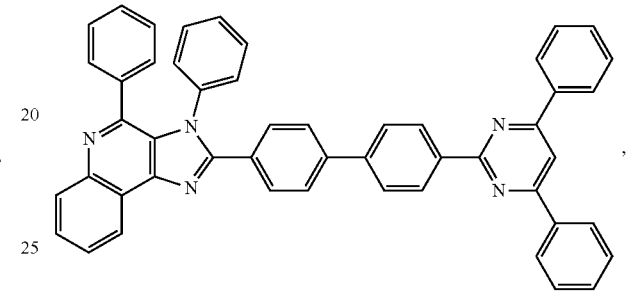
CJH-P22
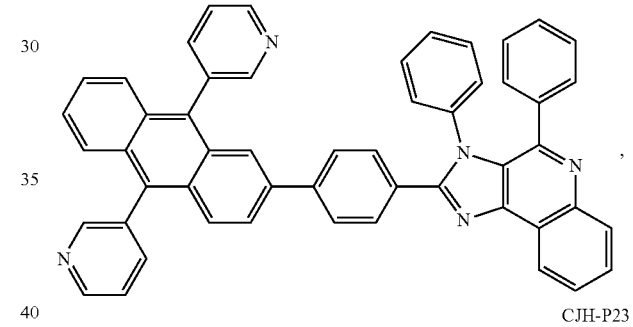
CJH-P23
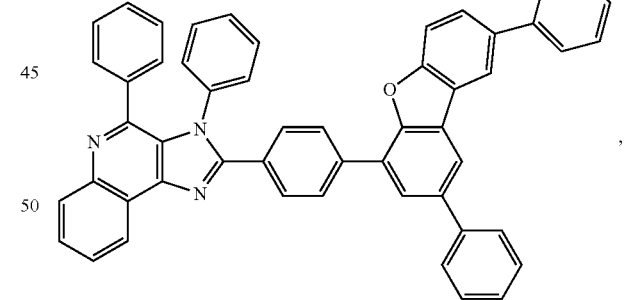
CJH-P24
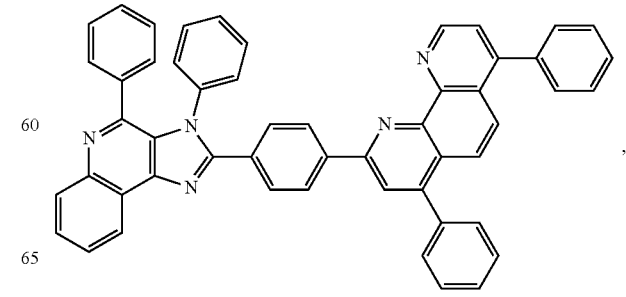

CJH-P25
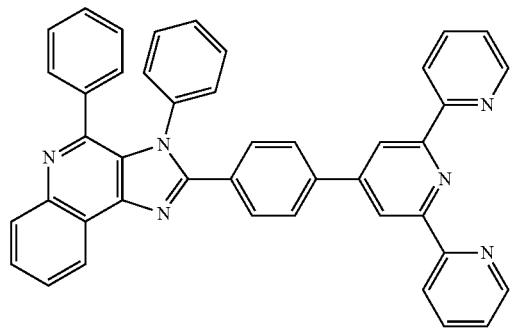
CJH-P26
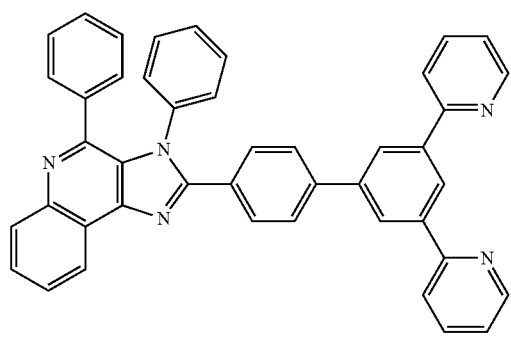
CJH-P27
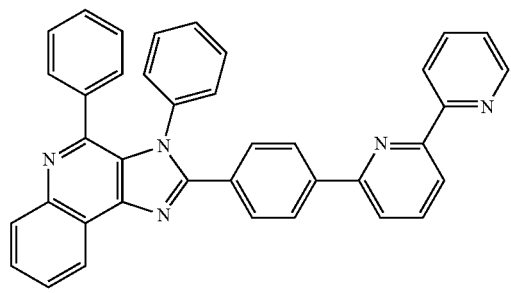
CJH-P28
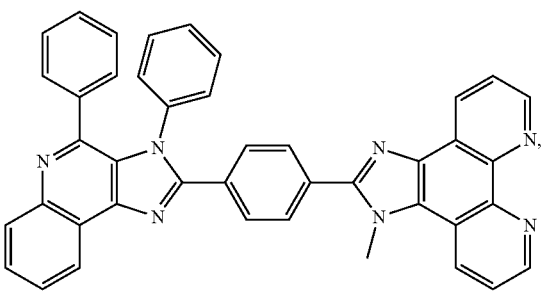
CJH-P29
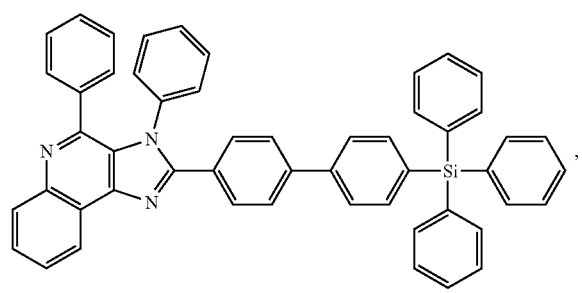
CJH-P30
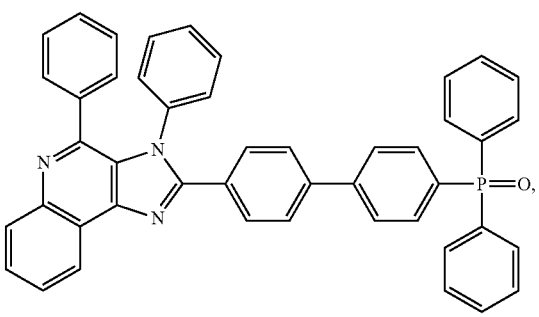
CJH-P31
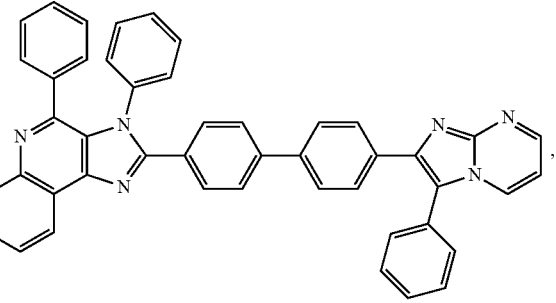
CJH-P32
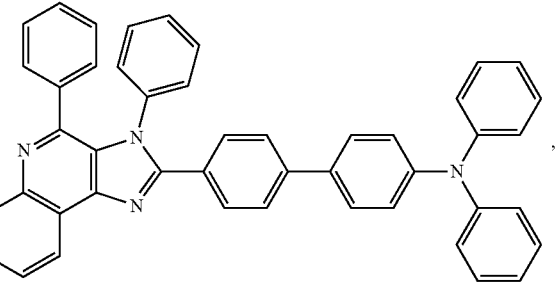
CJH-P33
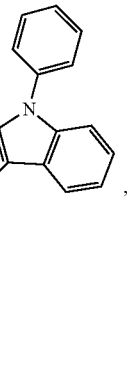

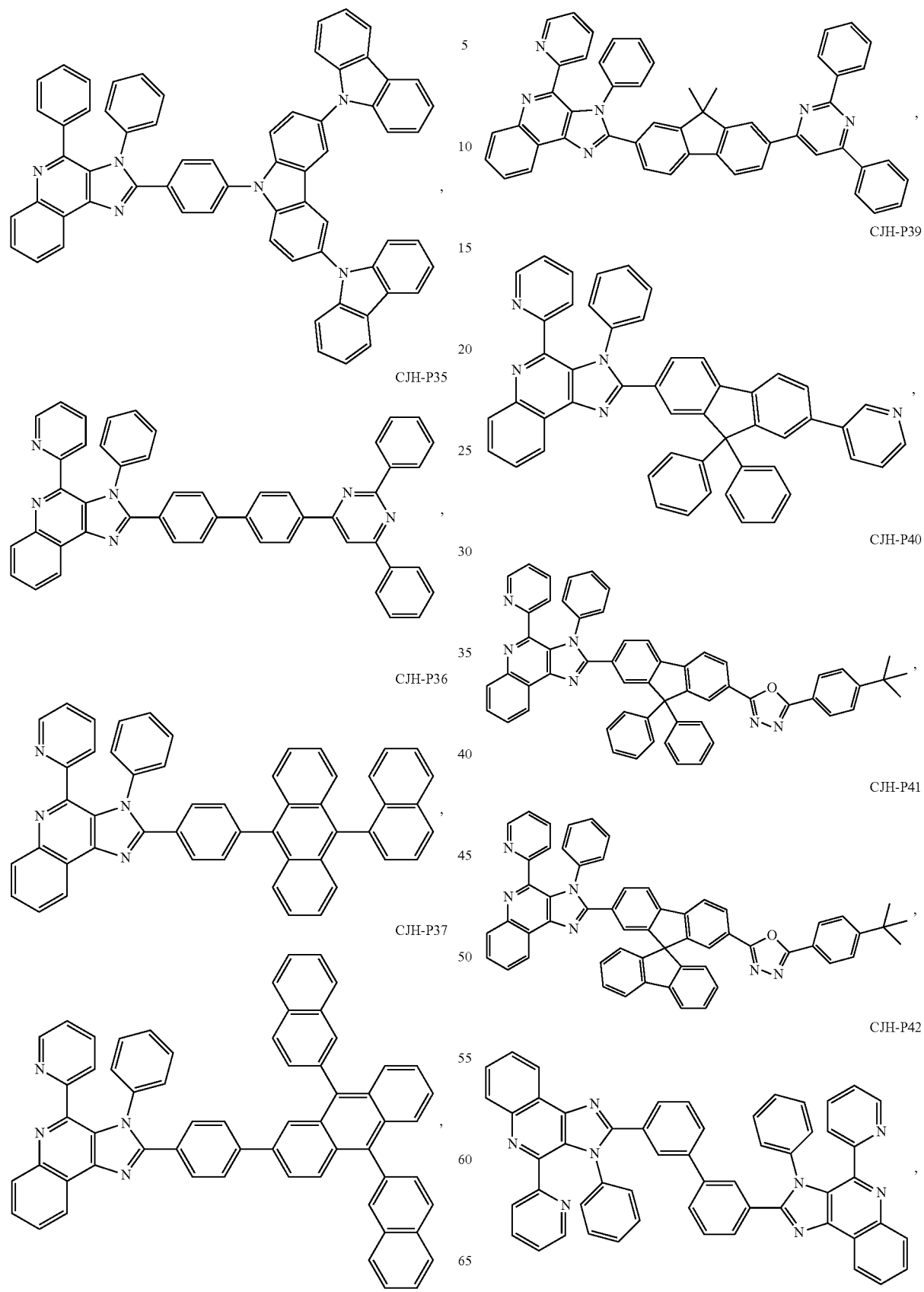

CJH-P43
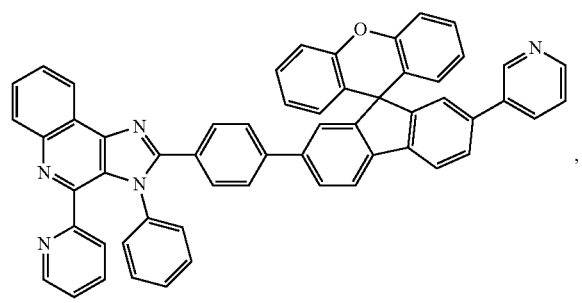
CJH-P44
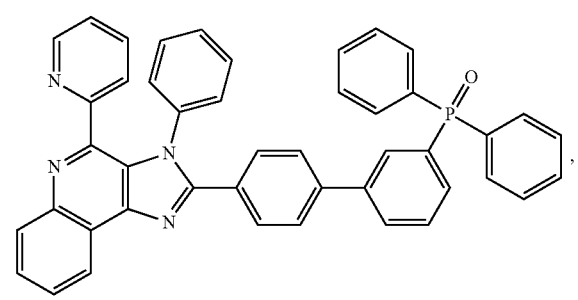
CJH-P45
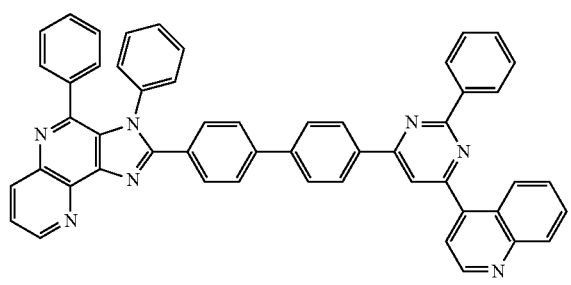
CJH-P46
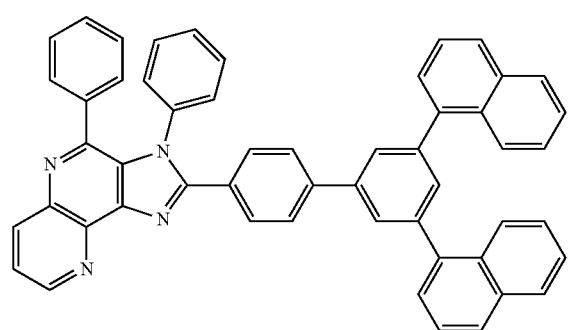
CJH-P47
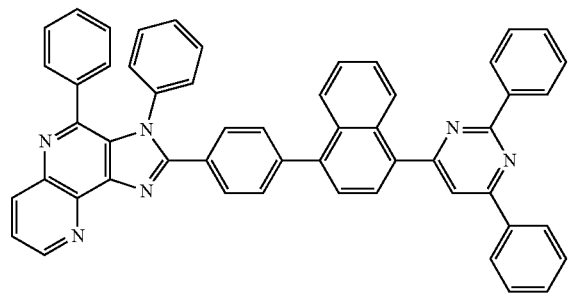
CJH-P48
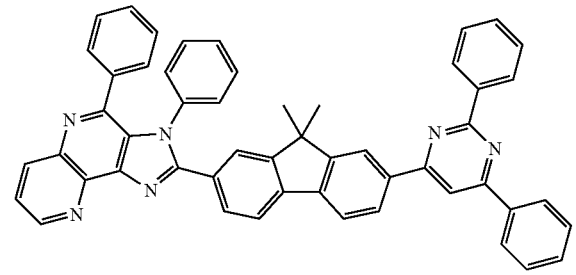
CJH-P49
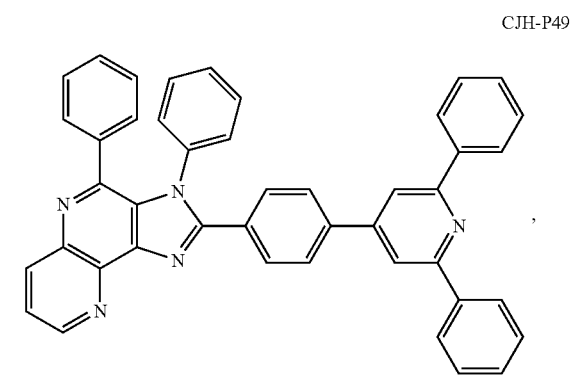
CJH-P50
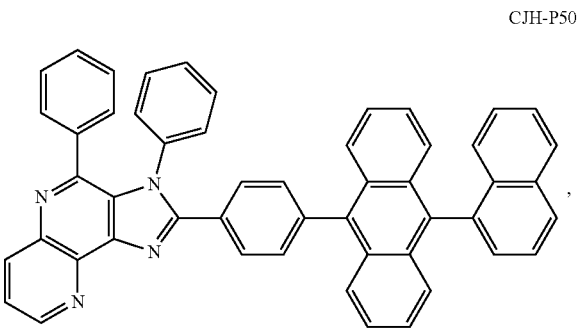
CJH-P51
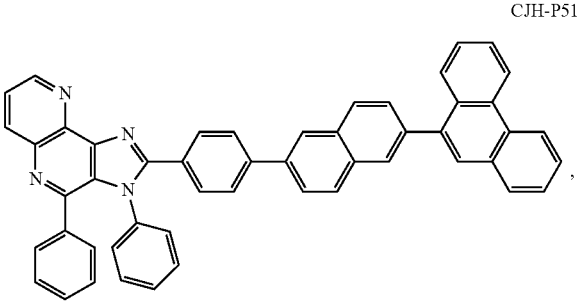
CJH-P52
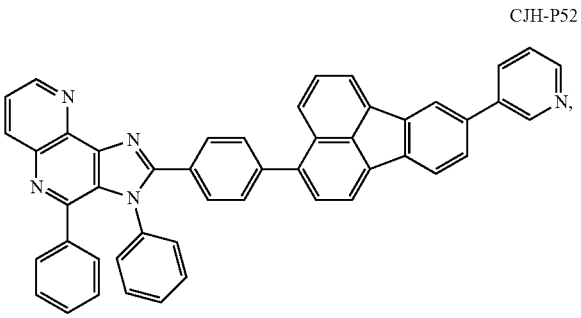

CJH-P53
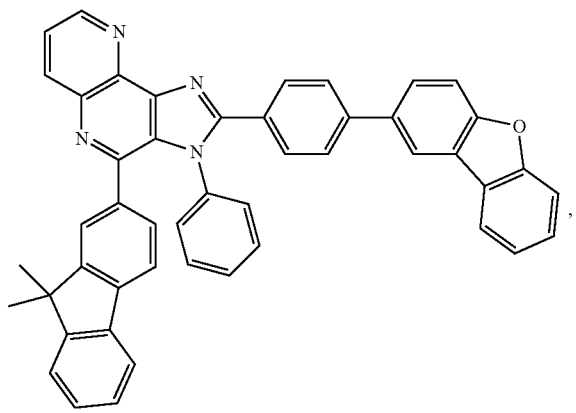
CJH-P54
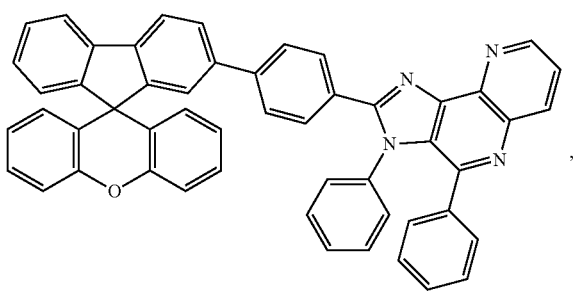
CJH-P55
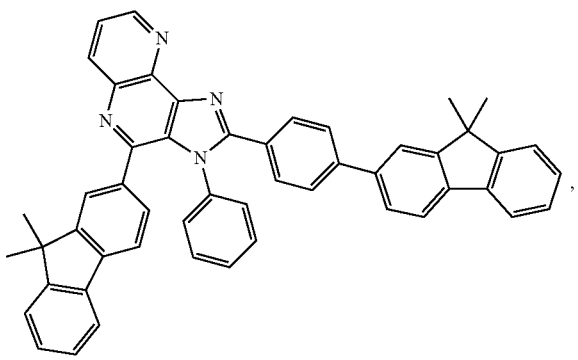
CJH-P56
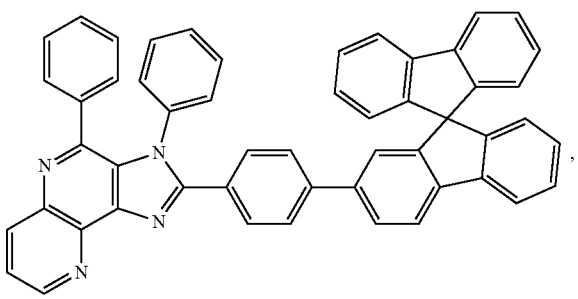
CJH-P57
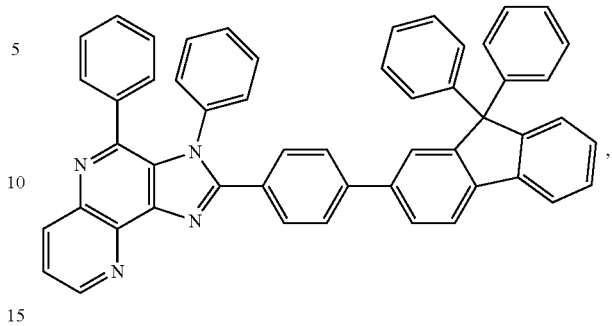
CJH-P58
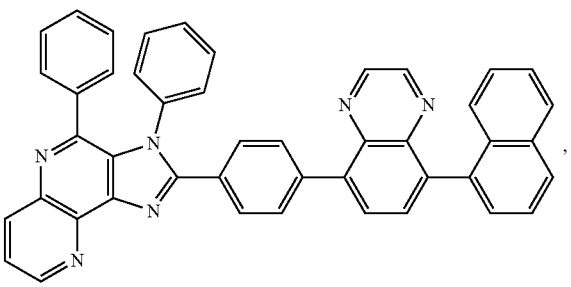
CJH-P59
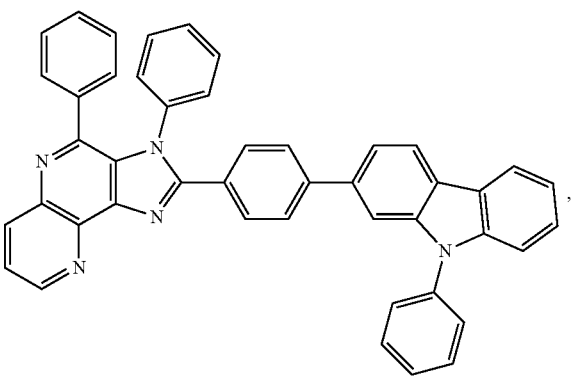
CJH-P60
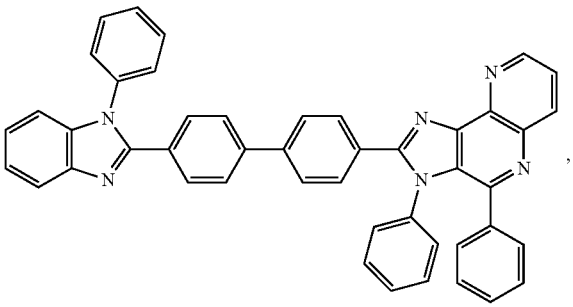

CJH-P61
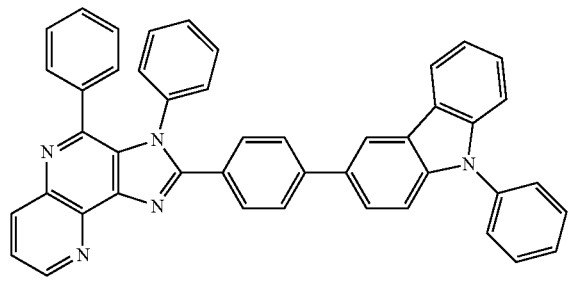
CJH-P62
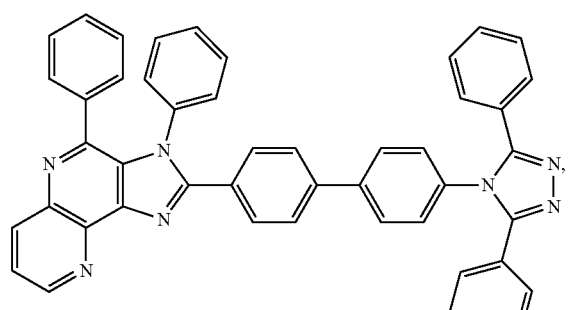
CJH-P63
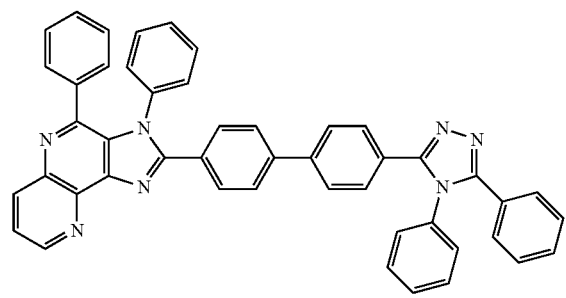
CJH-P64
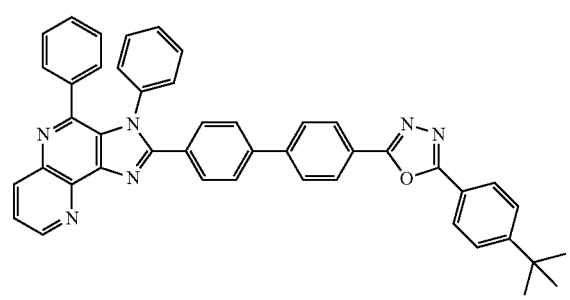
CJH-P65
CJH-P66
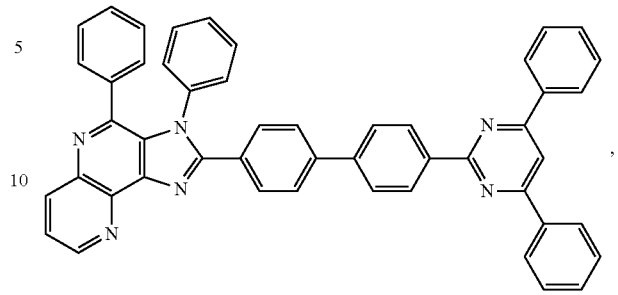
CJH-P67
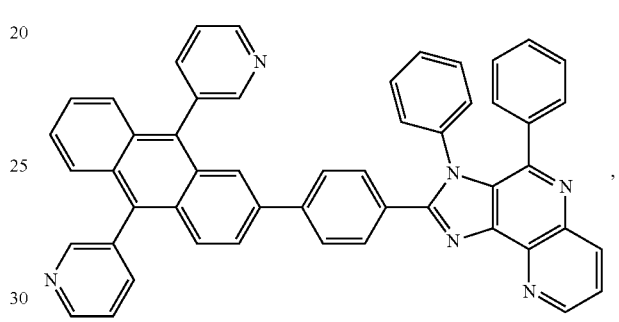
CJH-P68
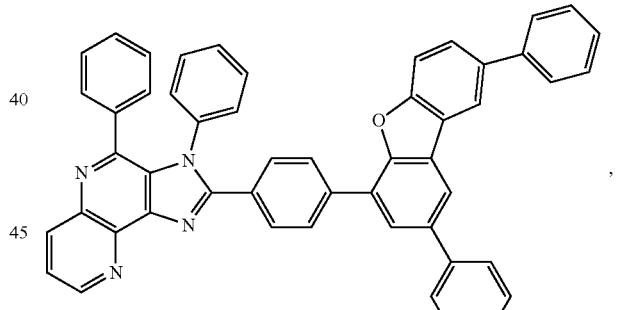
CJH-P69
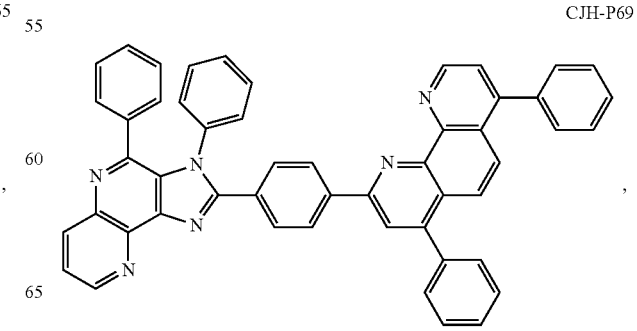

-continued
CJH-P70
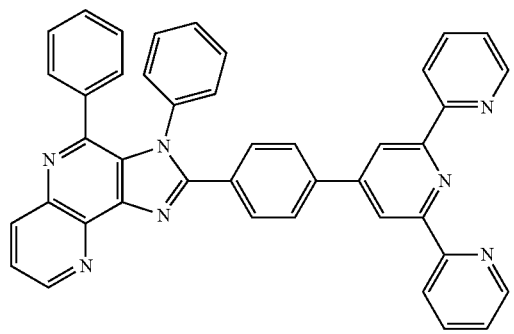
CJH-P71
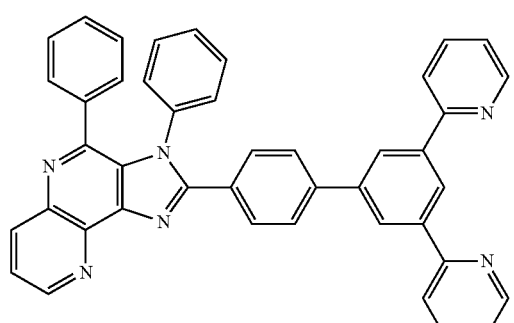
CJH-P72
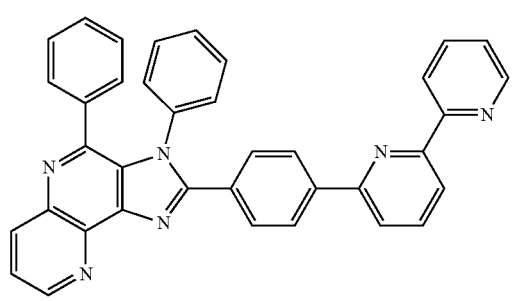
CJH-P73
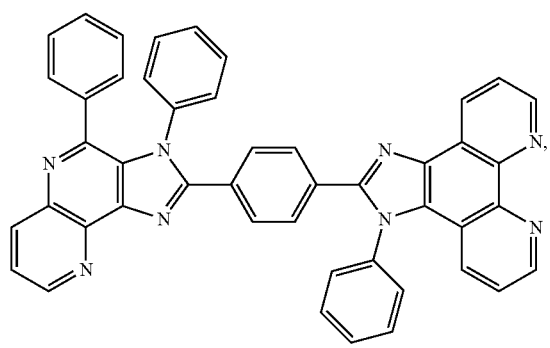
-continued
CJH-P74
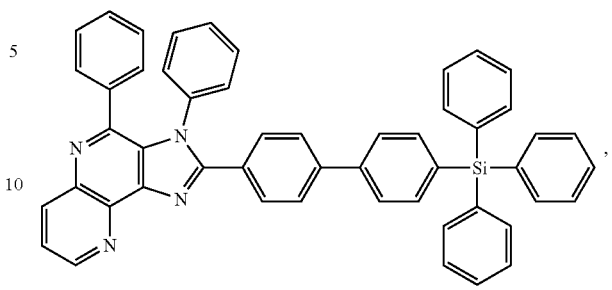
CJH-P75
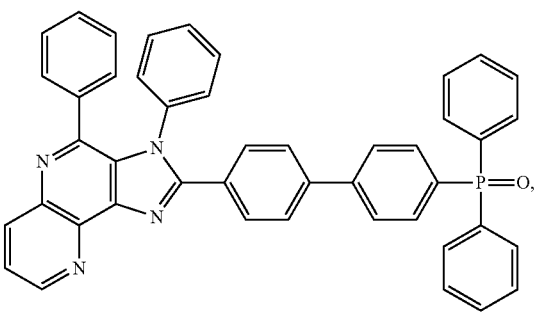
CJH-P76
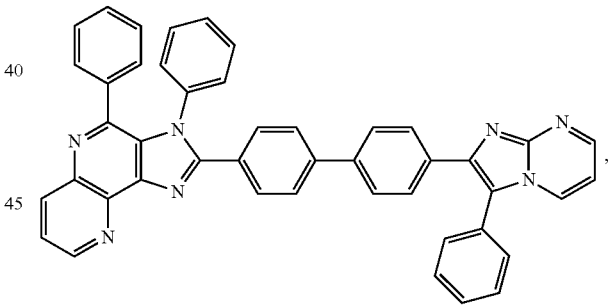
CJH-P77
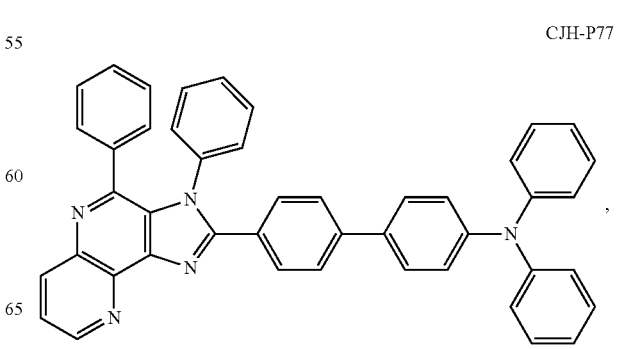

CJH-P78
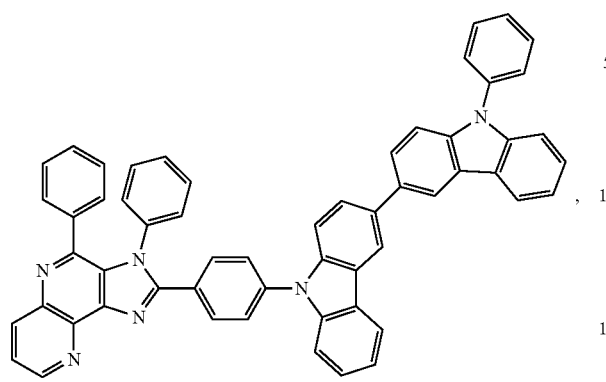
CJH-P82
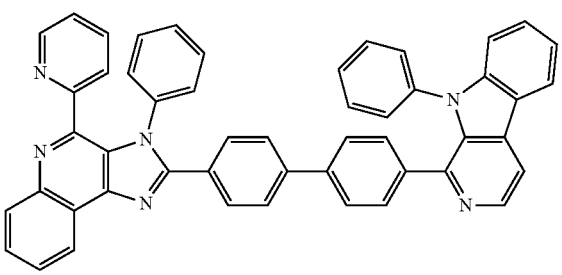
CJH-P83
CJH-P79
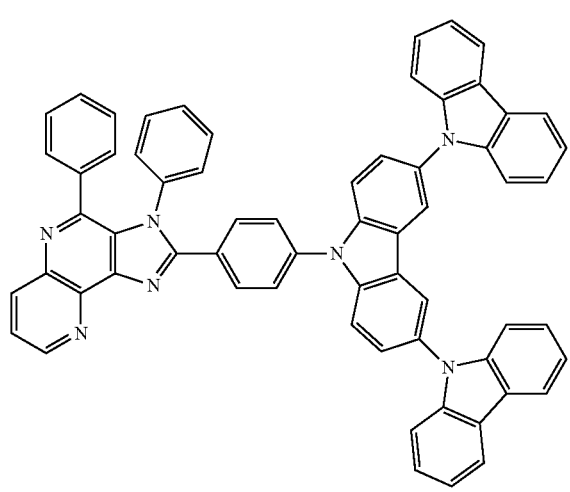
CJH-P84
CJH-P80
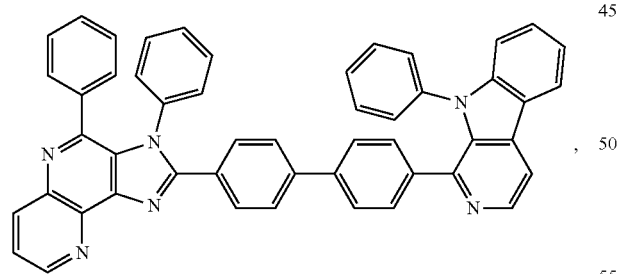
CJH-P81
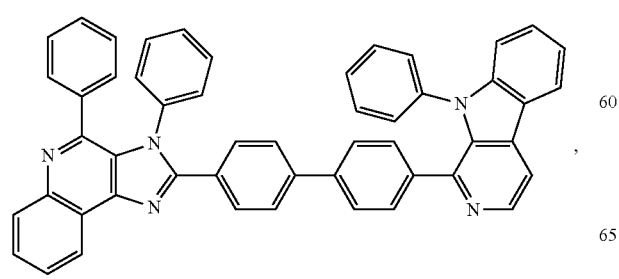
CJH-P85
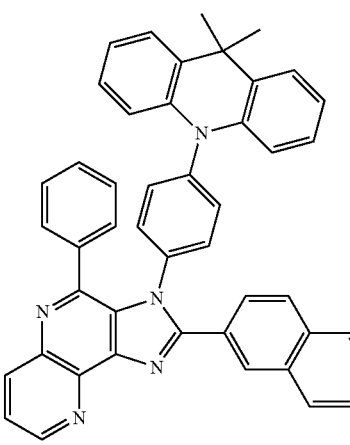

CJH-P86
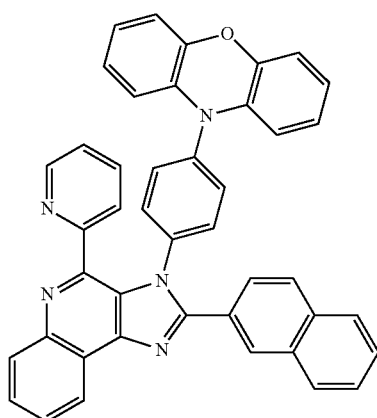
CJH-P87
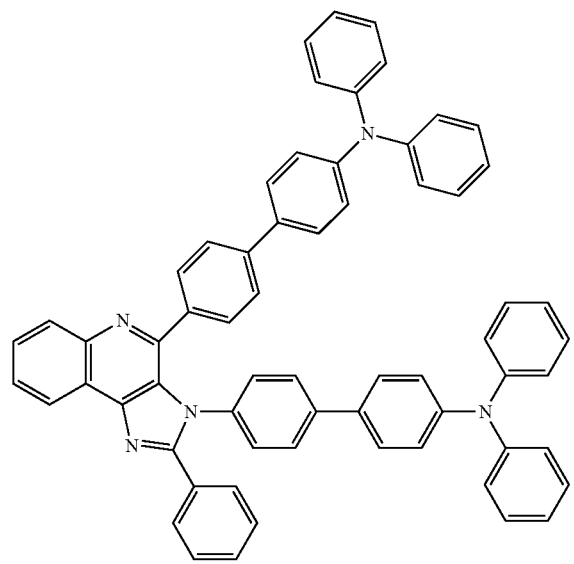
CJH-P88
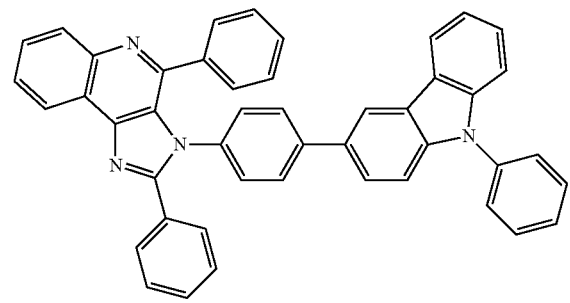
CJH-P89
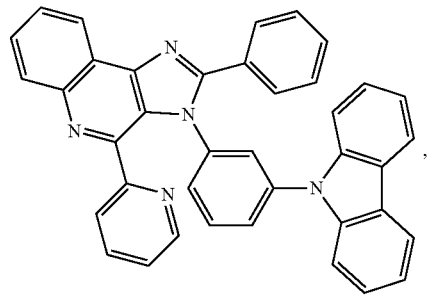
CJH-P90
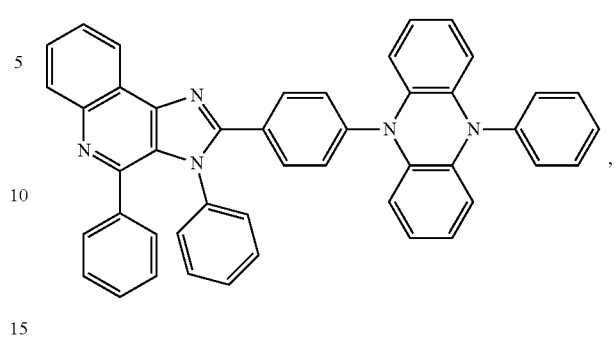
CJH-P91
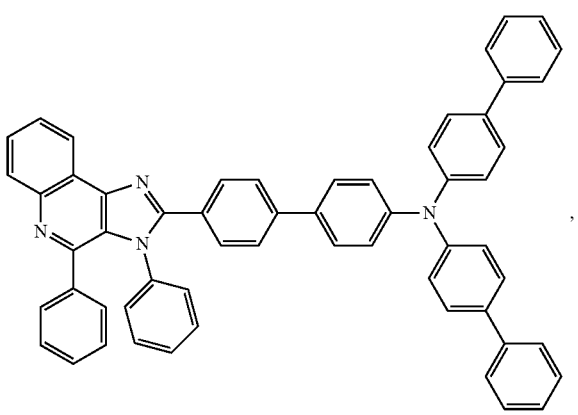
CJH-P92
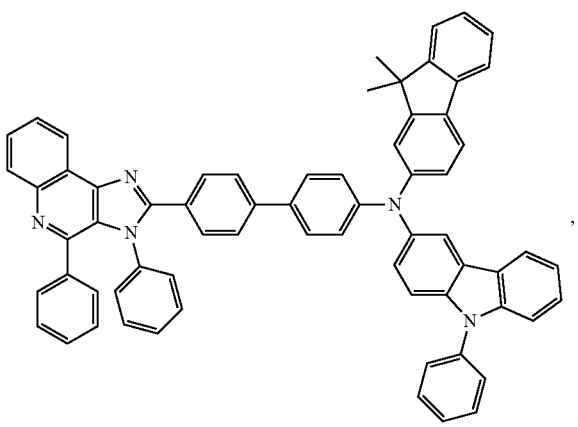

CJH-P93
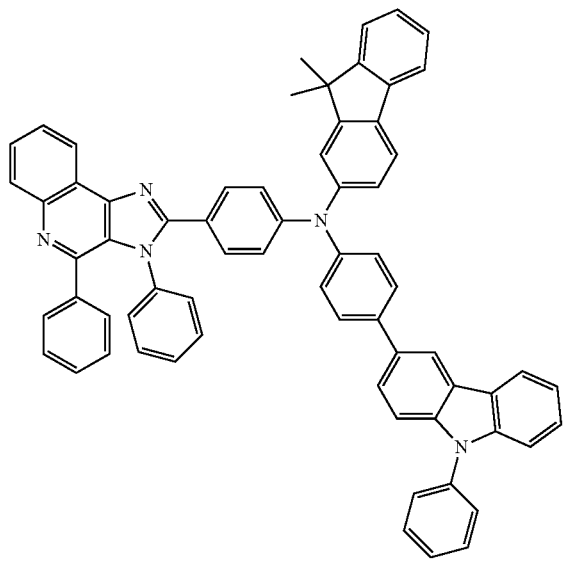
CJH-P94
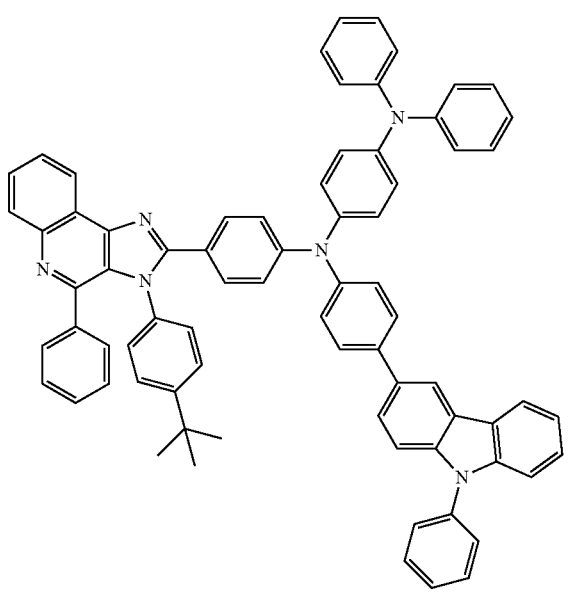
CJH-P95
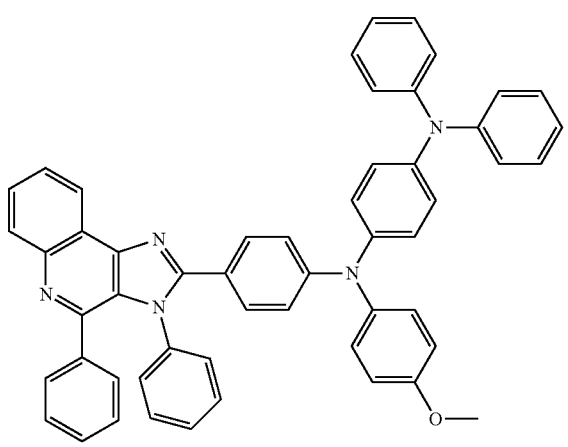
CJH-P96
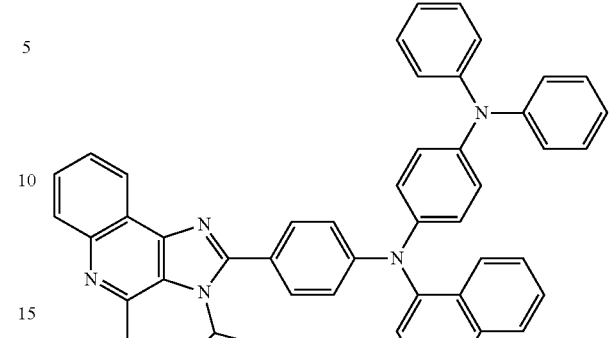
CJH-P97
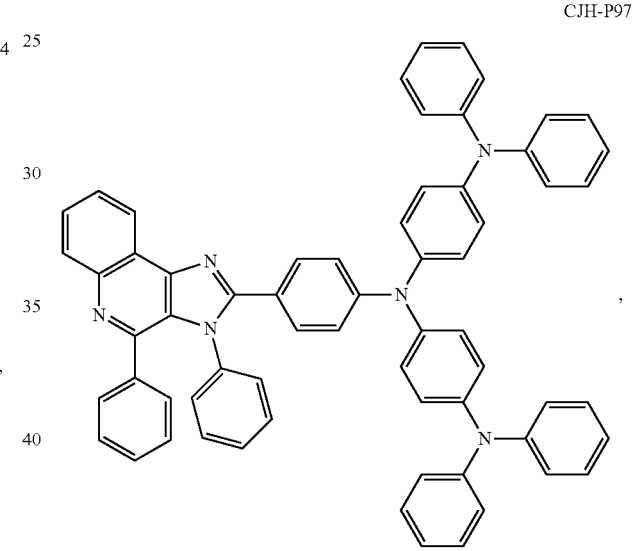
CJH-P98
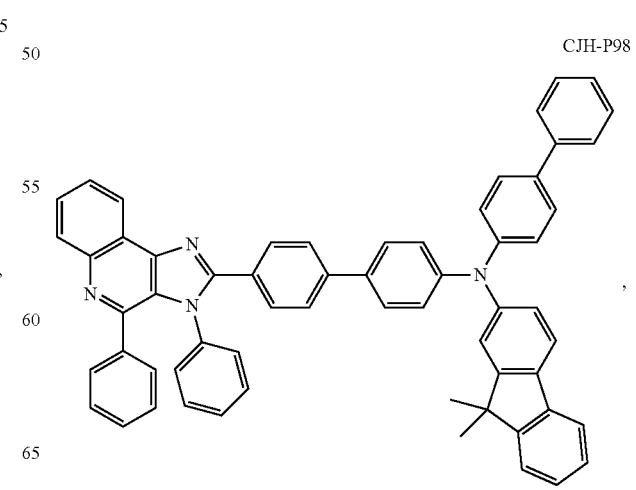

CJH-P99

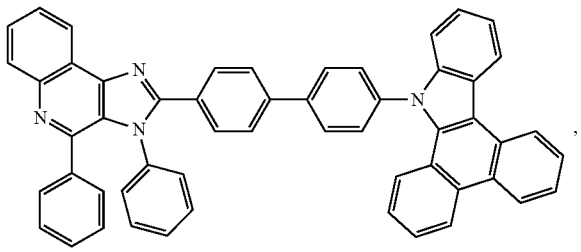

CJH-P100

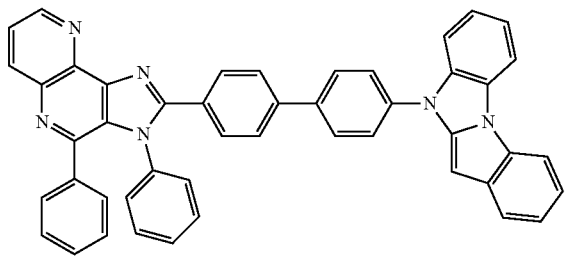

12. A material, wherein a raw material of the material contains one or a plurality of the imidazole derivatives according to claim 2.

13. A material, wherein a raw material of the material contains one or a plurality of the imidazole derivatives according to claim 3.

14. An organic light-emitting device, wherein a material of the organic light-emitting device contains one or a plurality of the imidazole derivatives according to claim 2.

15. An organic light-emitting device, wherein a material of the organic light-emitting device contains one or a plurality of the imidazole derivatives according to claim 3.

16. A method of preparing an organic light-emitting material comprising steps of preparing a layer of the imidazole derivative according to claim 2 and forming the organic light-emitting material including the layer of the imidazole derivative according to claim 2.

17. A method of preparing an organic light-emitting material comprising steps of preparing a layer of the imidazole derivative according to claim 3 and forming the organic light-emitting material including the layer of the imidazole derivative according to claim 3.

18. A method of preparing an organic light-emitting device comprising steps of preparing a layer of the imidazole derivative according to claim 2 and forming the organic light-emitting device including the layer of the imidazole derivative according to claim 2.

19. A method of preparing an organic light-emitting device comprising steps of preparing a layer of the imidazole derivative according to claim 3 and forming the organic light-emitting device including the layer of the imidazole derivative according to claim 3.

* * * * *